US012196744B2

(12) United States Patent
Keck et al.

(10) Patent No.: US 12,196,744 B2
(45) Date of Patent: Jan. 14, 2025

(54) HUMANIZED MOUSE MODELS FOR ASSESSING IMMUNE CELL THERAPY

(71) Applicant: The Jackson Laboratory, Bar Harbor, ME (US)

(72) Inventors: James Keck, Bar Harbor, ME (US); Jing Jiao, Bar Harbor, ME (US); Chunting Ye, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 0 days.

(21) Appl. No.: 17/705,037

(22) Filed: Mar. 25, 2022

(65) Prior Publication Data

US 2022/0214330 A1 Jul. 7, 2022

Related U.S. Application Data

(63) Continuation of application No. PCT/US2021/051734, filed on Sep. 23, 2021.

(60) Provisional application No. 63/083,003, filed on Sep. 24, 2020, provisional application No. 63/083,016, filed on Sep. 24, 2020.

(51) Int. Cl.
| | |
|---|---|
| G01N 33/68 | (2006.01) |
| A01K 67/0278 | (2024.01) |
| A61K 39/00 | (2006.01) |
| C12N 5/0783 | (2010.01) |
| G01N 33/50 | (2006.01) |
| A61N 5/10 | (2006.01) |

(52) U.S. Cl.
CPC ..... *G01N 33/5088* (2013.01); *A01K 67/0278* (2013.01); *A61K 39/461* (2023.05); *A61K 39/4611* (2023.05); *A61K 39/4631* (2023.05); *A61K 39/464412* (2023.05); *A61K 39/464413* (2023.05); *C12N 5/0636* (2013.01); *G01N 33/6863* (2013.01); *A01K 2207/12* (2013.01); *A01K 2207/15* (2013.01); *A01K 2227/105* (2013.01); *A01K 2267/0362* (2013.01); *A01K 2267/0387* (2013.01); *A61K 2239/26* (2023.05); *A61K 2239/31* (2023.05); *A61K 2239/38* (2023.05); *A61K 2239/48* (2023.05); *A61N 5/10* (2013.01)

(58) Field of Classification Search
None
See application file for complete search history.

(56) References Cited

U.S. PATENT DOCUMENTS

| | | | |
|---|---|---|---|
| 7,105,158 B1 | 9/2006 | D'Souza et al. | |
| 11,778,994 B2 * | 10/2023 | Brehm | A01K 67/0276 800/3 |
| 11,959,925 B2 | 4/2024 | Keck et al. | |
| 11,959,926 B2 | 4/2024 | Keck et al. | |
| 2005/0066375 A1 | 3/2005 | Thiam et al. | |
| 2010/0011450 A1 | 1/2010 | Garcia et al. | |
| 2011/0082091 A1 | 4/2011 | Hunig | |
| 2013/0316326 A1 | 11/2013 | Filinova | |
| 2015/0007357 A1 | 1/2015 | Bouguermouh et al. | |
| 2017/0172121 A1 | 6/2017 | Stevens et al. | |
| 2017/0273285 A1 | 9/2017 | Murphy et al. | |
| 2018/0187210 A1 | 7/2018 | Keck | |
| 2019/0091310 A1 | 3/2019 | Wright et al. | |
| 2019/0110450 A1 | 4/2019 | Serreze et al. | |
| 2020/0060245 A1 | 2/2020 | Brehm et al. | |
| 2020/0299644 A1 * | 9/2020 | Frank | G01N 33/5005 |
| 2021/0132080 A1 | 5/2021 | Keck et al. | |
| 2021/0214723 A1 * | 7/2021 | Kenderian | C07K 14/535 |
| 2023/0417763 A1 | 12/2023 | Keck et al. | |

FOREIGN PATENT DOCUMENTS

| | | |
|---|---|---|
| CN | 101022824 A | 8/2007 |
| CN | 102971420 A | 3/2013 |
| CN | 103304669 A | 9/2013 |
| CN | 103442768 A | 12/2013 |
| CN | 104160272 A | 11/2014 |
| CN | 104651299 A | 5/2015 |
| CN | 104812775 A | 7/2015 |
| CN | 104918483 A | 9/2015 |
| CN | 105452861 A | 3/2016 |
| EP | 1878342 A1 | 1/2008 |
| JP | 2007-244268 A | 9/2007 |
| JP | 2009-542253 A | 12/2009 |
| JP | 2016-518828 A | 6/2016 |
| WO | WO 92/11753 A1 | 7/1992 |
| WO | WO 2006/007529 A2 | 1/2006 |
| WO | WO 2008/010100 A2 | 1/2008 |
| WO | WO 2008/124142 A1 | 10/2008 |

(Continued)

OTHER PUBLICATIONS

Norelli et al., Monocyte-derived IL-1 and IL-6 are differentially required for cytokine-release syndrome and neurotoxicity due to CAR T cells (Nat Med, 2018, 24:739-748) (Year: 2018).*
International Search Report and Written Opinion mailed Jul. 31, 2018 in connection with Application No. PCT/US2018/027887.
International Preliminary Report on Patentability mailed Oct. 31, 2019 in connection with Application No. PCT/US2018/027887.
International Search Report and Written Opinion mailed Dec. 27, 2021 in connection with Application No. PCT/US2021/051734.
Abramowicz et al., Release of tumor necrosis factor, interleukin-2, and gamma-interferon in serum after injection of OKT3 monoclonal antibody in kidney transplant recipients. Transplantation. Apr. 1989;47(4):606-8.

(Continued)

*Primary Examiner* — Arthur S Leonard
(74) *Attorney, Agent, or Firm* — Wolf, Greenfield & Sacks, P.C.

(57) ABSTRACT

Provided herein are humanized mouse models and methods for determining whether administration of engineered immune cell therapies likely elicit cytokine release syndrome and/or determining the efficacy of an anti-disease therapy. Further, the models provided herein may be used to test the efficacy of different anti-CRS therapies.

11 Claims, 23 Drawing Sheets

(56) References Cited

FOREIGN PATENT DOCUMENTS

| WO | WO 2011/130512 A1 | 10/2011 |
|---|---|---|
| WO | WO 2012/099973 A2 | 7/2012 |
| WO | WO 2014/018625 A1 | 1/2014 |
| WO | WO 2014/071397 A2 | 5/2014 |
| WO | WO 2017/040930 A2 | 3/2017 |
| WO | WO 2018/102546 A1 | 6/2018 |
| WO | WO 2018/209344 A1 | 11/2018 |
| WO | 2019/084018 A1 | 5/2019 |
| WO | WO 2019/141251 A1 | 7/2019 |
| WO | 2020/206149 A2 | 10/2020 |

OTHER PUBLICATIONS

Brady et al., Preclinical screening for acute toxicity of therapeutic monoclonal antibodies in a hu-SCID model. Clin Transl Immunology. Dec. 19, 2014;3(12):e29, 7 pages. doi: 10.1038/cti.2014.28.

Carayol et al., Quantitative analysis of T helper 1, T helper 2, and inflammatory cytokine expression in patients after allogeneic bone marrow transplantation: relationship with the occurrence of acute graft-versus-host disease. Transplantation. May 15, 1997;63(9):1307-13.

Carson et al., A fatal cytokine-induced systemic inflammatory response reveals a critical role for NK cells. J Immunol. Apr. 15, 1999;162(8):4943-51.

Duff, Expert Scientific Group on Phase One Clinical Trials, Final Report. The Stationery Office. Nov. 30, 2006;1-108. https://webarchive.nationalarchives.gov.uk/20130105143109/http://www.dh.gov.uk/prod_consum_dh/groups/dh_digitalassets/@dh/@en/documents/digitalasset/dh_073165.pdf [last accessed Jan. 15, 2020].

England et al., Preclinical Pharmacokinetics and Biodistribution Studies of 89Zr-Labeled Pembrolizumab. J Nucl Med. Jan. 2017;58(1):162-168. doi: 10.2967/jnumed.116.177857. Epub Aug. 4, 2016.

Gogishvili et al., Rapid regulatory T-cell response prevents cytokine storm in CD28 superagonist treated mice. PLoS One. 2009;4(2):e4643, 9 pages. doi: 10.1371/journal.pone.0004643. Epub Feb. 27, 2009.

Gribble et al., Toxicity as a result of immunostimulation by biologics. Expert Opin Drug Metab Toxicol. Apr. 2007;3(2):209-34.

Hunig, Manipulation of regulatory T-cell number and function with CD28-specific monoclonal antibodies. Adv Immunol. 2007;95:111-48.

Jin et al., Modeling anti-CD19 CAR T cell therapy in humanized mice with human immunity and autologous leukemia. EBioMedicine. Jan. 2019;39:173-181. doi: 10.1016/j.ebiom.2018.12.013. Epub Dec. 20, 2018.

Lee et al., Current concepts in the diagnosis and management of cytokine release syndrome. Blood. Jul. 10, 2014;124(2):188-95. doi: 10.1182/blood-2014-05-552729. Epub May 29, 2014.

Malcolm et al., A humanized mouse model of cytokine release: Comparison of CD3-specific antibody fragments. J Immunol. Methods. Oct. 31, 2012;384(1-2):33-42. doi: 10.1016/j.jim.2012.07.001. Epub Jul. 11, 2012.

McIntosh et al., No irradiation required: The future of humanized immune system modeling in murine hosts. Chimerism. Apr. 3, 2015;6(1-2):40-5. doi: 10.1080/19381956.2016.1162360. Epub May 12, 2016.

Nguyen et al., Loss of Siglec expression on T lymphocytes during human evolution. Proc Natl Acad Sci USA. May 16, 2006;103(20):7765-70. Epub May 8, 2006.

Schraven et al., CD28 superagonists: what makes the difference in humans? Immunity. May 2008;28(5):591-5. doi: 10.1016/j.immuni.2008.04.003.

Sterner et al., GM-CSF inhibition reduces cytokine release syndrome and neuroinflammation but enhances CAR-T cell function in xenografts. Blood. Feb. 14, 2019;133(7):697-709. doi: 10.1182/blood-2018-10-881722. Epub Nov. 21, 2018.

Suntharalingam et al., Cytokine storm in a phase 1 trial of the anti-CD28 monoclonal antibody TGN1412. N Engl J Med. Sep. 7, 2006;355(10):1018-28. Epub Aug. 14, 2006.

Teachey et al., Identification of Predictive Biomarkers for Cytokine Release Syndrome after Chimeric Antigen Receptor T-cell Therapy for Acute Lymphoblastic Leukemia. Cancer Discov. Jun. 2016;6(6):664-79. doi: 10.1158/2159-8290.CD-16-0040. Epub Apr. 13, 2016.

Wang et al., The cytokine storm and factors determining the sequence and severity of organ dysfunction in multiple organ dysfunction syndrome. Am J Emerg Med. Jul. 2008;26(6):711-5. doi: 10.1016/j.ajem.2007.10.031.

Weir, Hazard identification and risk assessment for biologics targeting the immune system. J Immunotoxicol. Jan. 2008;5(1):3-10. doi: 10.1080/15476910801897409.

Weißmüller et al., TGN1412 Induces Lymphopenia and Human Cytokine Release in a Humanized Mouse Model. PLoS One. Mar. 9, 2016;11(3):e0149093, 19 pages. doi: 10.1371/journal.pone.0149093.

Wing, Monoclonal antibody first dose cytokine release syndromes-mechanisms and prediction. J Immunotoxicol. Jan. 2008;5(1):11-5. doi: 10.1080/15476910801897433.

Ye et al., A rapid, sensitive, and reproducible in vivo PBMC humanized murine model for determining therapeutic-related cytokine release syndrome. FASEB J. Sep. 2020;34(9):12963-12975. doi: 10.1096/fj.202001203R. Epub Aug. 9, 2020.

Yong et al., Humanized Mice as Unique Tools for Human-Specific Studies. Arch Immunol Ther Exp (Warsz). Aug. 2018;66(4):245-266. doi: 10.1007/s00005-018-0506-x. Epub Feb. 7, 2018.

Adigbli et al., Development of LT-HSC-Reconstituted Non-Irradiated NBSGW Mice for the Study of Human Hematopoiesis In Vivo. Front Immunol. Mar. 25, 2021;12:642198. doi: 10.3389/fimmu.2021.642198.

Ali et al., Xenogeneic graft-versus-host-disease in NOD-scid IL-2Rγnull mice display a T-effector memory phenotype. PLoS One. 2012;7(8):e44219. doi: 10.1371/journal.pone.0044219. Epub Aug. 28, 2012.

Brehm et al., Engraftment of human HSCs in nonirradiated newborn NOD-scid IL2rγ null mice is enhanced by transgenic expression of membrane-bound human SCF. Blood. Mar. 22, 2012;119(12):2778-88. doi: 10.1182/blood-2011-05-353243. Epub Jan. 12, 2012.

Futrega et al., Direct bone marrow HSC transplantation enhances local engraftment at the expense of systemic engraftment in NSG mice. Sci Rep. Apr. 11, 2016;6:23886. doi: 10.1038/srep23886.

Gregoire-Gauthier et al., Use of immunoglobulins in the prevention of GvHD in a xenogeneic NOD/SCID/γc-mouse model. Bone Marrow Transplant. Mar. 2012;47(3):439-50. doi: 10.1038/bmt.2011.93. Epub May 16, 2011.

King et al., Human peripheral blood leucocyte non-obese diabetic-severe combined immunodeficiency interleukin-2 receptor gamma chain gene mouse model of xenogeneic graft-versus-host-like disease and the role of host major histocompatibility complex. Clin Exp Immunol. Jul. 2009;157(1):104-18. doi: 10.1111/j.1365-2249.2009.03933.x.

Pearson et al., Creation of "humanized" mice to study human immunity. Curr Protoc Immunol. May 2008;Chapter 15:Unit 15.21. doi: 10.1002/0471142735.im1521s81.

Ponomaryov et al., Induction of the chemokine stromal-derived factor-1 following DNA damage improves human stem cell function. J Clin Invest. Dec. 2000;106(11):1331-9. doi: 10.1172/JCI10329.

Ratajczak et al., Emerging Strategies to Enhance Homing and Engraftment of Hematopoietic Stem Cells. Stem Cell Rev Rep. Feb. 2016;12(1):121-8. doi: 10.1007/s12015-015-9625-5.

Singh et al., An improved protocol for efficient engraftment in NOD/LTSZ-SCIDIL-2Rγnull mice allows HIV replication and development of anti-HIV immune responses. PLoS One. 2012;7(6):e38491. doi: 10.1371/journal.pone.0038491. Epub Jun. 4, 2012.

Yaguchi et al., Human PBMC-transferred murine MHC class I/II-deficient NOG mice enable long-term evaluation of human immune responses. Cell Mol Immunol. Nov. 2018;15(11):953-962. doi: 10.1038/cmi.2017.106. Epub Nov. 20, 2017.

(56) References Cited

OTHER PUBLICATIONS

Anderson et al., The NOD Mouse: A Model of Immune Dysregulation. Annu Rev Immunol. 2005;23:447-85. doi: 10.1146/annurev.immunol.23.021704.115643.

Ashizawa et al., Antitumor Effect of Programmed Death-1 (PD-1) Blockade in Humanized the; NOG-MHC Double Knockout Mouse. Clin Cancer Res. Jan. 1, 2017;23(1):149-158. doi: 10.1158/1078-0432.CCR-16-0122. Epub Jul. 25, 2016.

Beier et al., Perinatal lethality (ple): a mutation caused by integration of a transgene into distal mouse chromosome 15. Genomics. May 1989;4(4):498-504. doi: 10.1016/0888-7543(89)90272-3.

Bosma et al., The mouse mutation severe combined immune deficiency (scid) is on chromosome 16. Immunogenetics. 1989;29(1):54-7.

Brehm et al., 1—NOD-scid IL2rg$^{null}$ (NSG) mice deficient in murine MHC Class I and Class II expression support engraftment of functional human T cells in the absence of acute xenogeneic GVHD following injection of PBMC. AACR Annual Meeting. Apr. 18, 2018. https://www.abstractsonline.com/pp8/#!/4562/presentation/3784 [last accessed Feb. 10, 2020]. Abstract only, 1pg.

Brehm et al., Generation of improved humanized mouse models for human infectious diseases. J Immunol Methods. Aug. 2014;410:3-17. doi: 10.1016/j.jim.2014.02.011. Epub Mar. 4, 2014.

Cosgrove et al., Mice lacking MHC class II molecules. Cell. Sep. 6, 1991;66(5):1051-66.

Covassin et al., Human immune system development and survival of non-obese diabetic (NOD)-scid IL2rγ$^{null}$ (NSG) mice engrafted with human thymus and autologous haematopoietic stem cells. Clin Exp Immunol. Dec. 2013;174(3):372-88. doi: 10.1111/cei.12180.

Covassin et al., Human peripheral blood CD4 T cell-engrafted non-obese diabetic-scid IL2rγ$^{null}$ H2-Ab1$^{tm1Gru}$ Tg (human leucocyte antigen D-related 4) mice: a mouse model of; human allogeneic graft-versus-host disease. Clin Exp Immunol. Nov. 2011;166(2):269-80. doi: 10.1111/j.1365-2249.2011.04462.x.

Dai et al., Stress-impaired transcription factor expression and insulin secretion in transplanted human islets. J Clin Invest. May 2, 2016;126(5):1857-70. doi: 10.1172/JCI83657. Epub Apr. 11, 2016.

Dobie et al., Variegated transgene expression in mouse mammary gland is determined by the transgene integration locus. Proc Natl Acad Sci U S A. Jun. 25, 1996;93(13):6659-64. doi: 10.1073/pnas.93.13.6659.

Dolatshad et al., A versatile transgenic allele for mouse overexpression studies. Mamm Genome. Dec. 2015;26(11-12):598-608. doi: 10.1007/s00335-015-9602-y. Epub Sep. 14, 2015.

Erlich et al., HLA DR-DQ Haplotypes and Genotypes and Type 1 Diabetes Risk: Analysis of the Type 1 Diabetes Genetics Consortium Families. Diabetes. Apr. 2008;57(4):1084-92. doi: 10.2337/db07-1331. Epub Feb. 5, 2008.

Garrick et al., Repeat-induced gene silencing in mammals. Nat Genet. Jan. 1998;18(1):56-9. doi: 10.1038/ng0198-56.

Grusby et al., Depletion of CD4$^{+}$ T cells in major histocompatibility complex class II-deficient mice. Science. Sep. 20, 1991;253(5026):1417-20. doi: 10.1126/science.1910207.

Hatada et al., The influence of chromosomal location on the expression of two transgenes in mice. J Biol Chem. Jan. 8, 1999;274(2):948-55. doi: 10.1074/jbc.274.2.948.

Ito et al., NOD/SCID/gamma$_c^{null}$ mouse: an excellent recipient mouse model for engraftment of human cells. Blood. Nov. 1, 2002;100(9):3175-82.

Jarchum et al., In Vivo Cytotoxicity of Insulin-Specific CD8$^{+}$ T-cells in HLA-A*0201 Transgenic NOD mice. Diabetes. Oct. 2007;56(10):2551-60. Epub Jul. 9, 2007.

Johnson et al., Inhibition of Autoimmune Diabetes in Nonobese Diabetic Mice by Transgenic Restoration of H2-E MHC Class II Expression: Additive, But Unequal, Involvement of Multiple APC Subtypes. J Immunol. Aug. 15, 2001;167(4):2404-10.

Kim et al., Humanized mice for studying human leukocyte integrins in vivo. Methods Mol Biol. 2012;757:509-21. doi: 10.1007/978-1-61779-166-6_30. Author Manuscript, 13 pages.

King, The use of animal models in diabetes research. Br J Pharmacol. Jun. 2012;166(3):877-94. doi: 10.1111/j.1476-5381.2012.01911.x.

Ledford, CRISPR Editing Wreaks Chromosomal Mayhem in Human Embryos. Nature. Jul. 2, 2020;583:17-18.

Lee et al., Unexpected CRISPR on-target effects. Nat Biotechnol. Sep. 2018;36(8):703-704. 2 pages. doi: 10.1038/nbt.4207. Epub Jul. 30, 2018.

Li et al., Identification of autoreactive CD8$^{+}$ T cell responses targeting chromogranin A in humanized NOD mice and type 1 diabetes patients. Clin Immunol. Jul. 2015;159(1):63-71. doi: 10.1016/j.clim.2015.04.017. Epub May 6, 2015.

Madsen et al., Mice lacking all conventional MHC class II genes. Proc Natl Acad Sci USA. Aug. 31, 1999;96(18):10338-43.

Marron et al., Functional evidence for the mediation of diabetogenic T cell responses by HLA-A2.1 MHC class I molecules through transgenic expression in NOD mice. Proc Natl Acad Sci U S A. Oct. 15, 2002;99(21):13753-8. Epub Oct. 2, 2002.

Niens et al., Prevention of "Humanized" Diabetogenic CD8 T-cell Responses in HLA-Transgenic NOD mice by a Multipeptide Coupled-Cell approach. Diabetes. Apr. 2011;60(4):1229-36. doi: 10.2337/db10-1523. Epub Feb. 23, 2011.

Palmiter et al., Germ-line transformation of mice. Annu Rev Genet. 1986;20:465-99. doi: 10.1146/annurev.ge.20.120186.002341. Author Manuscript, 35 pages.

Pascolo et al., HLA-A2.1-restricted Education and Cytolytic Activity of CD8(+) T Lymphocytes from β2 Microglobulin (β2m) HLA-A2.1 Monochain Transgenic H-2Db β2m Double Knockout Mice. J Exp Med. Jun. 16, 1997;185(12):2043-51.

Pearson et al., Non-obese diabetic-recombination activating gene-1 (NOD-Rag1$^{null}$) interleukin (IL)-2 receptor common gamma chain (IL2rγ$^{null}$) null mice: a radioresistant model for human lymphohaematopoietic engraftment. Clin Exp Immunol. Nov. 2008;154(2):270-84. doi: 10.1111/j.1365-2249.2008.03753.x. Epub Sep. 8, 2008.

Perarnau et al., Single $H2K^b$, $H2D^b$ and double $H2K^bD^b$ knockout mice: peripheral CD8$^{+}$ T cell repertoire and anti-lymphocytic choriomeningitis virus cytolytic responses. Eur J Immunol. Apr. 1999;29(4):1243-52.

Pino et al., Development of novel major histocompatibility complex class I and class II-deficient NOD-SCID IL2R gamma chain knockout mice for modeling human xenogeneic graft-versus-host disease. Methods Mol Biol. 2010;602:105-17. doi: 10.1007/978-1-60761-058-8_7. Abstract.

Schaefer et al., Unexpected mutations after CRISPR-Cas9 editing in vivo. Nat Methods. May 30, 2017;14(6):547-548. doi: 10.1038/nmeth.4293. Author Manuscript, pages.

Schloss et al., HLA-B*39:06 Efficiently Mediates Type 1 Diabetes in a Mouse Model Incorporating Reduced Thymic Insulin Expression. J Immunol. May 15, 2018;200(10):3353-3363. doi: 10.4049/jimmunol.1701652. Epub Apr. 9, 2018.

Schultz et al., Human cancer growth and therapy in immunodeficient mouse models. Cold Spring Harb Protoc. Jul. 1, 2014;2014(7):694-708. doi: 10.1101/pdb.top073585. Author Manuscript, 24 pages.

Schultz et al., Human lymphoid and myeloid cell development in NOD/LtSz-scid IL2Rγ$^{null}$ mice engrafted with mobilized human hemopoietic stem cells. J Immunol. May 15, 2005;174(10):6477-89.

Sellers et al., Immunological Variation Between Inbred Laboratory Mouse Strains: Points to Consider in Phenotyping Genetically Immunomodified Mice. Vet Pathol. Jan. 2012;49(1):32-43. doi: 10.1177/0300985811429314. Epub Nov. 30, 2011.

Serreze et al., "Humanized" HLA Transgenic NOD Mice to Identify Pancreatic β Cell Autoantigens of Potential Clinical Relevance to Type 1 Diabetes. Ann N.Y. Acad Sci. Apr. 2007;1103:103-11. Epub Mar. 21, 2007.

Serreze et al., Bridging Mice to Men: Using HLA Transgenic Mice to Enhance the Future Prediction and Prevention of Autoimmune Type 1 Diabetes in Humans. Methods Mol Biol. 2016;1438:137-51. doi: 10.1007/978-1-4939-3661-8_9.

Serreze et al., Loss of Intra-Islet CD20 Expression May Complicate Efficacy of B-Cell-Directed Type 1 Diabetes Therapies. Diabetes. Nov. 2011;60(11):2914-21. 8 pages. doi: 10.2337/db11-0705. Epub Sep. 16, 2011.

(56) References Cited

OTHER PUBLICATIONS

Serreze et al., Major Histocompatibility Complex Class I-Deficient NOD-β2mnull Mice are Diabetes and Insulitis Resistant. Diabetes. Mar. 1994;43(3):505-9.

Shi et al., Germ line deletion of the CD1 locus exacerbates diabetes in the NOD mouse. Proc Natl Acad Sci U S A. Jun. 5, 2001;98(12):6777-82.

Simecek et al., Genetic Analysis of Substrain Divergence in Non-Obese Diabetic (NOD) Mice. G3 (Bethesda). Mar. 3, 2015;5(5):771-5. doi: 10.1534/g3.115.017046.

Takai et al., HLA-A*0201-Restricted T Cells From Humanized NOD Mice Recognize Autoantigens of Potential Clinical Relevance to Type 1 Diabetes. J Immunol. Mar. 1, 2006;176(5):3257-65.

Tong et al., CAR Technology and Its Application in Treatment of Multiple Myeloma. Chinese Journal of Experimental Hematology. Feb. 20, 2016. 279-284.

Vugmeyster et al., Major histocompatibility complex (MHC) class I $K^bD^b$ −/− deficient mice possess functional CD8+ T cells and natural killer cells. Proc Natl Acad Sci U S A. Oct. 13, 1998;95(21):12492-7.

Wang et al., CD1-restricted NK T cells Protect Nonobese Diabetic Mice from Developing Diabetes. J Exp Med. Aug. 6, 2001;194(3):313-19.

Wang et al., Immune system of mice. Chinese Journal of Immunology. Mar. 20, 2016. 289-298.

Yaguchi et al., MHC class I/II deficient NOG mice are useful for analysis of human T/B cell responses for human tumor immunology research. J ImmunoTher Cancer. Nov. 8-10, 2013;1(1):P39. Poster Presentation, 1pg.

Inoue et al., Safety evaluation of biotechnology-derived pharmaceuticals. Drug Deliv System. 2011;26-6:622-27.

Merryman et al., Immune Checkpoint Blockade and Hematopoietic Stem Cell Transplant. Curr Hematol Malig Rep. Feb. 2017;12(1):44-50. doi: 10.1007/s11899-017-0362-5.

\* cited by examiner

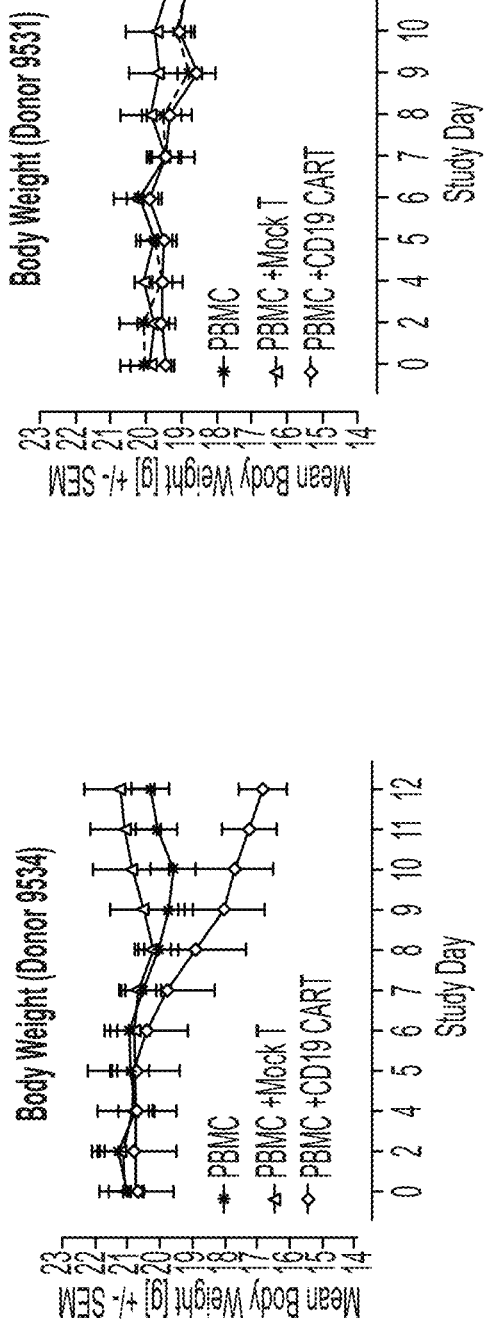
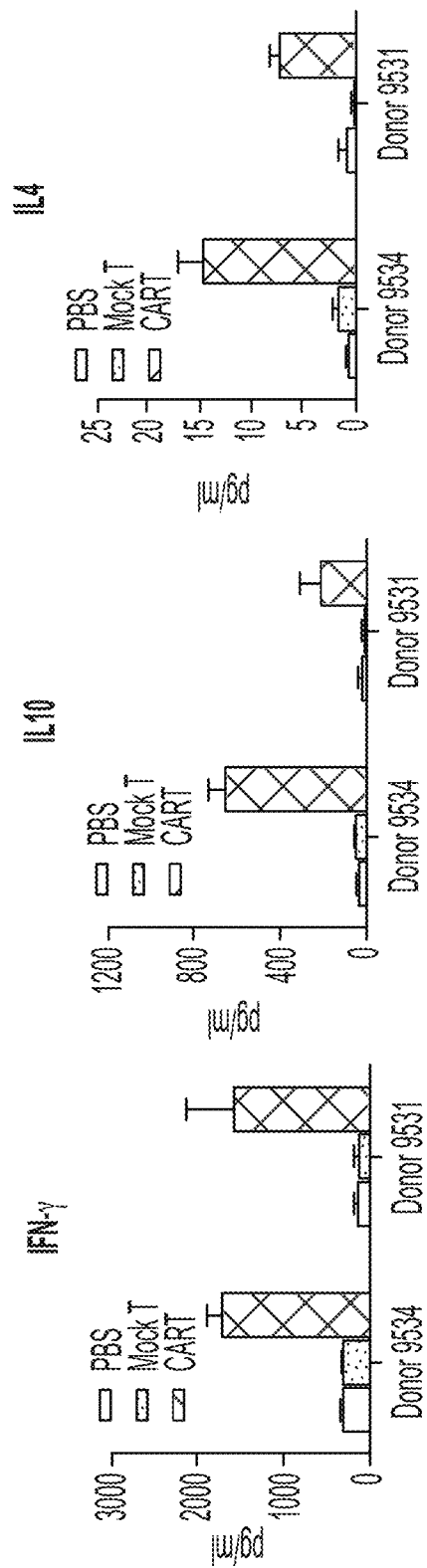
FIG. 11C
FIG. 11D

HUMANIZED MOUSE MODELS FOR ASSESSING IMMUNE CELL THERAPY

RELATED APPLICATIONS

This application is a continuation of International Application No. PCT/US2021/051734, filed Sep. 23, 2021, which claims priority under 35 U.S.C. § 119(e) to U.S. Provisional Application No. 63/083,003, filed on Sep. 24, 2020, and U.S. Provisional Application No. 63/083,016, filed on Sep. 24, 2020, the entire content of each of which is incorporated by reference herein.

BACKGROUND

Adoptive cell therapy (ACT), such as chimeric antigen receptor (CAR) immune cell therapy (e.g., CAR T cell therapy or CAR-natural killer cell (CAR-NK) therapy) has become a revolutionary new cancer treatment. It has proven to be an effective new treatment for hematological malignancies and is currently being developed to treat solid tumor cancers. ACT utilizes gene transfer to reprogram immune cells expressing an engineered antigen receptor, which enables immune cells (e.g., T cells, B cells, and/or natural killer (NK) cells) to recognize and target (bind to) cell surface antigens specific to a diseased cell, such as a tumor cell, further eliminating diseased cells carrying the antigen. Currently, there are three Food and Drug Administration (FDA)-approved CAR T cell products, for example: two for the treatment B-cell lymphoma, one for the treatment of advanced mantle cell lymphoma (MCL). Similarly, NK cells play a pivotal role as the body's first-line defense against virally infected and malignant cells.

SUMMARY

The most common side effects of immune cell therapy, such as ACT (e.g., CAR T cell, CAR B cell, and/or CAR NK cell therapy) are cytokine release syndrome (CRS) and encephalopathy syndrome (neurotoxicity)—two major complications that can lead to significant morbidity and mortality. CRS is a cytokine-mediated systemic inflammatory response caused by multiple cytokines following in vivo immune cell (e.g., T cell, B cell, NK cell) activation and expansion. Immune cells comprising an engineered antigen receptor (i.e., engineered immune cells), diseased cells (e.g., tumor cells), and other immune cells can release cytokines and contribute to the induction of CRS. The main cytokines associated with pathogenesis of CRS include interleukin (IL) 6, IL10, interferon (IFN)-γ, monocyte chemoattractant protein 1 (MCP-1), and granulocyte-macrophage colony-stimulating factor (GM-CSF). Several other cytokines, including but not limited to tumor necrosis factor (TNF), IL1, IL2, IL2 receptor alpha (IL2Rα), and IL8 have also been implicated in CRS development. Although the mechanism of CRS remains to be better understood, several factors contributing to this toxicity include the structure of the chimera antigen receptor, high tumor burden, higher engineered immune cell (e.g., T cell, B cell, NK cell) infusion dose, and other patient-specific factors, such as pre-existent state of inflammation and baseline endothelial activation. To overcome the toxicity of CRS, one approach for CRS treatment is to apply anti-cytokine therapy early in the CRS development to prevent developed into life-threatening high-grade CRS. Currently, tocilizumab (IL6 antagonist) is approved by the FDA for the treatment of severe or life-threatening engineered immune cell (e.g., T cell, B cell, NK cell) induced CRS.

Preclinical models of CRS are useful for identifying agents effective for CRS treatment that do not interfere with the cytokine-mediated anti-tumor effects of engineered immune cells (e.g., CAR T cells, CAR B cells, or CAR NK cells). In addition, preclinical models of CRS are helpful for evaluating which engineered immune cells (e.g., T cells, B cells, NK cells) (e.g., which specific CAR construct) induce the least CRS and remain therapeutically effective.

An additional need has come from the advancement of universal allogeneic engineered immune cell (e.g., CAR T cell, CAR B cell, or CAR NK cell) therapies, where the same engineered immune cell is utilized across a patient group or population and there is presently no pre-screen for safety and efficacy available (see, e.g., Zhao J et al. *Journal of Hematology & Oncology* 2018; 11(132)); however, currently there are limited preclinical models to serve these purposes. Those that are available are either not representative of all the various types of immune cells that contribute to CRS induction in the tumor microenvironment or require laborious model development and engineered immune cell (e.g., T cell, B cell, NK cell) production.

It should be understood that the term "engineered immune cell" herein refers to any immune cell (e.g., T cell, B cell, or NK cell) that comprises (e.g., expresses) an engineered antigen receptor, i.e., a non-naturally-occurring receptor that specifically binds to a cell surface antigen of interest. For example, a "CAR immune cell" such as a "CAR T cell" is considered an "engineered immune cell." Other examples of engineered immune cells include T cells with an engineered T cell receptor (TCR), engineered (e.g., edited) tumor infiltrating lymphocytes (eTIL) and engineered regulatory T cells (eTregs).

Some aspects of the present disclosure provide a method comprising: administering human immune cells and human peripheral blood mononuclear cells (PBMCs) to an immunodeficient mouse, wherein the human immune cells comprise an engineered receptor that specifically binds to a cell surface antigen on the diseased human cells, and the immunodeficient mouse has been engrafted with diseased human cells; and assaying the immunodeficient mouse for symptoms of CRS and/or efficacy of the human immune cells.

In some embodiments, the method further comprises administering the diseased human cells to an immunodeficient mouse.

In some embodiments, the human immune cells are selected from T cells, B cells, natural killer (NK) cells, monocytes, dendritic cells, and neutrophils.

In some embodiments, the human immune cells are genomically-modified immune cells.

In some embodiments, the engineered receptor is a CAR.

In some embodiments, the human immune cell is a T cell with an engineered CAR.

In some embodiments, the engineered receptor is a T cell receptor (TCR).

In some embodiments, the human immune cell is a T cell with an engineered TCR.

In some embodiments, the human immune cells are regulatory T cells (Tregs).

In some embodiments, the human immune cells are tumor-infiltrating lymphocytes (TILs).

In some embodiments, the diseased human cells are selected from blood cells, muscle cells, and neuronal cells.

In some embodiments, the diseased human cells are tumor cells.

In some embodiments, the tumor cells are primary tumor cells.

In some embodiments, the diseased human cells are cancerous cells.

In some embodiments, the diseased human cells are non-cancerous cells.

In some embodiments, the PBMCs and the human immune cells are autologous.

In some embodiments, the diseased human cells, the PBMCs and the human immune cells are autologous.

In some embodiments, the PBMCs and the human immune cells are allogeneic.

In some embodiments, the method further comprises irradiating the immunodeficient mouse prior to administering the human immune cells and the human PBMCs to an immunodeficient mouse.

In some embodiments, the human immune cells and the human PBMCs are administered simultaneously.

In some embodiments, the method further comprises administering to the immunodeficient mouse a candidate agent for treating CRS prior to the assaying.

In some embodiments, the mouse is a non-obese diabetic (NOD) mouse.

In some embodiments, the mouse comprises a null mutation in a Prkdc gene and a null mutation in an Il2rg gene.

In some embodiments, the mouse has a NOD-Cg.-Prkdc$^{scid}$IL2$^{tm1wJl}$/SzJ genotype.

In some embodiments, the mouse lacks functional major histocompatibility complex I (MHC I) and major histocompatibility complex II (MHC II).

In some embodiments, the mouse comprises a null H2-Ab1 gene.

In some embodiments, the mouse comprises a null MHC Class I H2-K1 gene.

In some embodiments, the mouse comprises a null MHC Class I H2-D1 gene.

In some embodiments, the mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ mouse (NSG-(K$^b$ D$^b$)$^{null}$ (IA$^{null}$) mouse).

In some embodiments, the assaying comprises measuring a circulating level of a cytokine selected from the group consisting of: interleukin (IL)-6, IL10, interferon (IFN)-γ, monocyte chemoattractant protein 1 (MCP-1), granulocyte-macrophage colony-stimulating factor (GM-CSF), tumor necrosis factor (TNF), IL-1, IL-2, IL-2-receptor alpha (IL-2Rα), IL-8, IL-4, IL-18, and macrophage inflammatory protein (MIP) 4.

In some embodiments, the method further comprises determining that the likelihood of CRS induction is high when:
  a human IFN-γ level in the mouse is ≥1,800 pg/ml±10%;
  a human IL-10 level in the mouse is ≥120 pg/ml±10%;
  a human IL-6 level in the mouse is ≥25 pg/ml±10%;
  a human IL-2 level in the mouse is ≥80 pg/ml±10%;
  a human IL-4 level in the mouse is ≥120 pg/ml±10%;
  a human TNFα level in the mouse is ≥120 pg/ml±10%;
  a human IL-8 level in the mouse is ≥15 pg/ml±10%;
  a human MCP-1 level in the mouse is ≥120 pg/ml±10%;
  and/or a human GM-CSF level in the mouse is ≥600 pg/ml±10%.

In some embodiments, the method further comprises assaying the mouse for macrophage activation syndrome (MAS).

In some embodiments, the likelihood of MAS is determined by measuring the circulating levels of IL-6, IL-1, and/or IFN-γ.

In some embodiments, the method further comprises assaying the mouse for neurotoxicity.

In some embodiments, the likelihood of neurotoxicity is determined by measuring the circulating levels of IFN-γ, IL-6, and/or TNF-α.

In some embodiments, the method further comprises performing a serum biochemical analysis of liver-kidney function.

In some embodiments, the serum biochemical analysis comprises measuring the levels of at least one of the following markers: aspartate transaminase (AST), albumin, total bilirubin, creatinine, or blood urea nitrogen.

In some embodiments, the method further comprises determining whether the candidate agent reduces the level of one or more circulating cytokines.

In some embodiments, the method comprises determining that the candidate agent does reduce the level of one or more circulating cytokines when the circulating level of the one or more cytokines is reduced 30-100% in a mouse administered the human immune cells and the candidate agent, relative to a mouse administered the human immune cells without the candidate agent.

In some embodiments, the diseased human cells are human tumor cells, and the assaying comprises measuring growth of the human tumor cells.

In some embodiments, the growth of the human tumor cells is measured over time.

In some embodiments, a reduction in tumor volume of 20% or more relative to a control mouse that was not administered the human immune cells is indicative of efficacy.

In some embodiments, a reduction in tumor burden of 20% or more relative to a control mouse that was not administered the human immune cells is indicative of efficacy.

In some embodiments, the growth of the human tumor cells is used to determine progression-free survival, tumor volume doubling time, relative tumor volume, tumor growth inhibition, or tumor growth rate.

CAR T cell treatment compared to mice with CD19 CAR T cell treatment alone (no PBMC) or PBMC engraftment alone (no CAR T cells).

Figure 5A:
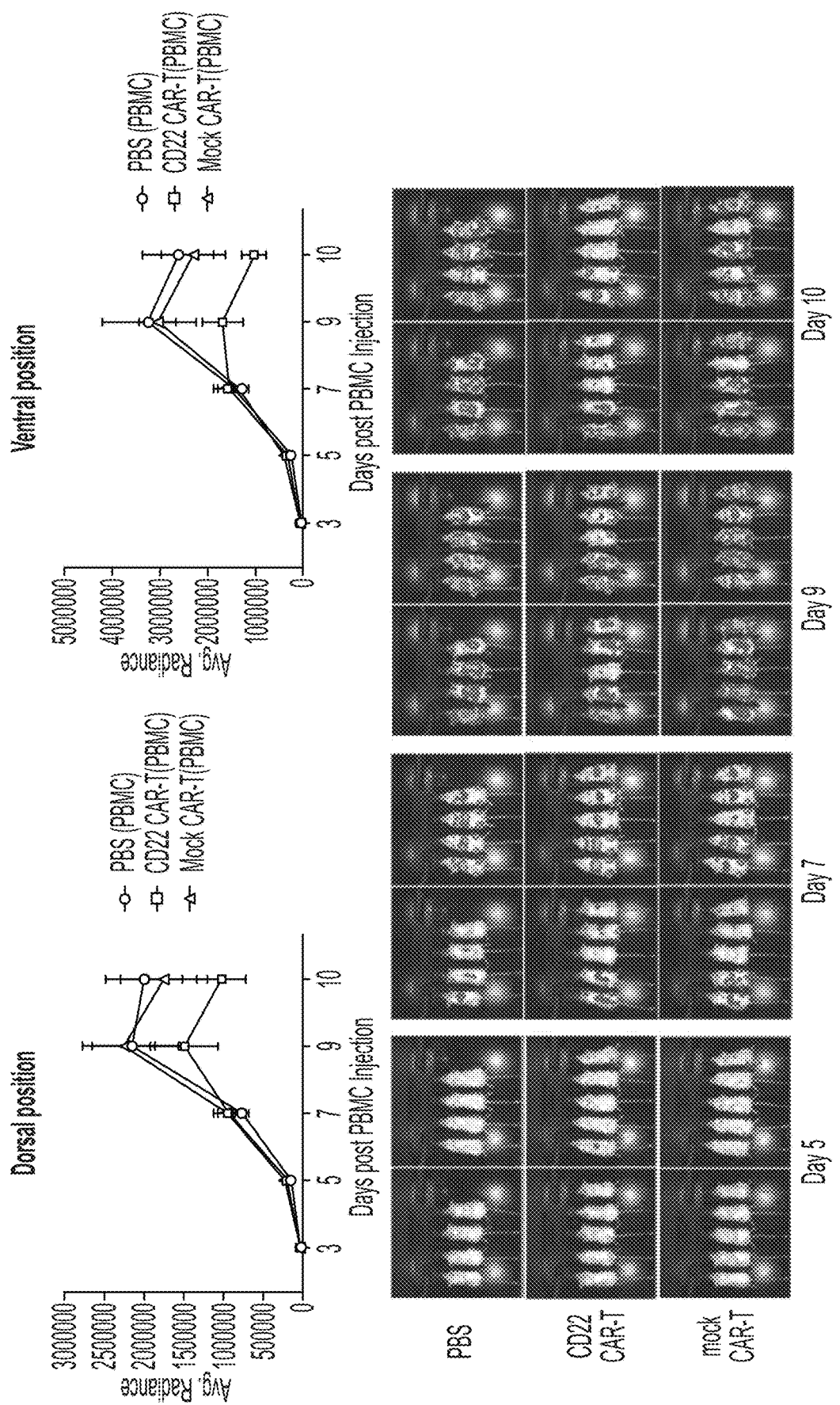
Figure 5B:
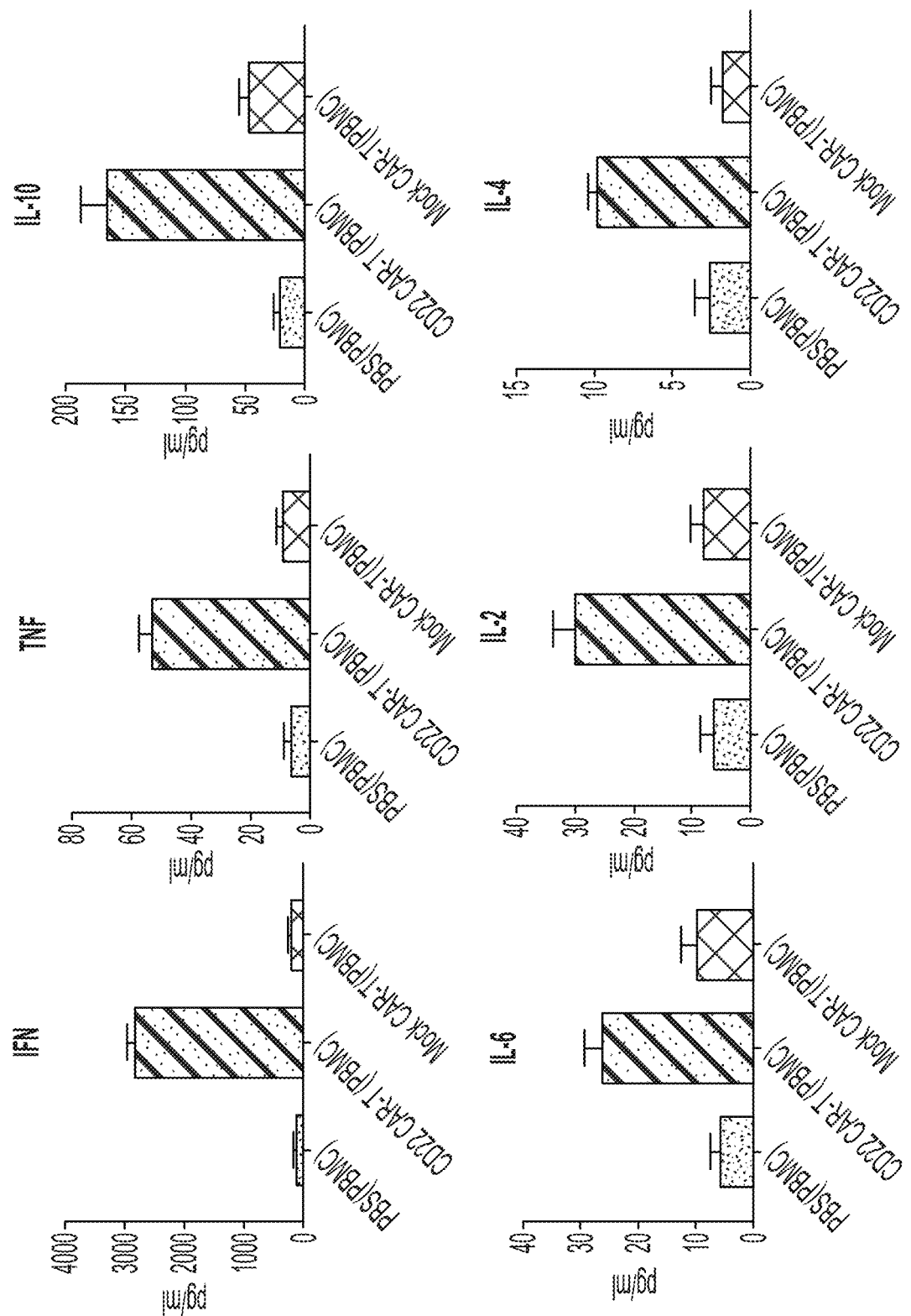

FIG. 5A provides data demonstrating that autologous CD22 CAR T cell treatment in PBMC humanized DKO mice blocked Raji_Luc tumor progression. FIG. 5B provides data demonstrating that autologous CD22 CAR T cell treatment in PBMC humanized DKO mice induced higher human cytokine release compared to mock T cell treatment.

Figure 6A:
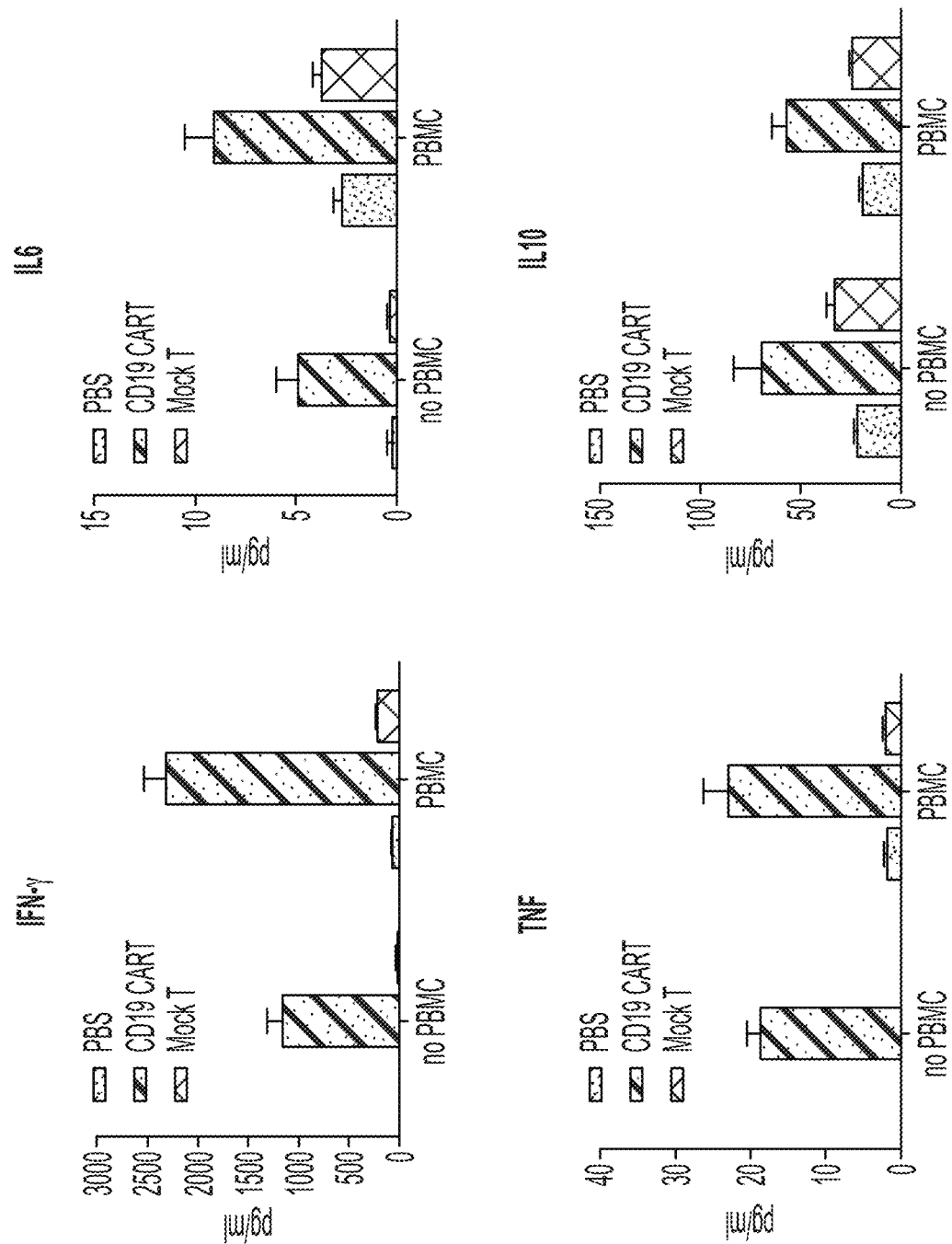
Figure 6B:
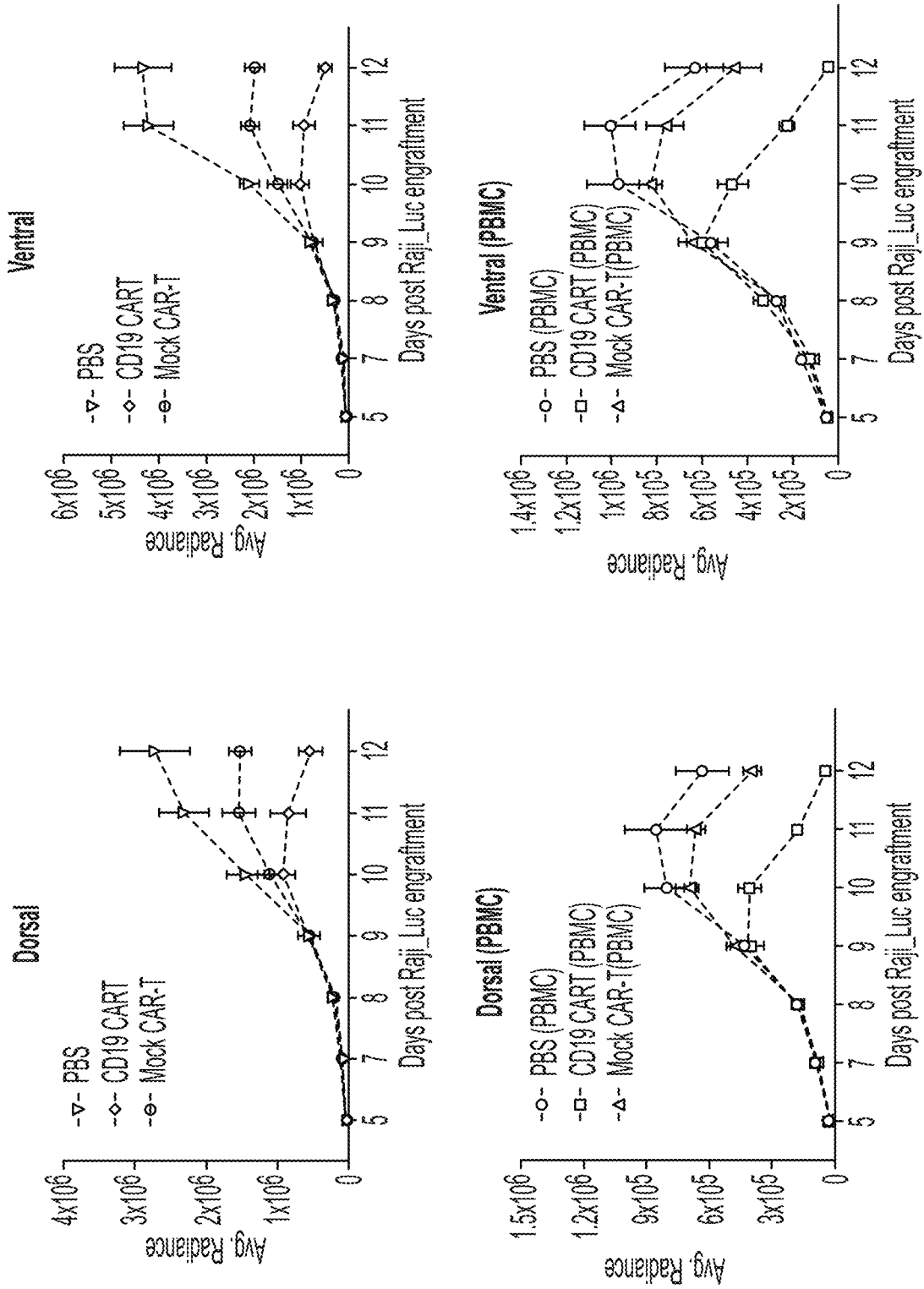
Figure 6C:
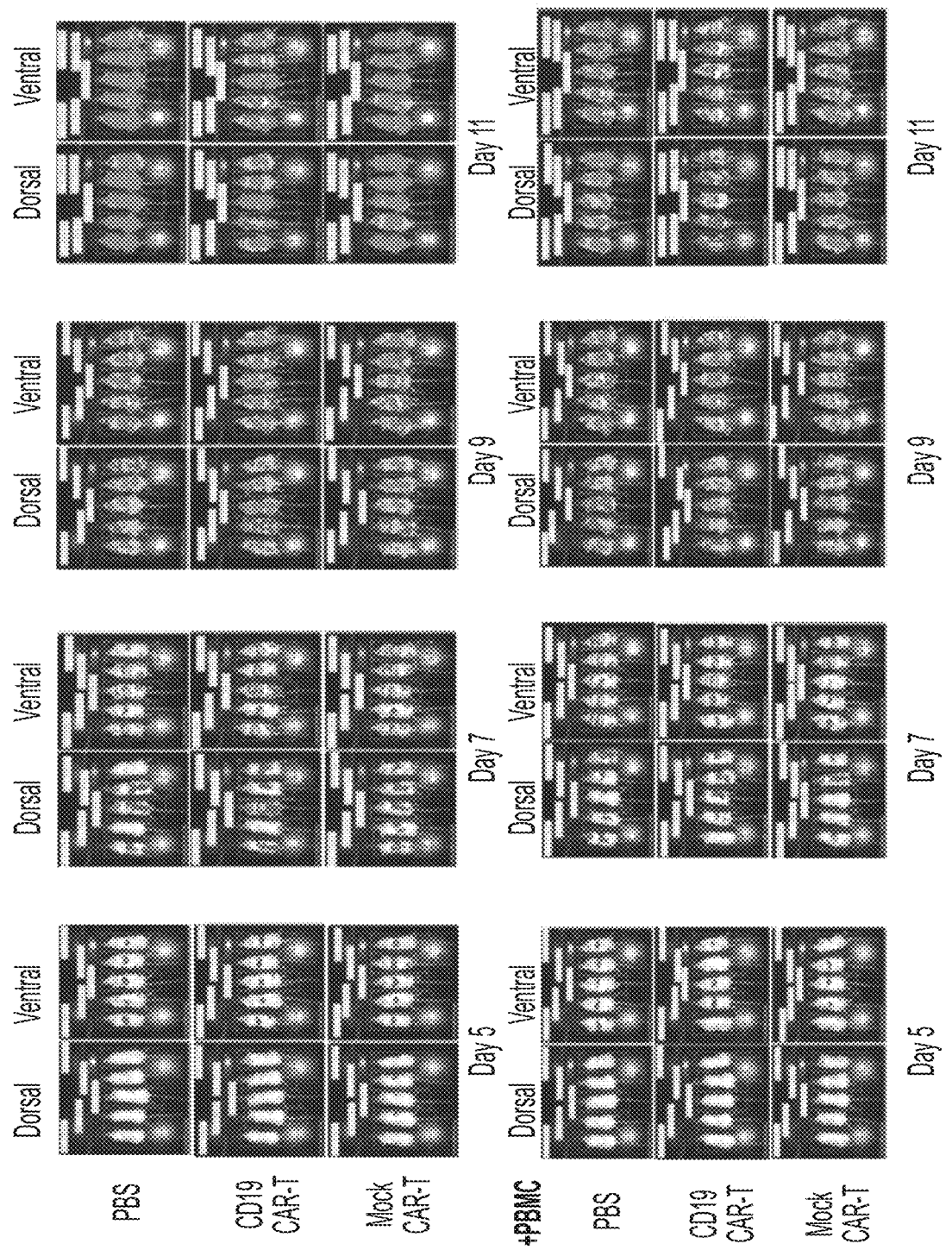

FIG. 6A provides data showing increased cytokine release from mice with a moderate tumor burden following CD19 CAR T cell/PBMC treatment compared to mice receiving CD19 CAR T cells without PBMC humanization, FIG. 6B shows an in vivo bioluminescence imaging (BLI) plot using average radiance to quantitatively measure tumor burden. FIG. 6C shows the bioluminescence images of these mice at different experiment days.

Figure 7A:
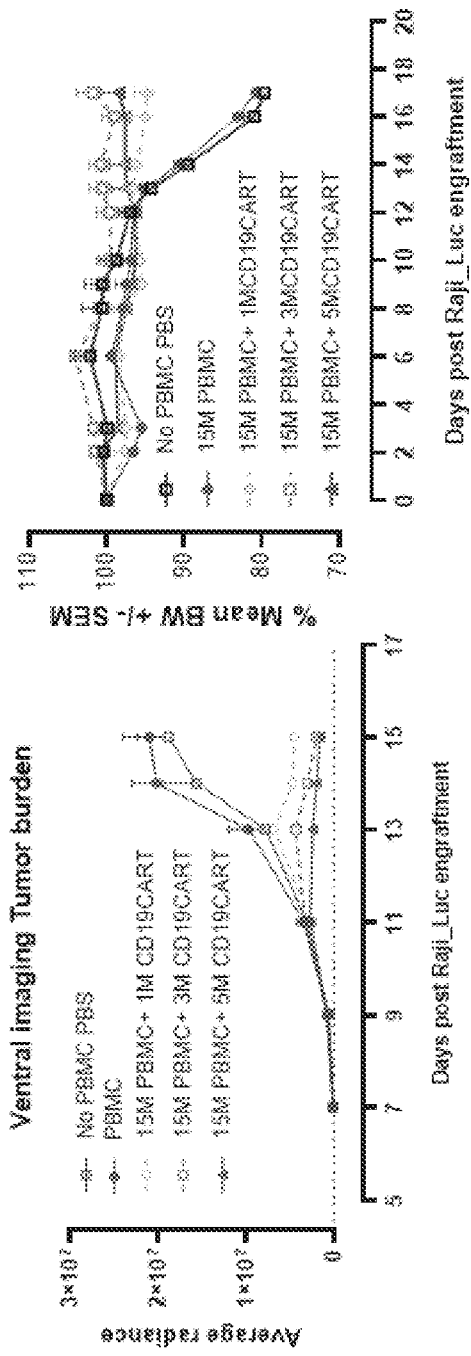
Figure 7B:
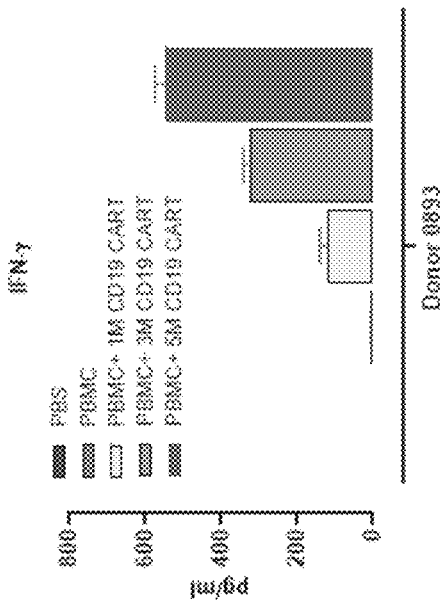

FIGS. 7A-7B are graphs showing the effect of CART dosage on tumor burden (FIG. 7A, left), mouse body weight change (FIG. 7A, right), and cytokine release (FIG. 7B).

Figures 8A, 8B:
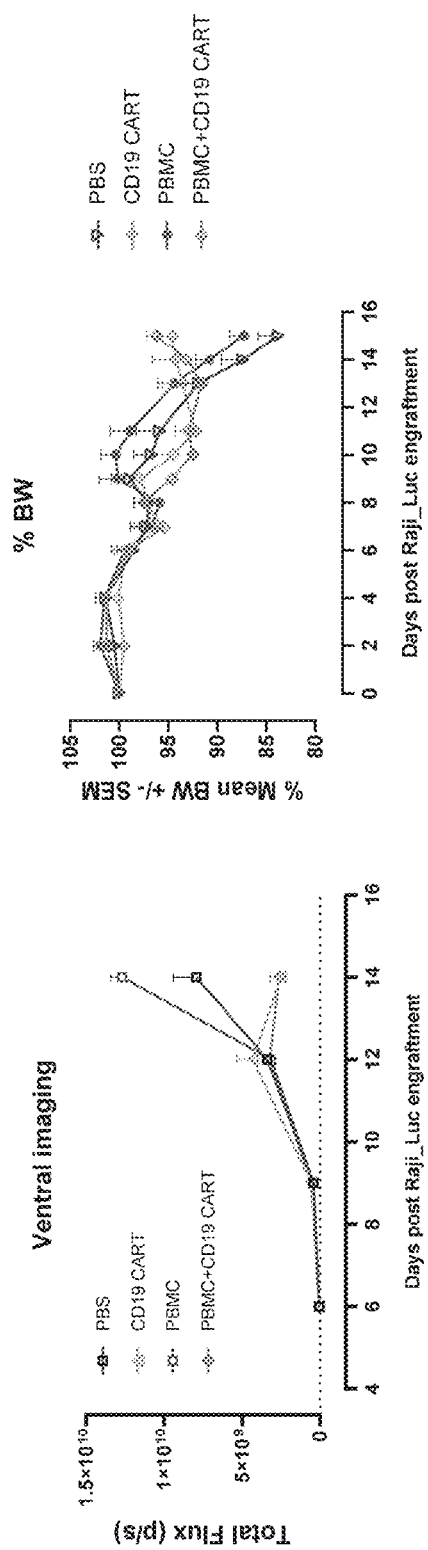
Figure 8C:
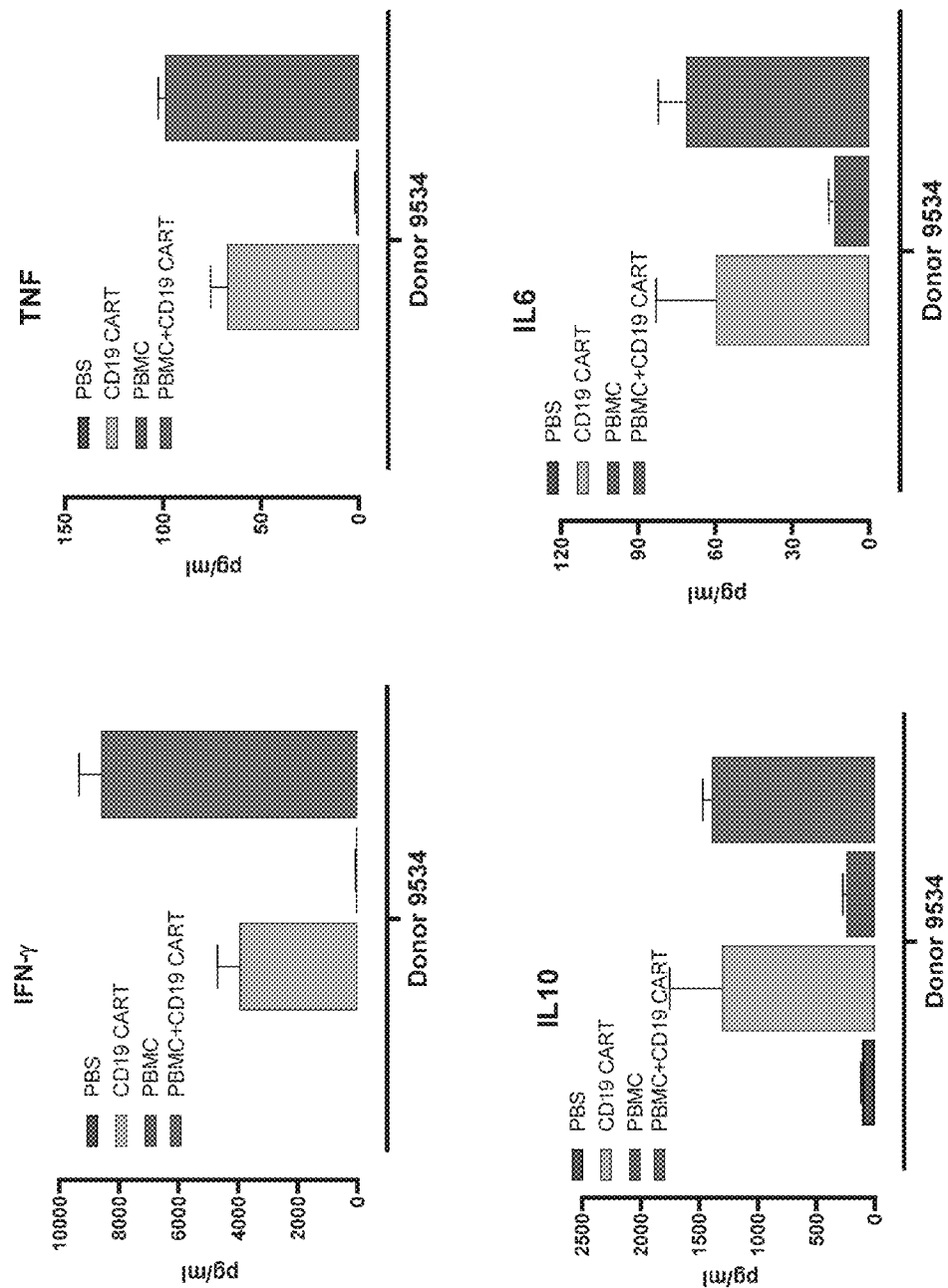

FIGS. 8A-8C are graphs showing data from CAR T cell therapy in PBMC humanized mice compared to control mice. Tumor burden (FIG. 8A), body weight (FIG. 8B), and levels of human interferon (IFN), tumor necrosis factor (TNF), interleukin-10 (IL-10), and IL-6 (FIG. 8C) are shown.

Figure 9A:
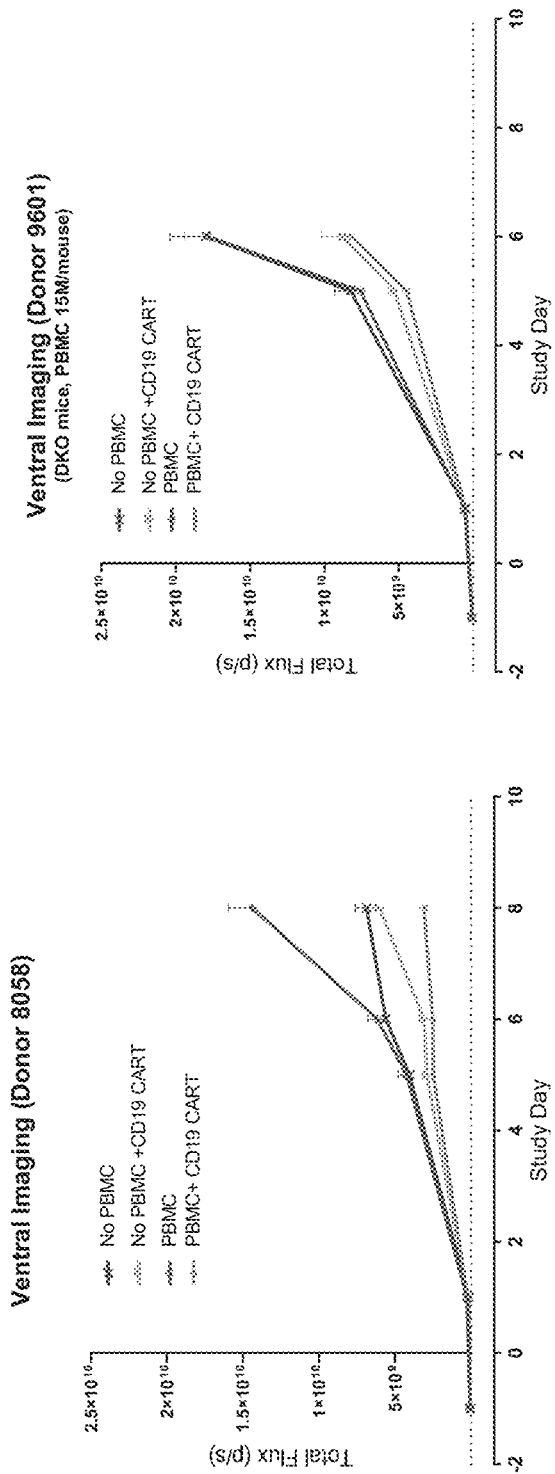
Figure 9B:
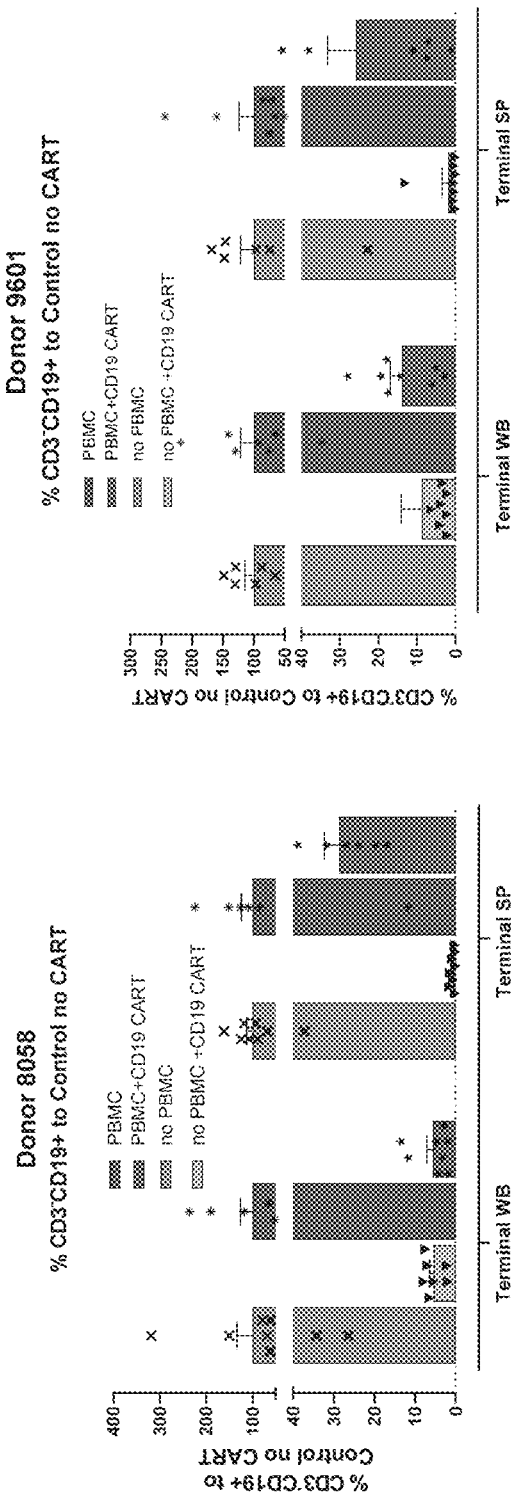
Figure 9C:
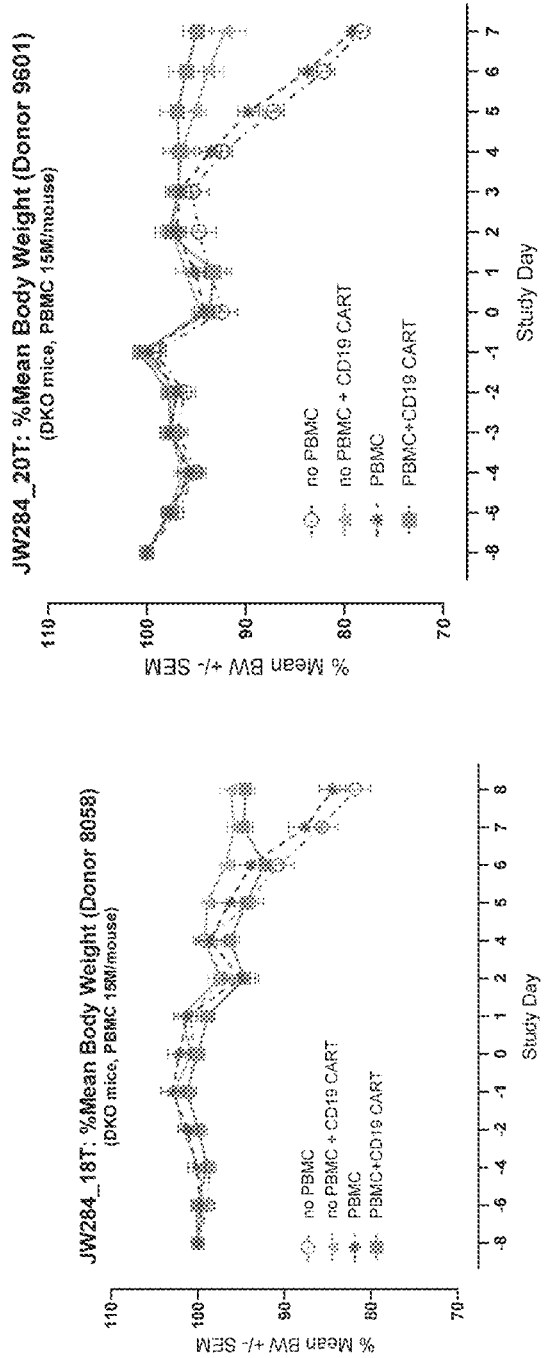

FIGS. 9A-9C are graphs showing the efficacy of allogeneic CD19 CART from different PBMC humanized mice having a Raji_Luc tumor. Tumor burden imaging (FIG. 9A), flow analysis of the CD3-CD19+ cell population (FIG. 9B), and body weight loss (FIG. 9C) are shown.

Figure 10A:
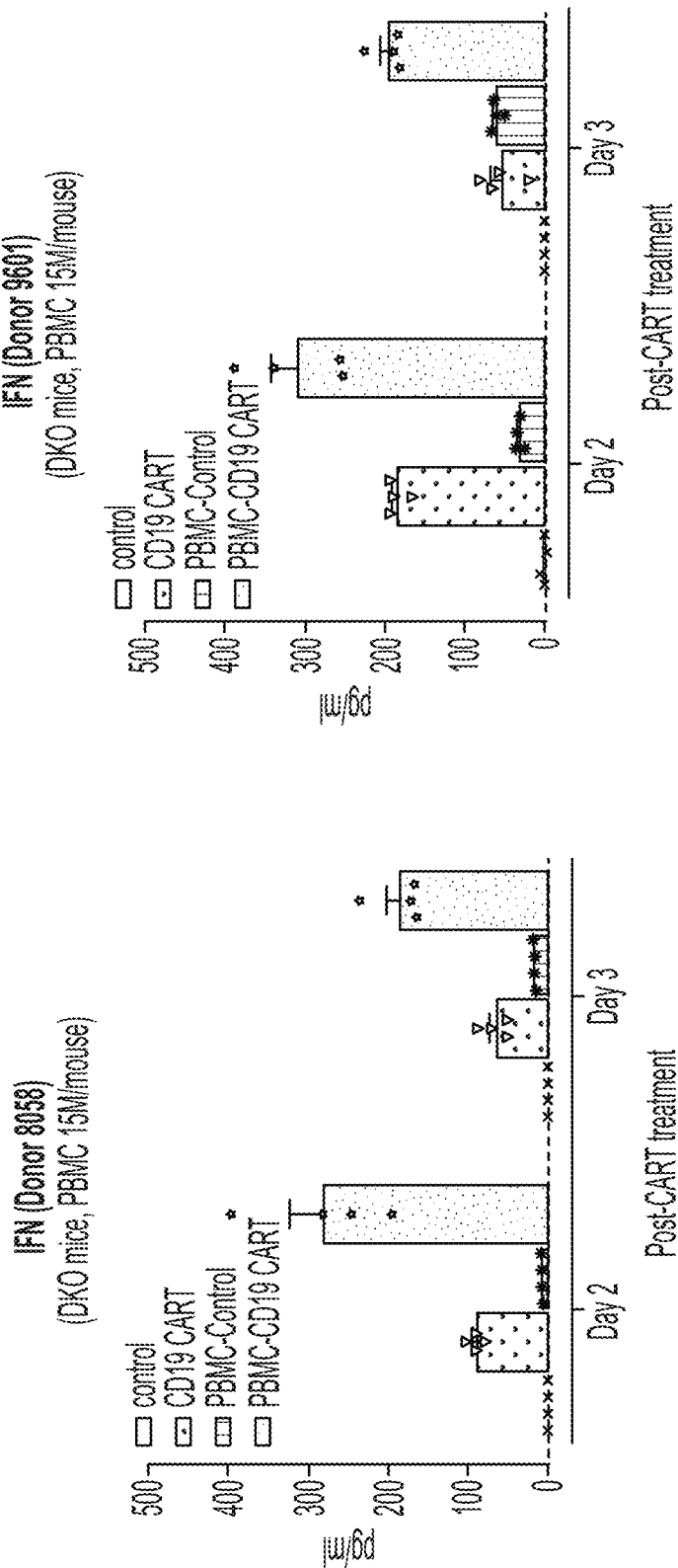
Figure 10B:
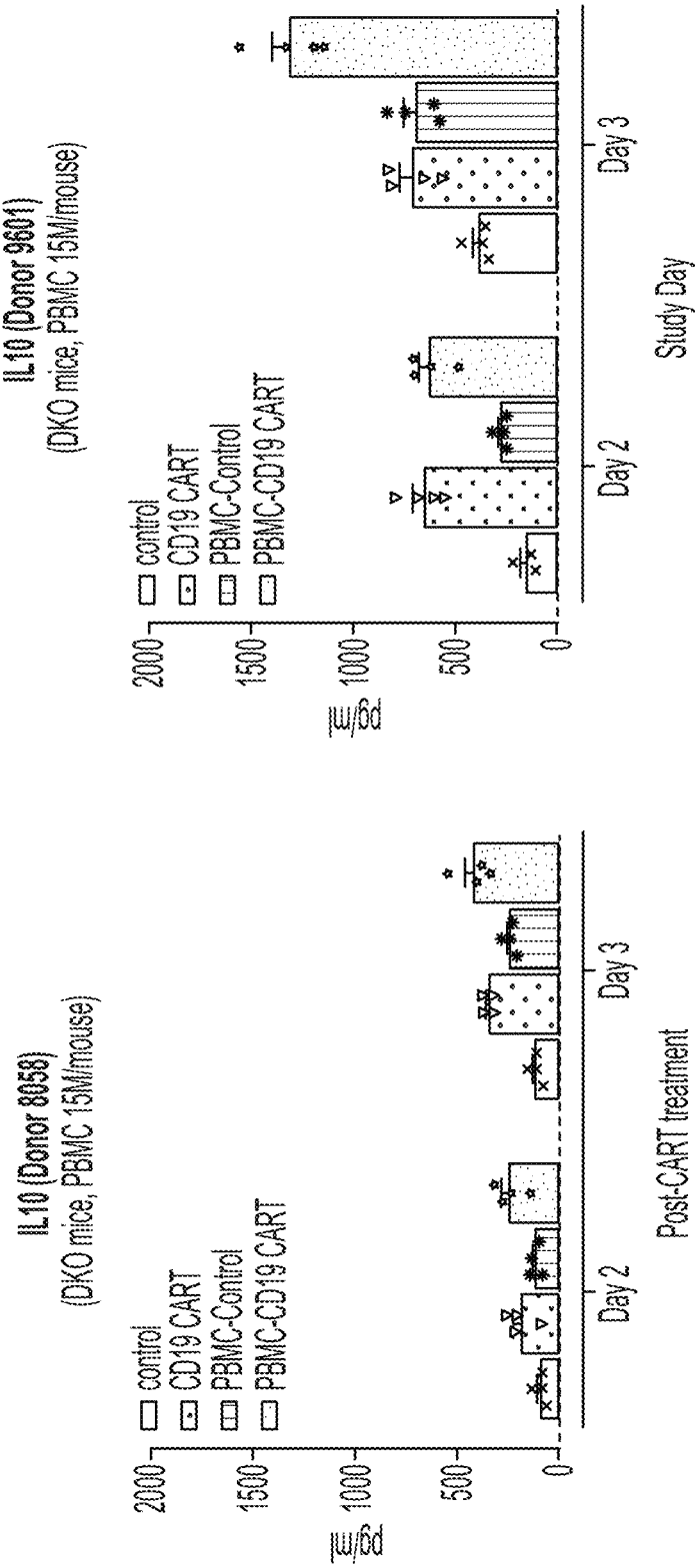
Figure 10C:
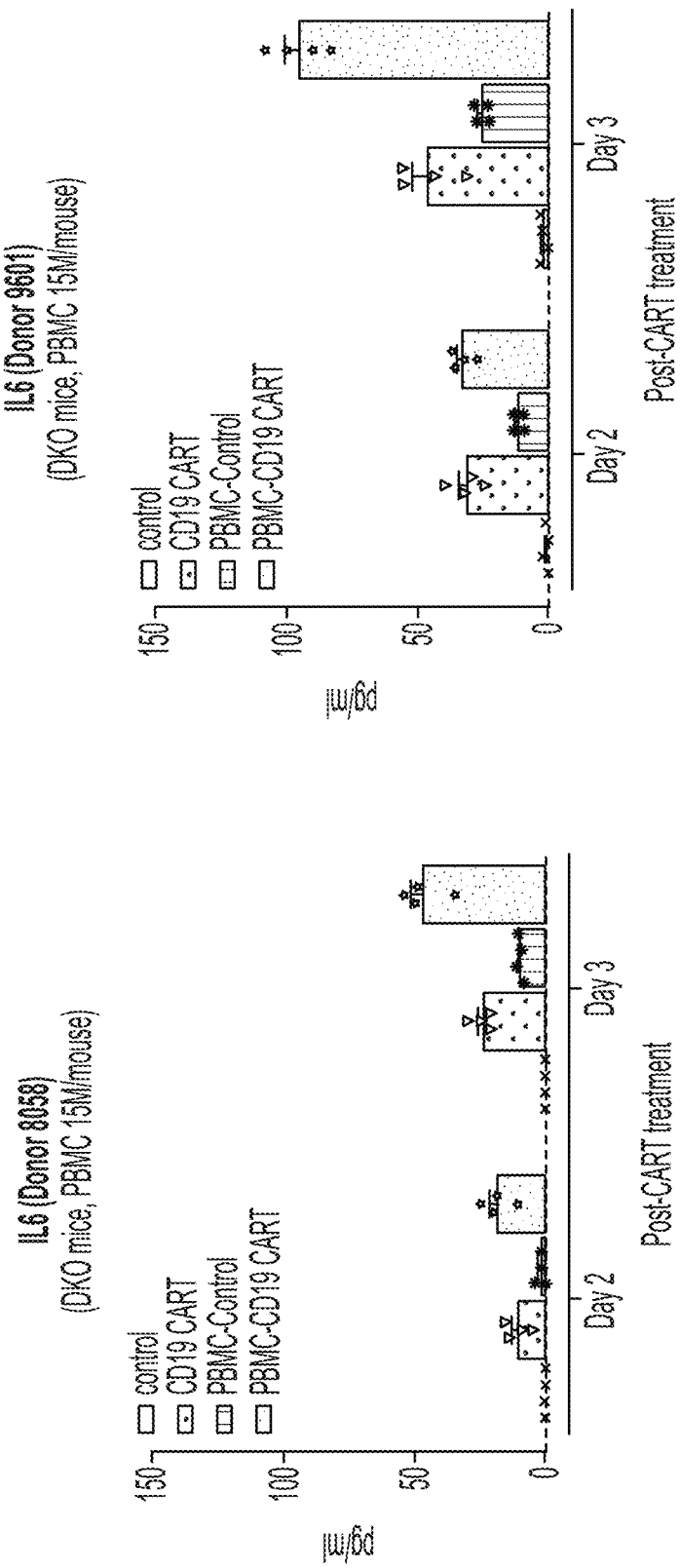

FIGS. 10A-10C are graphs showing levels of IFN (FIG. 10A), IL-10 (FIG. 10B), and IL-6 (FIG. 10C) in different PBMC humanized mice with Raji_Luc tumor following allogeneic CD19 CART treatment at two time points.

Figure 11A:
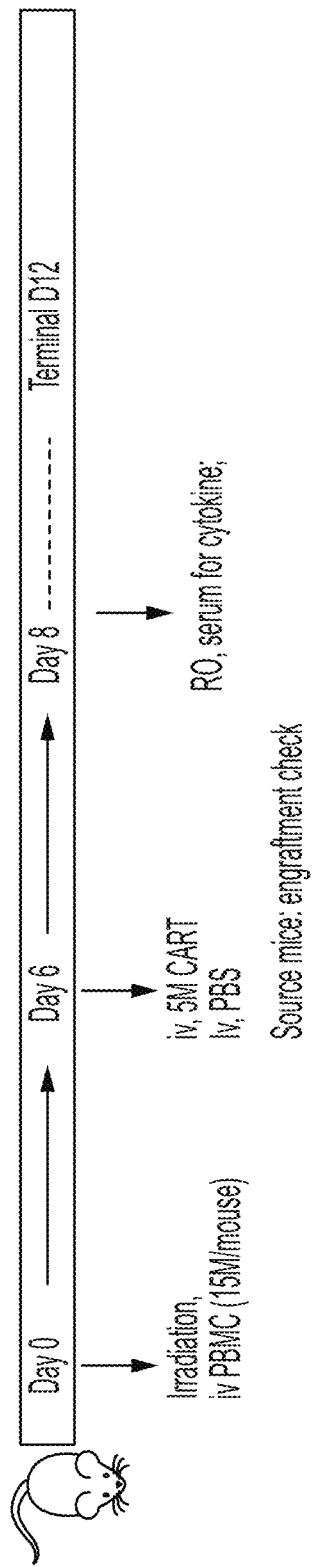
Figure 11B:
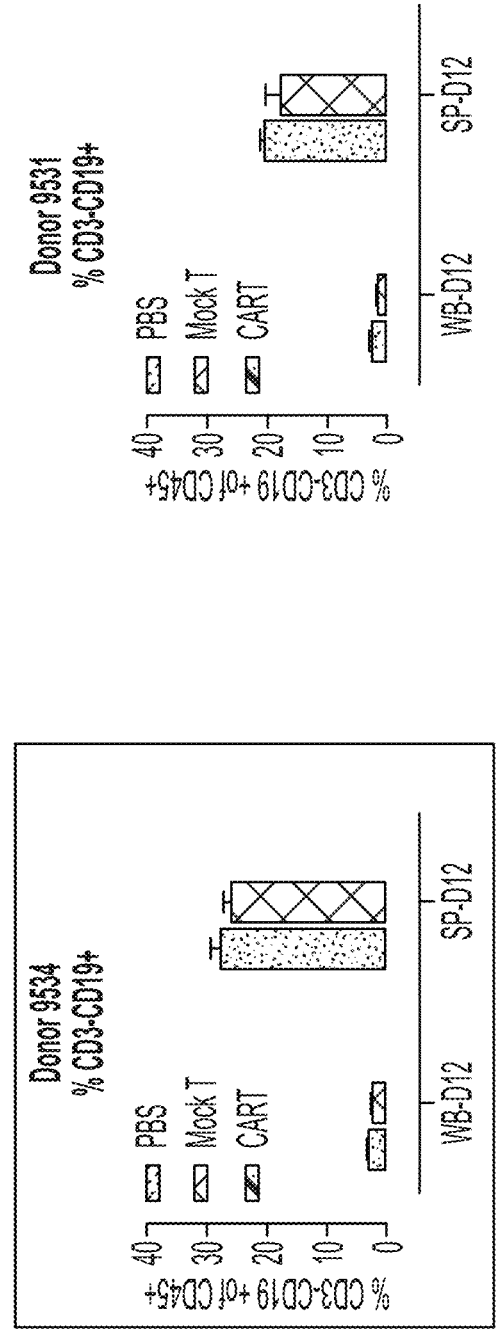

FIGS. 11A-11D show the variation of cytokine release and toxicity from different PBMC humanized mice following autologous CD19 CART treatment. The protocol is shown schematically in FIG. 11A. FIG. 11B shows the percentage of CD3-CD19+ cells after treatment. FIG. 11C shows body weight over time and FIG. 11D depicts cytokine levels following treatment.

DETAILED DESCRIPTION

Engineered immune cell therapies, such as chimeric antigen receptor (CAR) immune cell therapies and other engineered immune cell therapies, use gene transfer to reprogram immune cells (e.g., T cells, B cells, NK cells) so that they express at least one engineered antigen receptor (e.g., CAR or TCR), enabling the resulting immune cells to recognize and target cell surface antigens specific to a particular disease (e.g., cancer) or cell type. For example, CAR T cells eliminate malignant cells after recognizing and binding to them. In this way, engineered immune cell (e.g., T cell, B cell, or NK cell) therapy is used to treat hematological malignancies and is currently being developed to treat solid tumor cancers. Similarly, engineered immune cells can be used to target (e.g., bind to) cell surface antigens specific to diseased cells (e.g., those associated with cardiovascular disease, metabolic disease, or other pathological states).

Engineered immune cell therapies, such as engineered T cell therapies, have several known side effects, such as cytokine release syndrome (CRS) and T cell-related encephalopathy syndrome (neurotoxicity). Either or both complications can lead to significant morbidity and mortality.

An additional or alternative cancer immunotherapy includes the use of CARs used to reprogram natural killer cells. CAR natural killer cell (CAR NK) therapy can be an off-the-shelf (e.g., universal) therapy, as NK cells do not require strict human leukocyte antigen (HLA) matching or carry the risk of graft-versus-host disease. CAR NK therapy is developing, as primary NK cell isolation, expansion, and transduction are still being refined.

Other immune cells, such as B cells, dendritic cells, monocytes/macrophages, and neutrophils, may also be reprogramed to express at least one engineered antigen receptor (e.g., CAR or TCR).

The mouse models described herein may be used to assess whether a particular engineered immune cell (e.g., CAR or TCR immune cell (e.g., T cell, B cell, NK cell)) therapy is likely to be associated with CRS or other side effects. The mouse models described herein are humanized and therefore include human immune cells (e.g., T cells, monocytes, and NK cells) which may contribute to cytokine release. In this way, the mouse models described herein more precisely represent in vivo CRS induction and enable a more accurate assessment of human cytokine release. The mouse models described herein are also useful for identifying agents effective for treating CRS without interfering with the therapeutic efficacy of the engineered immune cells, such as immune cells expressing a CAR (the therapeutic effects of which are often mediated by the release of cytokines). Likewise, the mouse models describe herein may be used to identify engineered immune cells (e.g., CAR immune cells, e.g., which CAR constructs, are effective for treating certain diseases (e.g., cancers) without inducing CRS.

Engineered Immune Cell Therapies

In some embodiments, the human immune cell comprises an engineered receptor that specifically binds to a cell surface antigen on a diseased human cell. In some embodiments, the human immune cell is one that may be used in adoptive cell therapy (ACT). As used herein "adoptive cell therapy" (ACT) refers to a cell-based immunotherapy that relates to the transfusion of autologous or allogenic immune cells, genetically modified or not, that have been expanded ex vivo prior to the transfusion. The human immune cells, in some embodiments, are engineered immune cells.

In some embodiments, the engineered receptor is an engineered T cell receptor (eTCR). As described herein, "eTCR" refers to a dimeric heterologous cell surface signaling protein forming an alpha-beta or gamma-delta receptor typically involved in recognizing an antigen presented by a major histocompatibility complex (MHC) molecule (i.e., antigen recognition in the context of an MHC molecule). This differs from CAR T cell therapy, in which antibody fragments that bind to specific surface antigens of cancer cells are used. In some embodiments, eTCRs are modified to target or recognize histocompatibility antigen 1 (HA1), Wilms tumor 1 (WT1), cytomegalovirus (CMV), melanoma antigen (MAGE), glycoprotein 100 (gp100), MAR-1, human papillomavirus-16 E6 protein (HPV-16 E6), New York esophageal squamous cell carcinoma (NY-ESO-1), hepatitis B virus (HBV), protein 53 (P53), carcinoembryonic antigen (CEA), HPV E7, HIVgag-specific peptide SLYNTVATL (SL9), transforming growth factor-beta 2 (TGFβ2), monocyte chemotactic protein (MCPγV), TNF-related apoptosis-inducing ligand (TRAIL), preferentially expressed antigen in melanoma (PRAME), Epstein-Barr virus (EBV), or Kirsten rat sarcoma virus (KRAS) (Zhao et al., Front.

Immunol., 11 Oct. 2019). In some embodiments, the human immune cell is a T cell with an eTCR.

In some embodiments, the human immune cell comprises an engineered tumor-infiltrating lymphocyte (TIL). In TIL therapy (or engineered TIL therapy, eTIL therapy), TILs are removed from a subject's tumor (e.g., during a biopsy or surgical resection) and grown and expanded ex vivo with interleukin-2 (IL-2) and/or other cytokines. The TILs, which are naturally present in some tumors and are capable of recognizing and killing cancer cells, are then administered to the subject (e.g., by infusion). In some embodiments, the TILs are engineered TILs (eTILs), which have been modified to increase tumor homing ability, cytotoxicity and/or to improve longevity (prevent exhaustion) (Jimenez-Reinoso et al., Front. Oncol., 16 Feb. 2021). For example, in some embodiments, the eTILs may be transfected with TRAIL, IL-12, CXCL8, and/or CXCR2.

In some embodiments, the human immune cell is a regulatory T cell (Treg). As used herein, a "regulatory T cell" (Treg), also known as a suppressor T cell, is a subpopulation of T cells that modulate the immune system, maintain tolerance to self-antigens, and prevent autoimmune disease. Tregs are $CD4^+CD25^+$ $FoxP3^+$, immunosuppressive and generally suppress or downregulate induction and proliferation of T effector cells. In some embodiments, administration of the Tregs may treat or prevent cancer. For example, it has been found that administration of Tregs downregulates inflammation, blocking the development of bacteria-triggered colitis and colorectal cancer (Poutahidis et al., Carcinogenesis. 2007 Dec.; 28(12):2614-23. doi: 10.1093/carcin/bgm180. Epub 2007 Aug. 27). In some embodiments, the Tregs comprise a chimeric antigen receptor (CAR) as described below (Mohseni et al., Front. Immunol., 24 Jul. 2020). It should be understood that while many embodiments describe herein are directed to assessing the effects of cell therapies for treating cancer, the disclosure is not so limited. The mouse models described herein may be used to assess a myriad of engineered immune cell therapies, particularly those associated with the induction of CRS. Thus, in some embodiments, the human immune cells are human T cells. In some embodiments, the human immune cells are human B cells. In some embodiments, the human immune cells are human NK cells. In some embodiments, the human immune cells are human CAR T cells (e.g., a CD8+ or a CD4+ T cell). In some embodiments, the human immune cells are human CAR B cells. In some embodiments, the human immune cells are human CAR NK cells. In some embodiments, the human immune cells are human eTCR T cells. In some embodiments, the human immune cells are human eTILs. In some embodiments, the human immune cells are human eTregs. Any one or more of the human immune cells may comprise an engineered receptor that specifically binds to a cell surface antigen on diseased human cells (e.g., cancer cells, or other cells associated with cardiovascular disease, metabolic disease, or other pathological states).

Chimeric Antigen Receptor (CAR) Immune Cell Therapies

A "chimeric antigen receptor" refers to an artificial immune cell receptor that is engineered to recognize and bind to an antigen expressed by diseased cells (e.g., tumor cells). Generally, a CAR is designed for a T cell and is a chimera of a signaling domain of the T cell receptor (TcR) complex and an antigen-recognizing domain (e.g., a single chain fragment (scFv) of an antibody or other antibody fragment) (Enblad et al., Human Gene Therapy. 2015; 26(8):498-505). A T cell that expresses a CAR is referred to as a "CAR T cell." In some embodiments, the T cell is a Treg ($CD4^+CD25^+$ $FoxP3^+$) and resulting CAR T cell is referred to as a "CAR Treg cell."

There are five generations of CARs, each of which contains different components. First generation CARs join an antibody-derived scFv to the CD3zeta ($\zeta$ or z) intracellular signaling domain of the T cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TcR CD3-$\zeta$ chain. Third-generation costimulatory domains may include, e.g., a combination of CD3z, CD27, CD28, 4-1BB, ICOS, or OX40. CARs, in some embodiments, contain an ectodomain (e.g., CD3$\zeta$), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., Blood. 2015; 125(26):4017-4023; Kakarla and Gottschalk, Cancer J. 2014; 20(2):151-155).

In some embodiments, the chimeric antigen receptor (CAR) is a T cell redirected for universal cytokine killing (TRUCK), also known as a fourth generation CAR. TRUCKs are CAR-redirected T cells used as vehicles to produce and release a transgenic cytokine, IL-12, that accumulates in the targeted tissue, e.g., a targeted tumor tissue. The transgenic cytokine is released upon CAR engagement of the target. This may result in therapeutic concentrations at the targeted site and avoid systemic toxicity.

In some embodiments, the CAR T cell is a fifth generation CAR or next-generation CAR. Fifth generation CAR T cells are based on second generation CARs, having additional intracellular domains of cytokine receptors. In some embodiments, the additional intracellular domain is a cytoplasmic IL-2 receptor (e.g., IL-2R$\beta$ having a STAT3/5 binding motif), which is a binding site for STAT3/5, a transcription factor (Tokarew et al., British Journal of Cancer. 2019; 120: 26-37). By including the binding site, the CAR is capable of producing all three synergistic signals necessary to physiologically to drive full T cell activation and proliferation: TCR (through the CD3$\zeta$ domains), co-stimulatory (CD28 domain), and cytokine (JAK-STAT3/5) signaling.

CARs typically differ in their functional properties. The CD3$\zeta$ signaling domain of the T cell receptor, when engaged, will activate and induce proliferation of T cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T cells. Similar antitumor effects are observed in vitro with CD28 or 4-1BB CARs, but preclinical in vivo studies suggest that 4-1BB CARs may produce superior proliferation and/or persistence. Clinical trials suggest that both of these second-generation CARs are capable of inducing substantial T cell proliferation in vivo, but CARs containing the 4-1BB costimulatory domain appear to persist longer. Third generation CARs combine multiple signaling domains (costimulatory) to augment potency. Fourth generation CARs are additionally modified with a constitutive or inducible expression cassette for a transgenic cytokine, which is released by the CAR T cell to modulate the T cell response. See, for example, Enblad et al., Human Gene Therapy. 2015;

26(8):498-505; Chmielewski and Hinrich, *Expert Opinion on Biological Therapy.* 2015; 15(8): 1145-1154. As noted above, fifth generation CARs further comprise cytokine receptor domains and are able to trigger cytokine signaling, further enhancing T cell proliferation and maintenance (Tokarew et al., *British Journal of Cancer.* 2019; 120: 26-37).

Other immune cells may be reprogramed using CAR technology. For example, NK cells, B cells, dendritic cells, monocytes/macrophages, and neutrophils may also be reprogramed to expression at least one CAR.

NK cells are derived from the bone marrow and defend against viruses and prevent cancer. These cells can kill cells (e.g., virus-infected cells) by injecting a combination of chemicals lethal to the cell. They have been investigated for cancer immunotherapy (Xie et al., *EBioMedicine,* 2020, 59: 102975; Wang et al., *Cancer Letters,* 2020, 472:175-180; Pfefferle et al., *Cancers* (Basal), 2020, 12(3): 76: Habib et al., *Ochsner Journal,* 2019, 19(3): 186-187).

B cells (B-lymphocytes) are immune cells that develop in the bone marrow from hematopoietic stem cells and produce antibodies. B cells are "trained" so that they do not produce antibodies against healthy tissue, and when they encounter foreign (non-self) material, they mature into plasma cells or memory cells.

Dendritic cells are antigen-presenting cells that process antigen material and present it on their respective cell surfaces to T cells. In this way, they act as a liaison between the innate and adaptive immune systems. CAR dendritic cells (CAR-DC) have been used in conjunction with CAR T cells to improve anti-cancer cytotoxicity (Suh et al., *Journal of Clinical Oncology,* 2018, 35(7): 144).

Monocytes (macrophages) are phagocytic cells of the immune system found in all tissues. They play a role in both adaptive and innate immunity, and in some instances, work with T cells to kill microorganisms. CAR macrophages (CAR-M) have been shown to reduce or eliminate tumor cells in an ovarian cancer cell line (Klichinsky et al., *Nature Biotechnology,* 2020, 38: 947-53).

Neutrophils (polymorphonuclear leukocytes, granulocytes) also develop in the bone marrow, and leave the blood stream to accumulate in infected tissues. Typically, during the acute phase of an infection, a neutrophil will migrate to the site of inflammation, where they ingest organisms to kill them.

In some embodiments, the engineered immune cell (e.g., T cell, B cell, or NK cell) therapy is autologous; that is, for example, a subject's T cells are collected and used to generate the CAR T cells that are later used to treat the subject.

In some embodiments, the engineered immune cells are universal allogeneic engineered immune cells (e.g., "off-the-shelf" engineered immune cells). Allogeneic engineered immune cells use donor immune cells; that is, immune cells from a source other than the subject (recipient) who undergoes the engineered immune cell (e.g., T cell, B cell, or NK cell) therapy. In some embodiments, the donor immune cells are from a healthy human (e.g., adult or child). Allogeneic engineered immune cells (e.g., CAR T cells) can cause graft-versus-host disease (GVHD) in a subject after administration, for example, if the engineered immune cell recognizes cell surface HLA class I and class II molecules on the subject's cells as "non-self" and attacks them. In order to circumvent this issue with respect to T cells, the T cell αβ receptor (TCRαβ) of the CAR T cell may be knocked out using gene editing tools (e.g., zinc finger nucleases, transcription activator like effector nucleases, or clustered regularly interspaced short palindromic repeats (CRISPR)/CRISPR-associated protein 9 (Cas9)) (Kim et al., *Biomolecules.* 2020; 10(2):263). In this way, universal allogeneic CAR T cells may be administered to any subject (recipient).

In some embodiments, a chimeric antigen receptor (CAR) comprises an extracellular domain comprising an antigen binding domain, a transmembrane domain, and a cytoplasmic domain. In some embodiments, a CAR is fully human. In some embodiments, the antigen binding domain of a CAR is specific for one or more antigens. In some embodiments, a "spacer" domain or "hinge" domain is located between an extracellular domain (comprising the antigen binding domain) and a transmembrane domain of a CAR, or between a cytoplasmic domain and a transmembrane domain of the CAR. A "spacer domain" refers to any oligopeptide or polypeptide that functions to link the transmembrane domain to the extracellular domain and/or the cytoplasmic domain in the polypeptide chain. A "hinge domain" refers to any oligopeptide or polypeptide that functions to provide flexibility to the CAR, or domains thereof, or to prevent steric hindrance of the CAR, or domains thereof. In some embodiments, a spacer domain or hinge domain may comprise up to 300 amino acids (e.g., 10 to 100 amino acids, or 5 to 20 amino acids). In some embodiments, one or more spacer domain(s) may be included in other regions of a CAR.

In some embodiments, a CAR of the disclosure comprises an antigen binding domain, such as a single chain Fv (scFv) specific for an antigen (e.g., a tumor antigen). The choice of binding domain depends upon the type and number of ligands that define the surface of a target cell. For example, the antigen binding domain may be chosen to recognize a ligand that acts as a cell surface marker on target cells associated with a particular disease state, such as cancer, cardiovascular disease, metabolic disease, neurobiological disease, or an autoimmune disease. Thus, examples of cell surface markers that may act as ligands for the antigen binding domain in the CAR of the present disclosure include those associated with cancer cells and/or other forms of diseased cells. In some embodiments, a CAR is engineered to target a tumor antigen of interest by way of engineering a desired antigen binding domain that specifically binds to a surface antigen of an Epstein-Barr virus (EBV) or papillomavirus particle.

An antigen binding domain (e.g., an scFv) that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antigen binding domain (e.g., an scFv) that specifically binds to a first target antigen may or may not specifically bind to a second target antigen. As such, "specific binding" does not necessarily require (although it can include) exclusive binding.

In some embodiments, immune cells expressing a CAR are genetically modified to recognize multiple targets or antigens, which permits the recognition of unique target or antigen expression patterns on diseased cells (e.g., tumor cells). Examples of CARs that can bind multiple targets include: "split signal CARs," which limit complete immune cell activation to tumors expressing multiple antigens; "tandem CARs" (TanCARs), which contain ectodomains having two scFvs; and "universal ectodomain CARs," which incorporate avidin or a fluorescein isothiocyanate (FITC)-specific scFv to recognize tumor cells that have been incubated with tagged monoclonal antibodies (mAbs).

In some embodiments, the target is CD19; that is, the CAR is a CD19 CAR. In some embodiments, the target is CD22; that is, the CAR is a CD22 CAR. In some embodiments, the target is CD123; that is, the CAR is a CD123 CAR. Other targets include, but are not limited to CD20, B cell maturation antigen (BCMA), C-type lectin-like molecule-1 (CLL-1), tyrosine-protein kinase transmembrane receptor 1 (ROR-1), IL13Rα2, CD20, CD138, CD33, prostate specific membrane antigen (PSMA), CD171, epidermal growth factor receptor variant III (EGFRvIII), fibroblast activation protein (FAP), folate receptor (FR), glypican-3, human epidermal growth factor receptor 2 (HER2), mucin 1, cell surface associated (MUC1), mesothelin, and natural killer group 2D (NKG2D). In some embodiments, the CAR is specific to any target or antigen of interest that is found on the surface of a cancer cell. In other embodiments, the CAR is specific to any target or antigen of interest that is found on the surface of a diseased cell.

A CAR is considered "bispecific" if it recognizes two distinct antigens (has two distinct antigen recognition domains). In some embodiments, a bispecific CAR is comprised of two distinct antigen recognition domains present in tandem on a single transgenic receptor (referred to as a TanCAR; see, e.g., Grada Z et al. *Molecular Therapy Nucleic Acids* 2013; 2:e105, incorporated herein by reference).

In some embodiments, a CAR is an antigen-specific inhibitory CAR (iCAR), which may be used, for example, to avoid off-tumor toxicity (Fedorov, V D et al. *Sci. Transl. Med.* published online Dec. 11, 2013, incorporated herein by reference). iCARs contain an antigen-specific inhibitory receptor, for example, to block nonspecific immunosuppression, which may result from extratumor target expression. iCARs may be based, for example, on inhibitory molecules CTLA-4 or PD-1, to block immunosuppression, or on a pan-leukocyte antigen, such as CD52, to block leukocyte destruction. In some embodiments, these iCARs block T cell responses from T cells activated by either their endogenous T cell receptor or an activating CAR.

In some embodiments, CARs are engineered for use in adoptive cell transfer, wherein immune cells are removed from a subject and modified so that they express receptors specific to an antigen, e.g., a tumor-specific antigen. The modified immune cells, which may then recognize and kill the cancer cells, are reintroduced into the subject (Pule, et al., *Cytotherapy.* 2003; 5(3): 211-226; Maude et al., *Blood.* 2015; 125(26): 4017-4023, each of which is incorporated herein by reference).

Cytokine Release Syndrome

Cytokine release syndrome (CRS) occurs with activation of T cells and Natural Killer (NK) cells as well as other immune cell populations (e.g., macrophages). With the addition of engineered immune cells (e.g., T cells, B cells, or NK cells), the activation of immune cells can lead to the release of high levels of cytokines and downstream injury and possibly death. Both T cells and NK cells have been found to be sources of CRS in response to certain immunomodulators (Wing M. G. et al. (1995) Ther. Immunol. 2:183-190; Carson W. E., (1999) *J Immunol* 162; 4943-4951). With different immunomodulators and the activation of various immune cell populations, CRS can manifest with high levels of cytokine release that can vary with the various activated immune cell populations.

The main cytokines associated with pathogenesis of CRS include interleukin-6 (IL-6), interleukin-10 (IL-10), interferon (IFN)-γ, monocyte chemoattractant protein 1 (MCP-1) and granulocyte-macrophage colony-stimulating factor (GM-CSF). Several other cytokines, including TNF, IL1, IL2, IL-2-receptor-a, and IL8 have also been associated with CRS. Several factors contributing to CRS toxicity in cancer patients, particularly those undergoing engineered immune cell (e.g., T cell, B cell, or NK cell) therapy include: the structure of the CAR, high tumor burden, higher immune cell infusion dose, and other patient-specific factors such as pre-existent state of inflammation and baseline endothelial activation.

One approach for preventing life-threatening high-grade CRS toxicity is to administer an anti-cytokine therapy early in CRS development (e.g., when a subject first exhibits symptoms of CRS). Tocilizumab (an IL6 antagonist), for example, has been approved by U.S. Food and Drug Administration (FDA) for the treatment of severe or life-threatening CAR T cell-induced CRS. Other treatments for CAR T cell-induced CRS include anti-IL-6 antibodies (e.g., siltuximab), corticosteroids (e.g., methylprednisone), anti-TNF-α drugs (e.g., etanercept), IL-1R inhibitors (e.g., anakinra), GM-CSF inhibitors, and small molecule inhibitors (e.g., ruxolitinib (JAK 1/2 inhibitor) and Bruton's tyrosine kinase inhibitor). In some embodiments, the mouse models provided herein are used to assess the therapeutic efficacy and/or side effects associated with candidate CRS treatments, for example, in subjects undergoing engineered immune cell (e.g., T cell, B cell, or NK cell) therapy, as described in more detail elsewhere herein.

Immunodeficient Mouse Models

Provided herein, in some embodiments, are immunodeficient mouse models. As is known in the art, immunodeficient mice have impaired or disrupted immune systems, such as specific deficiencies in MHC class I, II or both, B cell or T cell defects, or defects in both, as well as immunodeficiency due to knockdown of genes for cytokines, cytokine receptors, TLR receptors and a variety of transducers and transcription factors of signaling pathways. Immunodeficiency mouse models include the single-gene mutation models such as nude-mice (nu) strains and the severe combined immunodeficiency (scid) strains, non-obese diabetic (NOD) strain, RAG (recombination activating gene) strains with targeted gene deletion and a variety of hybrids originated by crossing doubly and triple mutation mice strains with additional defects in innate and adaptive immunity.

Non-limiting examples of spontaneous and transgenic immunodeficient mouse models include the following mouse strains:

Nude (nu) [Flanagan S P. Genet Res 1966; 8: 295-309; and Nehls M et al. *Nature* 1994; 372: 103-7];

Scid (scid) [Bosma G C et al. *Nature* 1983; 301:527-30; Mosier D E et al. *Nature* 1988; 335: 256-9; and Greiner D L et al. *Stem Cells* 1998; 16: 166-77];

NOD [Kikutani H et al. *Adv Immunol* 1992; 51: 285-322; and Anderson M S et al. *Ann Rev Immunol* 2005; 23: 447-85];

RAG1 and RAG2 (rag) [Mombaerts P et al. *Cell* 1992; 68: 869-77; Shinkai U et al. *Cell* 1992; 68: 855-67];

NOD-scid [Greiner D L et al. 1998; Shultz L D et al. *J Immunol* 1995; 154: 180-91; Melkus M W et al. *Nature Med* 2006; 12: 1316-22; and Denton P W et al. *PLoS Med* 2008; 4(12): e357];

IL2rgnull [DiSanto J P et al. *Proc Natl Acad Sci USA* 1995; 92: 377-81];

B2mnull [Christianson S W et al. *J Immunol* 1997; 158: 3578-86];

NOD-scid IL2rγnull [Shultz L D et al. *Nat Rev Immunol* 2007; 7: 118-30; Ito M et al. *Blood* 2002; 100: 3175-82; Ishikawa I et al. *Blood* 2005; 106: 1565-73; and Macchiarini F et al. *J Exp Med* 2005; 202: 1307-11];

NOD-scid B2mnull [Shultz et al. 2007; Shultz L D et al. *Transplantation* 2003; 76: 1036-42; Islas-Ohlmayer M A et al. *J Virol* 2004; 78:13891-900; and Macchiarini et al. 2005]; and HLA transgenic mice [Grusby M J et al. *Proc Natl Acad Sci USA* 1993; 90(9): 3913-7; and Roy C J et al. *Infect Immun* 2005; 73(4): 2452-60]. See, e.g., Belizario J E *The Open Immunology Journal,* 2009; 2:79-85.

NSG-HLA-A2/HHD (Leonard D. Shultz et al. *Proc Natl Acad Sci USA* 2010; 107(29): 13022-27).

NSG-Tg(Hu-IL15)

In some embodiments, an immunodeficient mouse has a NOD (non-obese diabetic) genotype. The NOD mouse (e.g., the NOD/ShiLtJ mouse, Jackson Labs Stock #001976) is a polygenic model for autoimmune type 1 diabetes, characterized by hyperglycemia and insulitis, a leukocytic infiltration of the pancreatic islet cells. The NOD mice are hypoinsulinemic and hyperglucagonemic, indicating a selective destruction of pancreatic islet beta cells. The major component of diabetes susceptibility in NOD mice is the unique MHC haplotype. NOD mice also exhibit multiple aberrant immunophenotypes including defective antigen presenting cell immunoregulatory functions, defects in the regulation of the T lymphocyte repertoire, defective NK cell function, defective cytokine production from macrophages (Fan et al., 2004) and impaired wound healing. They also lack hemolytic complement, C5. NOD mice also are severely hard-of-hearing. A variety of mutations causing immunodeficiencies, targeted mutations in cytokine genes, as well as transgenes affecting immune functions, have been backcrossed into the NOD inbred strain background.

In some aspects of the present disclosure, an immunodeficient mouse provided herein based on the NOD background may have a genotype selected from NOD-Cg.-Prkdc$^{scid}$IL2rg$^{tm1wJl}$/SzJ (NSG), a NOD.Cg-Rag1$^{tm1Mom}$ Il2$^{tm1Wjl}$/SzJ (NRG), and NOD.Cg-Prkdc$^{scid}$Il2rg$^{tm1Sug}$/Shi-Jic. For example, the mouse may have a NOD-Cg.-Prkdc$^{scid}$IL2rg$^{tm1wJl}$/SzJ (NOG) genotype. Other immunodeficient mouse strains are contemplated herein.

In some embodiments, an immunodeficient mouse has an NSG™ genotype. The NSG™ mouse (e.g., Jackson Labs Stock No: #005557) is an immunodeficient mouse that lacks mature T cells, B cells, and natural killer (NK) cells, is deficient in multiple cytokine signaling pathways, and has many defects in innate immunity (see, e.g., (Shultz, Ishikawa, & Greiner, 2007; Shultz et al., 2005; Shultz et al., 1995), each of which is incorporated herein by reference). The NS mouse, derived from the NOD mouse strain NOD/ShiLtJ (see, e.g., (Makino et al., 1980), which is incorporated herein by reference), include the Prkdc$^{scid}$ mutation (also referred to as the "severe combined immunodeficiency" mutation or the "scid" mutation) and the Il2rg$^{tm1Wjl}$ targeted mutation. The Prkdc$^{scid}$ mutation is a loss-of-function (null) mutation in the mouse homolog of the human PRKDC gene—this mutation essentially eliminates adaptive immunity (see, e.g., (Blunt et al., 1995; Greiner, Hesselton, & Shultz, 1998), each of which is incorporated herein by reference). The Il2rg$^{tm1Wjl}$ mutation is a null mutation in the gene encoding the interleukin 2 receptor gamma chain (IL2Rγ, homologous to IL2RG in humans), which blocks NK cell differentiation, thereby removing an obstacle that prevents the efficient engraftment of primary human cells (Cao et al., 1995; Greiner et al., 1998; Shultz et al., 2005), each of which is incorporated herein by reference).

In some embodiments, an immunodeficient mouse has an NRG genotype. The NRG mouse (e.g., Jackson Labs Stock #007799) is extremely immunodeficient. This mouse two mutations on the NOD/ShiLtJ genetic background; a targeted knockout mutation in recombination activating gene 1 (Rag)) and a complete null allele of the IL2 receptor common gamma chain (IL2rg$^{null}$). The Rag1$^{null}$ mutation renders the mice B and T cell deficient and the IL2rg$^{null}$ mutation prevents cytokine signaling through multiple receptors, leading to a deficiency in functional NK cells. The severe immunodeficiency allows the mice to be humanized by engraftment of human CD34+ hematopoietic stem cells (HSC) and patient derived xenografts (PDX) at high efficiency. The immunodeficient NRG mice are more resistant to irradiation and genotoxic drugs than mice with a scid mutation in the DNA repair enzyme Prkdc.

In some embodiments, an immunodeficient mouse has an NOG genotype. The NOG mouse (Ito M et al., *Blood* 2002) is an extremely severe combined immunodeficient mouse established by combining the NOD/scid mouse and the IL-2 receptor-γ chain knockout (IL2rγKO) mouse (Ohbo K. et al., *Blood* 1996). The NOG mouse lacks T and B cells, lacks natural killer (NK) cells, exhibits reduced dendritic cell function and reduced macrophage function, and lacks complement activity.

In some embodiments, an immunodeficient mouse has an NCG genotype. The NCG mouse (e.g., Charles River Stock #572) was created by sequential CRISPR/Cas9 editing of the Prkdc and Il2rg loci in the NOD/Nju mouse, generating a mouse coisogenic to the NOD/Nju. The NOD/Nju carries a mutation in the Sirpa (SIRP α) gene that allows for engrafting of foreign hematopoietic stem cells. The Prkdc knockout generates a SCID-like phenotype lacking proper T cell and B-cell formation. The knockout of the Il2rg gene further exacerbates the SCID-like phenotype while additionally resulting in a decrease of NK cell production.

It should also be understood that standard genetic nomenclature used herein provides unique identification for different rodent strains, and the strain symbol conveys basic information about the type of strain or stock used and the genetic content of that strain. Rules for symbolizing strains and stocks have been promulgated by the International Committee on Standardized Genetic Nomenclature for Mice. The rules are available on-line from the Mouse Genome Database (MGD; informatics.jax.org) and were published in print copy (Lyon et al. 1996). Strain symbols typically include a Laboratory Registration Code (Lab Code). The registry is maintained at the Institute for Laboratory Animal Research (ILAR) at the National Academy of Sciences, Washington, D.C. Lab Codes may be obtained electronically at ILAR's web site (nas.edu/cls/ilarhome.nsf). See also Davisson M T, Genetic and Phenotypic Definition of Laboratory Mice and Rats/What Constitutes an Acceptable Genetic-Phenotypic Definition, National Research Council (US) International Committee of the Institute for Laboratory Animal Research. Washington (DC): National Academies Press (US); 1999.

Major Histocompatibility Complex Class I and H Knock-Out Mice

In some embodiments, a genetically modified immunodeficient mouse (e.g., NSG, NRG, or NOG mouse) includes a genomic modification, wherein the genomic modification renders the immunodeficient mouse deficient in major histocompatibility complex class I (MHC I) and major histocompatibility complex class II (MHC II), such that the genetically modified immunodeficient mouse lacks functional MHC I and lacks functional MHC II. In some embodiments, a genetically modified immunodeficient mouse deficient in MHC class I and MHC class II is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ (abbreviated as NSG-(K$^b$ D$^b$)$^{null}$ (IA$^{null}$) mouse, e.g., Jackson Labs Stock #025216). The NSG-(K$^b$ D$^b$)$^{null}$ (IA$^{null}$) mouse lacks functional MHC I due to a homozygous null mutation of H2-K and H2-D MHC I α protein subclasses (abbreviated (K$^b$ D$^b$)$^{null}$) and lacks functional MHC II due to a homozygous null mutation of H-2A subclass of MHC II (abbreviated as IA$^{null}$).

In some embodiments, a genetically modified immunodeficient mouse deficient in MHC class I and MHC class II is a NO D.Cg-B2 m$^{tm1Unc}$ Prkdc$^{scid}$ H2$^{dlAb1-Ea}$ Il2rg$^{tm1Wjl}$/SZj (abbreviated as NSG-B2M$^{null}$ (IA IE)$^{null}$, e.g., Jackson Labs Stock #030547) mouse. The NSG-B2M$^{null}$ (IA IE)$^{null}$ mouse lacks functional MHC I due to a homozygous null mutation of β2 microglobulin (abbreviated B2M$^{null}$). The NSG-B2M$^{null}$ (IA IE)$^{null}$ mouse lacks functional MHC II due to a homozygous null mutation of H-2A and H-2E subclasses of MHC II (abbreviated as (IA IE)$^{null}$).

In some embodiments, a genetically modified immunodeficient mouse deficient in MHC class I and MHC class II is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$ Tg (Ins2-HBEGF)6832Ugfm/Sz transgenic mouse (abbreviated as NSG-RIP-DTR (K$^b$ D$^b$)$^{null}$ (IA$^{null}$), e.g., Jackson Labs Stock #027976), which expresses the diphtheria toxin receptor under the control of the rat insulin promoter on an NSG™ background. Injection of diphtheria toxin (DT) into mice expressing the diphtheria toxin receptor under the control of the rat insulin promoter leads to mouse pancreatic beta cell death and hyperglycemia. The NSG-RIP-DTR (K$^b$ D$^b$)$^{null}$ (IA$^{null}$) strain permits the complete and specific ablation of mouse pancreatic beta cells, avoiding the broadly toxic effects of diabetogenic drugs such as streptozotocin.

Humanized Immunodeficient Mouse Models

In some embodiments, a humanized immunodeficient mouse model is used to screen an engineered immune cell (e.g., T cell, B cell, or NK cell) therapy. As used herein, the terms "humanized mouse", "humanized immune deficient mouse", "humanized immunodeficient mouse", and the plural versions thereof are used interchangeably to refer to an immunodeficient mouse humanized by engraftment with human peripheral blood mononuclear cells (PBMCs). Humanized mice are generated by starting with an immunodeficient mouse and, if necessary, depleting and/or suppressing any remaining murine immune cells (e.g., chemically or with radiation). That is, successful survival of the human immune system in the immunodeficient mice may require suppression of the mouse's immune system to prevent GVHD (graft-versus-host disease) rejections. After the immunodeficient mouse's immune system has been sufficiently suppressed, the mouse is engrafted with human cells (e.g., PBMCs). As used herein, "engraft" refers to the process of the human cells migrating to, and incorporating into, an existing tissue of interest in vivo. With respect to the humanized immunodeficient mouse, the engrafted human PBMCs provide functional mature human cells (e.g., immune cells, such as T cells or NK cells). The model has a specific time window of 4-5 weeks after engraftment before GVHD sets in. To increase the longevity of the model, double-knockout (DKO) mice lacking functional MHC I and MHC II, as described above, may be used.

Irradiation

As described above, in some embodiments, the immunodeficient mice are irradiated prior to engraftment with PBMCs. It is thought that irradiation of an immunodeficient mouse destroys mouse immune cells in peripheral blood, spleen, and bone marrow, which facilitates engraftment of human cells, such as human PBMCs (e.g., by increasing human PBMC survival factors), as well as expansion of immune cells, and ultimately, engineered immune cells (e.g., T cells, B cells, or NK cells). Irradiation also shortens the time it takes to accumulate the required number of human immune cells to "humanize" the mouse models.

For immunodeficient mice (e.g., NSG™ mice), this preparation is commonly accomplished through whole-body gamma irradiation. Irradiators may vary in size depending on their intended use. Animals are generally irradiated for short periods of time (less than 15 min). The amount of time spent inside the irradiator varies depending on the radioisotope decay charts, amount of irradiation needed, and source of ionizing energy (that is, X-rays versus gamma rays, for which a cesium or cobalt source is needed).

A myeloablative irradiation dose is usually 700 to 1300 cGy, though in some embodiments, lower doses such as 1-100 cGy (e.g., about 2, 5, or 10 cGy), or 300-700 cGy may be used.

As an example, the mouse is irradiated with 100 cGy X-ray (or 75 cGy-125 cGy X-ray). In some embodiments, the dose is about 1, 2, 3, 4, 5, 10, 20, 100, 200, 300, 400, 500, 600, 700, 800, 900, 1000, 1100, 1200, or 1300 cGy, or between any of the two recited doses herein, such as 100-300 cGy, 200-500 cGy, 600-1000 cGy, or 700-1300 cGy. In some embodiments, the immunodeficient mouse is irradiated about 15 minutes, 30 minutes, 45 minutes, 1 hour, or more before engraftment with PBMCs and diseased cells (e.g., from a cell line or from a patient-derived xenograft). In some embodiments, the immunodeficient mouse is engrafted with PBMCs 1, 2, 3, 4, 5, 6, 7, 8, 9, 10, 11, 12, 13, 14, 15, 16, 17, or 18 days after irradiation.

PBMC Engraftment

As described above, in some embodiments, the irradiated immunodeficient mice are engrafted with PBMCs, humanizing the mice. The PBMCs may be engrafted after irradiation and before engraftment with diseased cells (e.g., tumor cells), after irradiation and engraftment with diseased cells (e.g., tumor cells) and before the engineered immune cell (e.g., T cell, B cell, or NK cell) therapy is administered, or concurrently with the administration of the engineered immune cell (e.g., T cell, B cell, or NK cell) therapy.

The term "peripheral blood mononuclear cells (PBMCs)" refers to peripheral blood cells having a round nucleus. These mononuclear blood cells recirculate between tissues and blood and are a critical component in the immune system to fight infection and adapt to intruders. There are two main types of mononuclear cells, lymphocytes and monocytes. The lymphocyte population of PBMCs typically includes T cells, B cells and NK cells.

PBMCs may be isolated from whole blood samples, for example (e.g., Ficoll gradient). In some embodiments, PBMCs from a subject (e.g., a human subject) for whom an engineered immune cell (e.g., T cell, B cell, or NK cell) therapy is being considered for possible administration may be used.

Methods of engrafting immunodeficient mice with PBMCs to yield a humanized mouse model are known in the art, and include, but are not limited to, intraperitoneal or intravenous injection (Shultz et al., J Immunol, 2015, 174: 6477-6489; Pearson et al., Curr Protoc Immunol. 2008;

15-21; Kim et al., AIDS Res Hum Retrovirus, 2016, 32(2): 194-2020; Yaguchi et al., Cell & Mol Immunol, 2018, 15:953-962). In some embodiments, the mouse is engrafted with $0.5\text{-}3.0\times10^7$ PBMCs. For example, the mouse is engrafted with $0.5\times10^7$, $0.6\times10^7$, $0.7\times10^7$, $0.8\times10^7$, $0.9\times10^7$, $1.0\times10^7$, $1.1\times10^7$, $1.2\times10^7$, $1.3\times10^7$, $1.4\times10^7$, $1.5\times10^7$, $1.6\times10^7$, $1.7\times10^7$, $1.8\times10^7$, $1.9\times10^7$, $2.0\times10^7$, $2.5\times10^7$, $3.0\times10^7$ or more PBMCs. In some embodiments, the mouse is engrafted with $0.5\text{-}0.75\times10^7$, $0.5\text{-}1.0\times10^7$, $0.5\text{-}1.1\times10^7$, $0.5\text{-}1.2\times10^7$, $0.5\text{-}1.3\times10^7$, $0.5\text{-}1.4\times10^7$, $0.5\text{-}1.5\times10^7$, $0.5\text{-}1.6\times10^7$, $0.5\text{-}1.7\times10^7$, $0.5\text{-}1.8\times10^7$, $0.5\text{-}1.9\times10^7$, $0.5\text{-}2.0\times10^7$, $0.5\text{-}2.25\times10^7$, $0.5\text{-}2.5\times10^7$, $0.5\text{-}3.0\times10^7$, $0.75\text{-}1.0\times10^7$, $0.75\text{-}1.1\times10^7$, $0.75\text{-}1.2\times10^7$, $0.75\text{-}1.3\times10^7$, $0.75\text{-}1.4\times10^7$, $0.75\text{-}1.5\times10^7$, $0.75\text{-}1.6\times10^7$, $0.75\text{-}1.7\times10^7$, $0.75\text{-}1.8\times10^7$, $0.75\text{-}1.9\times10^7$, $0.75\text{-}2.0\times10^7$, $0.75\text{-}2.25\times10^7$, $0.75\text{-}2.5\times10^7$, $0.75\text{-}3.0\times10^7$, $1.0\text{-}1.1\times10^7$, $1.0\text{-}1.2\times10^7$, $1.0\text{-}1.3\times10^7$, $1.0\text{-}1.4\times10^7$, $1.0\text{-}1.5\times10^7$, $1.0\text{-}1.6\times10^7$, $1.0\text{-}1.7\times10^7$, $1.0\text{-}1.8\times10^7$, $1.0\text{-}1.9\times10^7$, $1.0\text{-}2.0\times10^7$, $1.0\text{-}2.25\times10^7$, $1.0\text{-}2.5\times10^7$, $1.0\text{-}2.75\times10^7$, $1.0\text{-}3.0\times10^7$, $1.1\text{-}1.2\times10^7$, $1.1\text{-}1.3\times10^7$, $1.1\text{-}1.4\times10^7$, $1.1\text{-}1.5\times10^7$, $1.1\text{-}1.6\times10^7$, $1.1\text{-}1.7\times10^7$, $1.1\text{-}1.8\times10^7$, $1.1\text{-}1.9\times10^7$, $1.1\text{-}2.0\times10^7$, $1.1\text{-}2.25\times10^7$, $1.1\text{-}2.5\times10^7$, $1.1\text{-}2.75\times10^7$, $1.1\text{-}3.0\times10^7$, $1.2\text{-}1.3\times10^7$, $1.2\text{-}1.4\times10^7$, $1.2\text{-}1.5\times10^7$, $1.2\text{-}1.6\times10^7$, $1.2\text{-}1.7\times10^7$, $1.2\text{-}1.8\times10^7$, $1.2\text{-}1.9\times10^7$, $1.2\text{-}2.0\times10^7$, $1.2\text{-}2.25\times10^7$, $1.2\text{-}2.5\times10^7$, $1.2\text{-}2.75\times10^7$, $1.2\text{-}3.0\times10^7$, $1.3\text{-}1.4\times10^7$, $1.3\text{-}1.5\times10^7$, $1.3\text{-}1.6\times10^7$, $1.3\text{-}1.7\times10^7$, $1.3\text{-}1.8\times10^7$, $1.3\text{-}1.9\times10^7$, $1.3\text{-}2.0\times10^7$, $1.3\text{-}2.25\times10^7$, $1.3\text{-}2.5\times10^7$, $1.3\text{-}2.75\times10^7$, $1.3\text{-}3.0\times10^7$, $1.4\text{-}1.5\times10^7$, $1.4\text{-}1.6\times10^7$, $1.4\text{-}1.7\times10^7$, $1.4\text{-}1.8\times10^7$, $1.4\text{-}1.9\times10^7$, $1.4\text{-}2.0\times10^7$, $1.4\text{-}2.25\times10^7$, $1.4\text{-}2.5\times10^7$, $1.4\text{-}2.75\times10^7$, $1.4\text{-}3.0\times10^7$, $1.5\text{-}1.6\times10^7$, $1.5\text{-}1.7\times10^7$, $1.5\text{-}1.8\times10^7$, $1.5\text{-}1.9\times10^7$, $1.5\text{-}2.0\times10^7$, $1.5\text{-}2.25\times10^7$, $1.5\text{-}2.5\times10^7$, $1.5\text{-}2.75\times10^7$, $1.5\text{-}3.0\times10^7$, $1.6\text{-}1.7\times10^7$, $1.6\text{-}1.8\times10^7$, $1.6\text{-}1.9\times10^7$, $1.6\text{-}2.0\times10^7$, $1.6\text{-}2.25\times10^7$, $1.6\text{-}2.5\times10^7$, $1.6\text{-}2.75\times10^7$, $1.6\text{-}3.0\times10^7$, $1.7\text{-}1.8\times10^7$, $1.7\text{-}1.9\times10^7$, $1.7\text{-}2.0\times10^7$, $1.7\text{-}2.25\times10^7$, $1.7\text{-}2.5\times10^7$, $1.7\text{-}2.75\times10^7$, $1.7\text{-}3.0\times10^7$, $1.8\text{-}1.9\times10^7$, $1.8\text{-}2.0\times10^7$, $1.8\text{-}2.25\times10^7$, $1.8\text{-}2.5\times10^7$, $1.8\text{-}2.75\times10^7$, $1.8\text{-}3.0\times10^7$, $1.9\text{-}2.0\times10^7$, $1.9\text{-}2.25\times10^7$, $1.9\text{-}2.5\times10^7$, $1.9\text{-}2.75\times10^7$, $1.9\text{-}3.0\times10^7$, $2.0\text{-}2.25\times10^7$, $2.0\text{-}2.5\times10^7$, $2.0\text{-}2.75\times10^7$, $2.0\text{-}3.0\times10^7$, $2.25\text{-}2.5\times10^7$, $2.25\text{-}2.75\times10^7$, $2.25\text{-}3.0\times10^7$, $2.5\text{-}2.75\times10^7$, $2.5\text{-}3.0\times10^7$, or $2.75\text{-}3.0\times10^7$. In some embodiments, the mouse is engrafted with $2\times10^7$ PBMCs. According to some embodiments, the mouse is engrafted with $4.5\text{-}5.5\times10^7$ ($4.5\text{-}5.0\times10^7$, $5.0\text{-}5.5\times10^7$) PBMCs.

In some embodiments, the human PBMCs are engrafted 5 minutes, 10 minute, 15 minute, 20 minutes, 25 minutes, 0.5 hours, 1 hour, 1.5 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or more after irradiation. In some embodiments, the human PBMCs are engrafted 1-2 hours, 1-3 hours, 1-4 hours, 1-5 hours, 1-6 hours, 1-7 hours, 1-8 hours, 1-9 hours, 1-10 hours, 1-12 hours, 1-14 hours, 1-16 hours, 1-18 hours, 1-20 hours, 1-22 hours, 1-24 hours, 2-3 hours, 2-4 hours, 2-5 hours, 2-6 hours, 2-7 hours, 2-8 hours, 2-9 hours, 2-10 hours, 2-12 hours, 2-14 hours, 2-16 hours, 2-18 hours, 2-20 hours, 2-22 hours, 2-24 hours, 3-4 hours, 3-5 hours, 3-6 hours, 3-7 hours, 3-8 hours, 3-9 hours, 3-10 hours, 3-12 hours, 3-14 hours, 3-16 hours, 3-18 hours, 3-20 hours, 3-22 hours, 3-24 hours, 4-5 hours, 4-6 hours, 4-7 hours, 4-8 hours, 4-9 hours, 4-10 hours, 4-12 hours, 4-14 hours, 4-16 hours, 4-18 hours, 4-20 hours, 4-22 hours, 4-24 hours, 5-6 hours, 5-7 hours, 5-8 hours, 5-9 hours, 5-10 hours, 5-12 hours, 5-14 hours, 5-16 hours, 5-18 hours, 5-20 hours, 5-22 hours, 5-24 hours, 6-7 hours, 6-8 hours, 6-9 hours, 6-10 hours, 6-12 hours, 6-14 hours, 6-16 hours, 6-18 hours, 6-20 hours, 6-22 hours, 6-24 hours, 7-8 hours, 7-9 hours, 7-10 hours, 7-12 hours, 7-14 hours, 7-16 hours, 7-18 hours, 7-20 hours, 7-22 hours, 7-24 hours, 8-9 hours, 8-10 hours, 8-12 hours, 8-14 hours, 8-16 hours, 8-18 hours, 8-20 hours, 8-22 hours, 8-24 hours, 9-10 hours, 9-12 hours, 9-14 hours, 9-16 hours, 9-18 hours, 9-20 hours, 9-22 hours, 9-24 hours, 10-12 hours, 10-14 hours, 10-16 hours, 10-18 hours, 10-20 hours, 10-22 hours, 10-24 hours, 12-14 hours, 12-16 hours, 12-18 hours, 12-20 hours, 12-22 hours, 12-24 hours, 14-16 hours, 14-18 hours, 14-20 hours, 14-22 hours, 14-24 hours, 16-18 hours, 16-20 hours, 16-22 hours, 16-24 hours, 18-20 hours, 18-22 hours, 18-24 hours, 20-22 hours, 20-24 hours, or 22-24 hours after irradiation.

Diseased Cell Engraftment

In some embodiments, the immunodeficient mouse is administered/engrafted with diseased cells (e.g., from a cell line or a patient-derived xenograft) after irradiation. As used herein, the term "diseased cell" refers to a cell which is found in a diseased subject (e.g., an individual suffering from a disease or pathological condition, including cancer) and which is abnormal in terms of its structure and/or functioning and/or metabolism and/or genome compared to a cell having a structure, function, metabolism, and genome that are characteristic of a physiological cell found in a healthy subject (e.g., an individual not suffering from a disease or condition). Examples of diseased cells include, but are not limited to, cancer or tumor cells (discussed below), diseased vascular smooth muscle cells, diseased endothelial cells (e.g., in the case of atherosclerosis), diseased cells infected by a pathogen such as a virus (e.g., in the case of infectious diseases), and diseased cells undergoing fibrosis (e.g., in the case of fibrotic diseases). The phenotype, physical aspects or characteristics of the diseased cells will vary depending on the disease or condition (e.g., cancer, atherosclerosis, fibrotic disease and infectious disease, etc.) and standard techniques and knowledge (e.g., using disease-specific markers) can be used to distinguish a diseased cell from a non-diseased or healthy cell depending on the disease or condition.

Diseased cells may be administered using any method known in the art, for example, intravenous (e.g., tail vein injection), subcutaneous, intrafemoral, intraventricular, intracardial, intraperitoneal routes of administration, and the like. In some embodiments, the route of administration is intravenous infusion.

Patient-Derived Xenograft (PDX) Cells

In some embodiments, the immunodeficient mouse is administered/engrafted with a patient-derived xenograft (PDX) comprising diseased cells (e.g., tumor cells). PDXs are tissues that have been removed from a human. In some embodiments, the PDX comprises tumor cells. In some embodiments, the tumor is from a hematological malignancy, such as adult acute myeloid leukemia (AML). In some embodiments, the tumor is a solid tumor, such as those from bladder cancer, breast cancer, cervical cancer, colon cancer, rectal cancer, endometrial cancer, kidney cancer, lip and oral cancer, liver cancer, melanoma, mesothelioma, non-small cell lung cancer, nonmelanoma skin cancer, ovarian cancer, pancreatic cancer, prostate cancer, sarcoma, small cell lung cancer, and thyroid cancer.

In some embodiments, the immunodeficient mice are injected with an appropriate number of patient-derived cells, such as $0.1\text{-}10\times10^6$ human diseased (e.g., cancer) cells (e.g., $0.1\text{-}5.0\times10^6$ human diseased cells). In some embodiments, the appropriate amount of PDX cells is $0.1\text{-}0.2\times10^6$, $0.1\text{-}0.3\times10^6$, $0.1\text{-}0.4\times10^6$, $0.1\text{-}0.5\times10^6$, $0.1\text{-}0.6\times10^6$, $0.1\text{-}0.7\times10^6$, $0.1\text{-}0.8\times10^6$, $0.1\text{-}0.9\times10^6$, $0.1\text{-}1.0\times10^6$, $0.1\text{-}1.25\times10^6$, $0.1\text{-}1.5\times10^6$, $0.1\text{-}1.75\times10^6$, $0.1\text{-}2.0\times10^6$, $0.2\text{-}0.3\times10^6$, $0.2\text{-}$ $0.4 \times 10^6$, $0.2\text{-}0.5 \times 10^6$, $0.2\text{-}0.6 \times 10^6$, $0.2\text{-}0.7 \times 10^6$, $0.2\text{-}0.8 \times 10^6$, $0.2\text{-}0.9 \times 10^6$, $0.2\text{-}1.0 \times 10^6$, $0.2\text{-}1.25 \times 10^6$, $0.2\text{-}1.5 \times 10^6$, $0.2\text{-}1.75 \times 10^6$, $0.2\text{-}2.0 \times 10^6$, $0.3\text{-}0.4 \times 10^6$, $0.3\text{-}0.5 \times 10^6$, $0.3\text{-}0.6 \times 10^6$, $0.3\text{-}0.7 \times 10^6$, $0.3\text{-}0.8 \times 10^6$, $0.3\text{-}0.9 \times 10^6$, $0.3\text{-}1.0 \times 10^6$, $0.3\text{-}1.25 \times 10^6$, $0.3\text{-}1.5 \times 10^6$, $0.3\text{-}1.75 \times 10^6$, $0.3\text{-}2.0 \times 10^6$, $0.4\text{-}0.5 \times 10^6$, $0.4\text{-}0.6 \times 10^6$, $0.4\text{-}0.7 \times 10^6$, $0.4\text{-}0.8 \times 10^6$, $0.4\text{-}0.9 \times 10^6$, $0.4\text{-}1.0 \times 10^6$, $0.4\text{-}1.25 \times 10^6$, $0.4\text{-}1.5 \times 10^6$, $0.4\text{-}1.75 \times 10^6$, $0.4\text{-}2.0 \times 10^6$, $0.5\text{-}0.6 \times 10^6$, $0.5\text{-}0.7 \times 10^6$, $0.5\text{-}0.8 \times 10^6$, $0.5\text{-}0.9 \times 10^6$, $0.5\text{-}1.0 \times 10^6$, $0.5\text{-}1.25 \times 10^6$, $0.5\text{-}1.5 \times 10^6$, $0.5\text{-}1.75 \times 10^6$, $0.5\text{-}2.0 \times 10^6$, $0.6\text{-}0.7 \times 10^6$, $0.6\text{-}0.8 \times 10^6$, $0.6\text{-}0.9 \times 10^6$, $0.6\text{-}1.0 \times 10^6$, $0.6\text{-}1.25 \times 10^6$, $0.6\text{-}1.5 \times 10^6$, $0.6\text{-}1.75 \times 10^6$, $0.6\text{-}2.0 \times 10^6$, $0.7\text{-}0.8 \times 10^6$, $0.7\text{-}0.9 \times 10^6$, $0.7\text{-}1.0 \times 10^6$, $0.7\text{-}1.25 \times 10^6$, $0.7\text{-}1.5 \times 10^6$, $0.7\text{-}1.75 \times 10^6$, $0.7\text{-}2.0 \times 10^6$, $0.8\text{-}0.9 \times 10^6$, $0.8\text{-}1.0 \times 10^6$, $0.8\text{-}1.25 \times 10^6$, $0.8\text{-}1.5 \times 10^6$, $0.8\text{-}1.75 \times 10^6$, $0.8\text{-}2.0 \times 10^6$, $0.9\text{-}1.0 \times 10^6$, $0.9\text{-}1.25 \times 10^6$, $0.9\text{-}1.5 \times 10^6$, $0.9\text{-}1.75 \times 10^6$, $0.9\text{-}2.0 \times 10^6$, $1.0\text{-}1.25 \times 10^6$, $1.0\text{-}1.5 \times 10^6$, $1.0\text{-}1.75 \times 10^6$, $1.0\text{-}2.0 \times 10^6$, $1.25\text{-}1.5 \times 10^6$, $1.25\text{-}1.75 \times 10^6$, $1.25\text{-}2.0 \times 10^6$, $1.5\text{-}1.75 \times 10^6$, $1.5\text{-}2.0 \times 10^6$, $1.75\text{-}2.0 \times 10^6$ cancer cells (e.g., $0.1 \times 10^6$, $0.15 \times 10^6$, $0.2 \times 10^6$, $0.25 \times 10^6$, $0.3 \times 10^6$, $0.35 \times 10^6$, $0.4 \times 10^6$, $0.45 \times 10^6$, $0.5 \times 0^6$, $0.6 \times 10^6$, $0.7 \times 10^6$, $0.8 \times 10^6$, $0.9 \times 10^6$, $1.0 \times 10^6$, $1.1 \times 10^6$ $1.2 \times 10^6$ $1.3 \times 10^6$, $1.4 \times 10^6$, $1.5 \times 10^6$, $1.6.0 \times 10^6$, $1.7 \times 10^6$, $1.8 \times 10^6$, $1.9 \times 10^6$, $2.0 \times 10^6$ or more cells.

In some embodiments, the PDX is introduced into the mice before the PBMCs are engrafted and the human immune cells (e.g., human B- or T cells or NK cells) appear. In some embodiments, a PDX is introduced into a mouse immediately after irradiation. In some embodiments, the PDX is introduced 5 minutes, 10 minute, 15 minute, 20 minutes, 25 minutes, 0.5 hours, 1 hour, 1.5 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or more after irradiation. In some embodiments, the tumor cells are introduced 1-2 hours, 1-3 hours, 1-4 hours, 1-5 hours, 1-6 hours, 1-7 hours, 1-8 hours, 1-9 hours, 1-10 hours, 1-12 hours, 1-14 hours, 1-16 hours, 1-18 hours, 1-20 hours, 1-22 hours, 1-24 hours, 2-3 hours, 2-4 hours, 2-5 hours, 2-6 hours, 2-7 hours, 2-8 hours, 2-9 hours, 2-10 hours, 2-12 hours, 2-14 hours, 2-16 hours, 2-18 hours, 2-20 hours, 2-22 hours, 2-24 hours, 3-4 hours, 3-5 hours, 3-6 hours, 3-7 hours, 3-8 hours, 3-9 hours, 3-10 hours, 3-12 hours, 3-14 hours, 3-16 hours, 3-18 hours, 3-20 hours, 3-22 hours, 3-24 hours, 4-5 hours, 4-6 hours, 4-7 hours, 4-8 hours, 4-9 hours, 4-10 hours, 4-12 hours, 4-14 hours, 4-16 hours, 4-18 hours, 4-20 hours, 4-22 hours, 4-24 hours, 5-6 hours, 5-7 hours, 5-8 hours, 5-9 hours, 5-10 hours, 5-12 hours, 5-14 hours, 5-16 hours, 5-18 hours, 5-20 hours, 5-22 hours, 5-24 hours, 6-7 hours, 6-8 hours, 6-9 hours, 6-10 hours, 6-12 hours, 6-14 hours, 6-16 hours, 6-18 hours, 6-20 hours, 6-22 hours, 6-24 hours, 7-8 hours, 7-9 hours, 7-10 hours, 7-12 hours, 7-14 hours, 7-16 hours, 7-18 hours, 7-20 hours, 7-22 hours, 7-24 hours, 8-9 hours, 8-10 hours, 8-12 hours, 8-14 hours, 8-16 hours, 8-18 hours, 8-20 hours, 8-22 hours, 8-24 hours, 9-10 hours, 9-12 hours, 9-14 hours, 9-16 hours, 9-18 hours, 9-20 hours, 9-22 hours, 9-24 hours, 10-12 hours, 10-14 hours, 10-16 hours, 10-18 hours, 10-20 hours, 10-22 hours, 10-24 hours, 12-14 hours, 12-16 hours, 12-18 hours, 12-20 hours, 12-22 hours, 12-24 hours, 14-16 hours, 14-18 hours, 14-20 hours, 14-22 hours, 14-24 hours, 16-18 hours, 16-20 hours, 16-22 hours, 16-24 hours, 18-20 hours, 18-22 hours, 18-24 hours, 20-22 hours, 20-24 hours, or 22-24 hours after irradiation.

Cells and Cell Lines

In some embodiments, the immunodeficient mice are engrafted with primary cells. Human primary cells are isolated directly from tissues and retain the morphological and functional characteristics of their tissue of origin. In some embodiments, a primary cell is a cancer cell. In some embodiments, a primary cell is a neuronal cell. In some embodiments, a primary cell is a metabolic cell. In some embodiments, a primary cell is a cardiac cell. Other primary cells are contemplated herein.

In some embodiments, the immunodeficient mice are engrafted with stem cells, such as induced pluripotent stem cells (iPSCs). iPSCs are a type of pluripotent stem cell that can be generated directly from a somatic cell (see, e.g., Takahashi K et al. *Cell*. 2006; 126 (4): 663-76).

In some embodiments, the immunodeficient mice are engrafted with immortalized cells (immortalized cell lines). Immortalized cell lines are cells that have been manipulated to proliferate indefinitely and can thus be cultured for long periods of time. Non-limiting examples of commonly used immortalized cell lines include 3T3 cells, HeLa cells, COS cells, 293/293T/HEK-293T cells, MDCK cells, CHO cells, S2 cells, PC12 cells, Neuro-2a/N2a cells, and SH-SY5Y cells. Other immortalized cells are contemplated herein and described below.

In some embodiments, the immunodeficient mice are engrafted with tumor cells from tumor cell lines. Tumor cell lines are known in the art and are publicly accessible, for example, through ATCC or other collections. In some embodiments, the cell line is from a human tumor. In some embodiments, Raji, a cell line associated with human B cell lymphoma is used. In some embodiments, Jeko-1, a cell line associated with human mantle cell lymphoma is used. Examples of tumor cell lines include, but are not limited to, human lung carcinoma cell lines, such as A549 (SRCC768), Calu-1 (SRCC769), Calu-6 (SRCC770), H157 (SRCC771), H441 (SRCC772), H460 (SRCC773), SKMES-1 (SRCC774), SW900 (SRCC775), H522 (SRCC832), and H810 (SRCC833).

In some embodiments, the cell line is associated with human lung tumors, such as SRCC724 (adenocarcinoma, abbreviated as "AdenoCa") (LT1), SRCC725 (squamous cell carcinoma, abbreviated as "SqCCa) (LT1a), SRCC726 (adenocarcinoma) (LT2), SRCC727 (adenocarcinoma) (LT3), SRCC728 (adenocarcinoma) (LT4), SRCC729 (squamous cell carcinoma) (LT6), SRCC730 (adeno/squamous cell carcinoma) (LT7), SRCC731 (adenocarcinoma) (LT9), SRCC732 (squamous cell carcinoma) (LT10), SRCC733 (squamous cell carcinoma) (LT11), SRCC734 (adenocarcinoma) (LT12), SRCC735 (adeno/squamous cell carcinoma) (LT13), SRCC736 (squamous cell carcinoma) (LT15), SRCC737 (squamous cell carcinoma) (LT16), SRCC738 (squamous cell carcinoma) (LT 17), SRCC739 (squamous cell carcinoma) (LT18), SRCC740 (squamous cell carcinoma) (LT19), SRCC741 (lung cell carcinoma, abbreviated as "LCCa") (LT21), SRCC811 (adenocarcinoma) (LT22), SRCC825 (adenocarcinoma) (LT8), SRCC886 (adenocarcinoma) (LT25), SRCC887 (squamous cell carcinoma) (LT26), SRCC888 (adeno-BAC carcinoma) (LT27), SRCC889 (squamous cell carcinoma) (LT28), SRCC890 (squamous cell carcinoma) (LT29), SRCC891 (adenocarcinoma) (LT30), SRCC892 (squamous cell carcinoma) (LT31), SRCC894 (adenocarcinoma) (LT33). Also included are human lung tumors designated SRCC1125 [HF-000631], SRCC1127 [HF-000641], SRCC1129 [HF-000643], SRCC1133 [HF-000840], SRCC1135 [HF-000842], SRCC1227 [HF-001291], SRCC1229 [HF-001293], SRCC1230 [HF-001294], SRCC1231 [HF-001295], SRCC1232 [HF-001296], SRCC1233 [HF-001297], SRCC1235 [HF-001299], and SRCC1236 [HF-001300].

In some embodiments, the cell line is associated with human colon cancers. Examples of colon cancer cell lines include, but are not limited to, SW480 (adenocarcinoma, SRCC776), SW620 (lymph node metastasis of colon adenocarcinoma, SRCC777), Colo320 (carcinoma, SRCC778), HT29 (adenocarcinoma, SRCC779), HM7 (a high mucin producing variant of ATCC colon adenocarcinoma cell line, SRCC780), CaWiDr (adenocarcinoma, SRCC781), HCT116 (carcinoma, SRCC782), SKCO1 (adenocarcinoma, SRCC783), SW403 (adenocarcinoma, SRCC784), LS174T (carcinoma, SRCC785), Colo205 (carcinoma, SRCC828), HCT15 (carcinoma, SRCC829), HCC2998 (carcinoma, SRCC830), and KM12 (carcinoma, SRCC831). Primary colon tumors include colon adenocarcinomas designated CT2 (SRCC742), CT3 (SRCC743), CT8 (SRCC744), CT10 (SRCC745), CT12 (SRCC746), CT14 (SRCC747), CT15 (SRCC748), CT16 (SRCC749), CT17 (SRCC750), CT1 (SRCC751), CT4 (SRCC752), CT5 (SRCC753), CT6 (SRCC754), CT7 (SRCC755), CT9 (SRCC756), CT11 (SRCC757), CT18 (SRCC758), CT19 (adenocarcinoma, SRCC906), CT20 (adenocarcinoma, SRCC907), CT21 (adenocarcinoma, SRCC908), CT22 (adenocarcinoma, SRCC909), CT23 (adenocarcinoma, SRCC910), CT24 (adenocarcinoma, SRCC911), CT25 (adenocarcinoma, SRCC912), CT26 (adenocarcinoma, SRCC913), CT27 (adenocarcinoma, SRCC914),CT28 (adenocarcinoma, SRCC915), CT29 (adenocarcinoma, SRCC916), CT30 (adenocarcinoma, SRCC917), CT31 (adenocarcinoma, SRCC918), CT32 (adenocarcinoma, SRCC919), CT33 (adenocarcinoma, SRCC920), CT35 (adenocarcinoma, SRCC921), and CT36 (adenocarcinoma, SRCC922). Also included are human colon tumors designated SRCC1051 [HF-000499], SRCC1052 [HF-000539], SRCC1053 [HF-000575], SRCC1054 [HF-000698], SRCC1142 [HF-000762], SRCC1144 [HF-000789], SRCC1146 [HF-000795] and SRCC1148[HF-000811].

In some embodiments, the cell line is associated with human breast cancers. Examples of human breast carcinoma cell lines include, for example, HBL100 (SRCC759), MB435s (SRCC760), T47D (SRCC761), MB468 (SRCC762), MB175 (SRCC763), MB361 (SRCC764), BT20 (SRCC765), MCF7 (SRCC766), and SKBR3 (SRCC767), and human breast tumor center designated SRCC1057 [HF-000545]. Also included are human breast tumors designated SRCC1094, SRCC1095, SRCC1096, SRCC1097, SRCC1098, SRCC1099, SRCC1100, SRCC1101, and human breast-met-lung-NS tumor designated SRCC893 [LT 32].

In some embodiments, the cell line is associated with human kidney cancers. Examples of human kidney tumor cell lines include SRCC989 [HF-000611] and SRCC1014 [HF-000613].

In some embodiments, the cell line is associated with human testicular cancers. Examples of human testis tumor center includes SRCC1001 [HF-000733] and testis tumor margin SRCC999 [HF-000716].

In some embodiments, the cell line is associated with human parathyroid cancers. Examples of human parathyroid tumor cell lines include SRCC1002 [HF-000831] and SRCC1003 [HF-000832].

Other human tumor cell lines are contemplated herein.

In some embodiments, the immunodeficient mice are injected with an appropriate amount of tumor cells from a cancer cell line. In some embodiments, the immunodeficient mice are injected with $0.25 \times 10^6$ cancer cells. In some embodiments, the appropriate amount of tumor cells is $0.1$-$0.2 \times 10^6$, $0.1$-$0.3 \times 10^6$, $0.1$-$0.4 \times 10^6$, $0.1$-$0.5 \times 10^6$, $0.1$-$0.6 \times 10^6$, $0.1$-$0.7 \times 10^6$, $0.1$-$0.8 \times 10^6$, $0.1$-$0.9 \times 10^6$, $0.1$-$1.0 \times 10^6$, $0.1$-$1.25 \times 10^6$, $0.1$-$1.5 \times 10^6$, $0.1$-$1.75 \times 10^6$, $0.1$-$2.0 \times 10^6$, $0.2$-$0.3 \times 10^6$, $0.2$-$0.4 \times 10^6$, $0.2$-$0.5 \times 10^6$, $0.2$-$0.6 \times 10^6$, $0.2$-$0.7 \times 10^6$, $0.2$-$0.8 \times 10^6$, $0.2$-$0.9 \times 10^6$, $0.2$-$1.0 \times 10^6$, $0.2$-$1.25 \times 10^6$, $0.2$-$1.5 \times 10^6$, $0.2$-$1.75 \times 10^6$, $0.2$-$2.0 \times 10^6$, $0.3$-$0.4 \times 10^6$, $0.3$-$0.5 \times 10^6$, $0.3$-$0.6 \times 10^6$, $0.3$-$0.7 \times 10^6$, $0.3$-$0.8 \times 10^6$, $0.3$-$0.9 \times 10^6$, $0.3$-$1.0 \times 10^6$, $0.3$-$1.25 \times 10^6$, $0.3$-$1.5 \times 10^6$, $0.3$-$1.75 \times 10^6$, $0.3$-$2.0 \times 10^6$, $0.4$-$0.5 \times 10^6$, $0.4$-$0.6 \times 10^6$, $0.4$-$0.7 \times 10^6$, $0.4$-$0.8 \times 10^6$, $0.4$-$0.9 \times 10^6$, $0.4$-$1.0 \times 10^6$, $0.4$-$1.25 \times 10^6$, $0.4$-$1.5 \times 10^6$, $0.4$-$1.75 \times 10^6$, $0.4$-$2.0 \times 10^6$, $0.5$-$0.6 \times 10^6$, $0.5$-$0.7 \times 10^6$, $0.5$-$0.8 \times 10^6$, $0.5$-$0.9 \times 10^6$, $0.5$-$1.0 \times 10^6$, $0.5$-$1.25 \times 10^6$, $0.5$-$1.5 \times 10^6$, $0.5$-$1.75 \times 10^6$, $0.5$-$2.0 \times 10^6$, $0.6$-$0.7 \times 10^6$, $0.6$-$0.8 \times 10^6$, $0.6$-$0.9 \times 10^6$, $0.6$-$1.0 \times 10^6$, $0.6$-$1.25 \times 10^6$, $0.6$-$1.5 \times 10^6$, $0.6$-$1.75 \times 10^6$, $0.6$-$2.0 \times 10^6$, $0.7$-$0.8 \times 10^6$, $0.7$-$0.9 \times 10^6$, $0.7$-$1.0 \times 10^6$, $0.7$-$1.25 \times 10^6$, $0.7$-$1.5 \times 10^6$, $0.7$-$1.75 \times 10^6$, $0.7$-$2.0 \times 10^6$, $0.8$-$0.9 \times 10^6$, $0.8$-$1.0 \times 10^6$, $0.8$-$1.25 \times 10^6$, $0.8$-$1.5 \times 10^6$, $0.8$-$1.75 \times 10^6$, $0.8$-$2.0 \times 10^6$, $0.9$-$1.0 \times 10^6$, $0.9$-$1.25 \times 10^6$, $0.9$-$1.5 \times 10^6$, $0.9$-$1.75 \times 10^6$, $0.9$-$2.0 \times 10^6$, $1.0$-$1.25 \times 10^6$, $1.0$-$1.5 \times 10^6$, $1.0$-$1.75 \times 10^6$, $1.0$-$2.0 \times 10^6$, $1.25$-$1.5 \times 10^6$, $1.25$-$1.75 \times 10^6$, $1.25$-$2.0 \times 10^6$, $1.5$-$1.75 \times 10^6$, $1.5$-$2.0 \times 10^6$, $1.75$-$2.0 \times 10^6$ cancer cells (e.g., $0.1 \times 10^6$, $0.15 \times 10^6$, $0.2 \times 10^6$, $0.25 \times 10^6$, $0.3 \times 10^6$, $0.35 \times 10^6$, $0.4 \times 10^6$, $0.45 \times 10^6$, $0.5 \times 10^6$, $0.6 \times 10^6$, $0.7 \times 10^6$, $0.8 \times 10^6$, $0.9 \times 10^6$, $1.0 \times 10^6$, $1.1 \times 10^6$ $1.2 \times 10^6$ $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, $2.0 \times 10^6$ or more tumor cells).

In some embodiments, the cancer cells are introduced into the mice before the PBMCs are engrafted and the human immune cells (e.g., human B cells or T cells or NK cells) appear. In some embodiments, the tumor cells are introduced immediately after irradiation. In some embodiments, the tumor cells are introduced 5 minutes, 10 minute, 15 minute, 20 minutes, 25 minutes, 0.5 hours, 1 hour, 1.5 hours, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or more after irradiation. In some embodiments, the tumor cells are introduced 1-2 hours, 1-3 hours, 1-4 hours, 1-5 hours, 1-6 hours, 1-7 hours, 1-8 hours, 1-9 hours, 1-10 hours, 1-12 hours, 1-14 hours, 1-16 hours, 1-18 hours, 1-20 hours, 1-22 hours, 1-24 hours, 2-3 hours, 2-4 hours, 2-5 hours, 2-6 hours, 2-7 hours, 2-8 hours, 2-9 hours, 2-10 hours, 2-12 hours, 2-14 hours, 2-16 hours, 2-18 hours, 2-20 hours, 2-22 hours, 2-24 hours, 3-4 hours, 3-5 hours, 3-6 hours, 3-7 hours, 3-8 hours, 3-9 hours, 3-10 hours, 3-12 hours, 3-14 hours, 3-16 hours, 3-18 hours, 3-20 hours, 3-22 hours, 3-24 hours, 4-5 hours, 4-6 hours, 4-7 hours, 4-8 hours, 4-9 hours, 4-10 hours, 4-12 hours, 4-14 hours, 4-16 hours, 4-18 hours, 4-20 hours, 4-22 hours, 4-24 hours, 5-6 hours, 5-7 hours, 5-8 hours, 5-9 hours, 5-10 hours, 5-12 hours, 5-14 hours, 5-16 hours, 5-18 hours, 5-20 hours, 5-22 hours, 5-24 hours, 6-7 hours, 6-8 hours, 6-9 hours, 6-10 hours, 6-12 hours, 6-14 hours, 6-16 hours, 6-18 hours, 6-20 hours, 6-22 hours, 6-24 hours, 7-8 hours, 7-9 hours, 7-10 hours, 7-12 hours, 7-14 hours, 7-16 hours, 7-18 hours, 7-20 hours, 7-22 hours, 7-24 hours, 8-9 hours, 8-10 hours, 8-12 hours, 8-14 hours, 8-16 hours, 8-18 hours, 8-20 hours, 8-22 hours, 8-24 hours, 9-10 hours, 9-12 hours, 9-14 hours, 9-16 hours, 9-18 hours, 9-20 hours, 9-22 hours, 9-24 hours, 10-12 hours, 10-14 hours, 10-16 hours, 10-18 hours, 10-20 hours, 10-22 hours, 10-24 hours, 12-14 hours, 12-16 hours, 12-18 hours, 12-20 hours, 12-22 hours, 12-24 hours, 14-16 hours, 14-18 hours, 14-20 hours, 14-22 hours, 14-24 hours, 16-18 hours, 16-20 hours, 16-22 hours, 16-24 hours, 18-20 hours, 18-22 hours, 18-24 hours, 20-22 hours, 20-24 hours, or 22-24 hours after irradiation.

Methods for Assessing Efficacy of Immune Cell (e.g., T Cell, B Cell, NK Cell) Therapy In some embodiments, the method is for assessing the efficacy of an engineered immune cell (e.g., T cell, B cell, or NK cell) therapy. In some embodiments, a PBMC humanized mouse disease model can be established by engrafting an irradiated immunodeficient mice with diseased cells (e.g., cells from a PDX). After the diseased cells have grown for a sufficient amount of time in vivo, the mouse is treated with the prospective engineered immune cell (e.g., T cell, B cell, or NK cell) therapy and PBMCs. In some embodiments, a PBMC humanized mouse cancer model can be established by engrafting an irradiated immunodeficient mouse with tumor cells (e.g., cells from a tumor cell line or a PDX). After the tumor has grown for a sufficient time in vivo, the mouse is treated with the prospective engineered immune cell (e.g., T cell, B cell, or NK cell) therapy and PBMCs. By "sufficient time" it is meant that the tumor is the size or has the number of tumor cells needed to study the effects of the engineered immune cell (e.g., T cell, B cell, or NK cell) therapy, or in the case of a non-cancer disease mouse model, "sufficient time" refers to the amount of time needed to obtain the number of diseased cells necessary to study the effects of the engineered immune cell (e.g., T cell, B cell, or NK cell) therapy.

With respect to cancer mouse models, the tumor cells can be grown in the mouse to establish varying tumor burdens (e.g., the longer the mouse is untreated, the higher the tumor burden). As used herein, "tumor burden" refers to the total number of cancer cells or the total size of the tumor(s) in the model mouse. Tumor burdens can be low, moderate, or high and may be expressed as a percentage of the total body weight of the mouse. High tumor burdens are >5% of the body weight of the mouse (e.g., 5%, 5.1%, 5.2%, 5.3%, 5.4%, 5.5%, 5.6%, 5.7%, 5.8%, 5.9%, 6% or more). In some embodiments, the high tumor burden is 5-5.2%, 5-5.3%, 5-5.4%, 5-5.5%, 5-5.6%, 5-5.8%, 5-5.8%, 5-5.9%, 5-2%, 5.5-5.2%, 5.5-5.3%, 5.5-5.4%, 5.5-5.5%, 5.5-5.6%, 5.5-5.7%, 5.5-5.8%, 5.5-5.9%, 5.5-2%, 5.2-5.3%, 5.2-5.4%, 5.2-5.5%, 5.2-5.6%, 5.2-5.7%, 5.2-5.8%, 5.2-5.9%, 5.2-2%, 5.3-5.4%, 5.3-5.5%, 5.3-5.6%, 5.3-5.7%, 5.3-5.8%, 5.3-5.9%, 5.3-2%, 5.4-5.5%, 5.4-5.6%, 5.4-5.7%, 5.4-5.8%, 5.4-5.9%, 5.4-2%, 5.5-5.6%, 5.5-5.7%, 5.5-5.8%, 5.5-5.9%, 5.5-6%, 5.6-5.7%, 5.6-5.8%, 5.6-5.9%, 5.6-2%, 5.7-5.8%, 5.7-5.9%, 5.7-2%, 5.8-5.9%, 5.8-2%, or 5.9-6%. Moderate tumor burdens are 1<5% of the body weight of the mouse (e.g., 1%, 1.25%, 1.5%, 1.6%, 1.7%, 1.8%, 1.9%, 1.95%, 1.96%, 1.97%, 1.98%, 1.99%, 2%, 2.25%, 2.5%, 2.75%, 3%, 3.25%, 3.5%, 3.75%, 4%, 4.25% 4.5%, 4.75%). In some embodiments, the moderate tumor burden is 1.5-1.6%, 1.5-1.7%, 1.5-1.8%, 1.5-1.9%, 1.6-1.7%, 1.6-1.8%, 1.6-1.9%, 1.7-1.8%, 1.7-1.9%, or 1.8-1.9%. In some embodiments, the moderate tumor burden is 1-2%, 1-2.25%, 1-2.5%, 1-2.75%, 1-3%, 1-3.25%, 1-3.5%, 1-3.75%, 1-4%, 1-4.25%, 1-4.5%, 1-4.75%, 2-2.25%, 2-2.5%, 2-2.75%, 2-3%, 2-3.25%, 2-3.5%, 2-3.75%, 2-4%, 2-4.25%, 2-4.5%, 2-4.75%, 2.5-2.75%, 2.5-3%, 2.5-3.25%, 2.5-3.5%, 2.5-3.75%, 2.5-4%, 2.5-4.25%, 2.5-4.5%, 2.5-4.75%, 3-3.25%, 3-3.5%, 3-3.75%, 3-4%, 3-4.25%, 3-4.5%, 3-4.75%, 3.5-3.75%, 3.5-4%, 3.5-4.25%, 3.5-4.5%, 3.5-4.75%, 4-4.25%, 4-4.5%, 4-4.75%, or 4.5-4.75%. Low tumor burdens are less than 1% of the mouse's body weight (e.g., 0.05%, 0.1%, 0.2%, 0.3%, 0.4%, 0.45%, 0.46%, 0.47%, 0.48%, or 0.49%). In some embodiments, the low tumor burden is 0.1-0.2%, 0.1-0.3%, 0.1-0.4%, 0.2-0.3%, 0.2-0.4%, or 0.3-0.4%

In some embodiments, the engineered immune cell (e.g., T cell, B cell, or NK cell) therapy is administered 1, 2, 3, 4, 5, 6, 7, 8, 9, 10, 11, 12, 13, or 14 days after the mouse was injected with the diseased cells (e.g., tumor cells) (e.g., 1-2 days, 1-3 days, 1-4 days, 1-5 days, 1-6 days, 1-7 days, 1-8 days, 1-9 days, 1-10 days, 1-11 days, 1-12 days, 1-13 days, 1-14 days, 2-3 days, 2-4 days, 2-5 days, 2-6 days, 2-7 days, 2-8 days, 2-9 days, 2-10 days, 2-11 days, 2-12 days, 2-13 days, 2-14 days, 3-4 days, 3-5 days, 3-6 days, 3-7 days, 3-8 days, 3-9 days, 3-10 days, 3-11 days, 3-12 days, 3-13 days, 3-14 days, 4-5 days, 4-6 days, 4-7 days, 4-8 days, 4-9 days, 4-10 days, 4-11 days, 4-12 days, 4-13 days, 4-14 days, 5-6 days, 5-7 days, 5-8 days, 5-9 days, 5-10 days, 5-11 days, 5-12 days, 5-13 days, 5-14 days, 6-7 days, 6-8 days, 6-9 days, 6-10 days, 6-11 days, 6-12 days, 6-13 days, 6-14 days, 7-8 days, 7-9 days, 7-10 days, 7-11 days, 7-12 days, 7-13 days, 7-14 days, 8-9 days, 8-10 days, 8-11 days, 8-12 days, 8-13 days, 8-14 days, 9-10 days, 9-11 days, 9-12 days, 9-13 days, 9-14 days, 11-12 days, 11-13 days, 11-14 days, 12-13 days, 12-14 days, or 13-14 days). Optionally, the human PBMCs may be administered with engineered immune cell (e.g., T cell, B cell, or NK cell) therapy (e.g., in the same dose or in a different dose simultaneously). The engineered immune cell (e.g., T cell, B cell, or NK cell) therapy, which can include any of the engineered immune cell (e.g., T cell, B cell, or NK cell) constructs described herein may be administered at a dose of $1\text{-}20\times10^6$ engineered immune cells (e.g., T cells, B cells, or NK cells) cells, for example $1\text{-}2\times10^6$, $1\text{-}3\times10^6$, $1\text{-}4\times10^6$, $1\text{-}5\times10^6$, $1\text{-}6\times10^6$, $1\text{-}7\times10^6$, $1\text{-}8\times10^6$, $1\text{-}9\times10^6$, $1\text{-}10\times10^6$, $1\text{-}12\times10^6$, $1\text{-}14\times10^6$, $1\text{-}16\times10^6$, $1\text{-}18\times10^6$, $1\text{-}20\times10^6$, $2\text{-}3\times10^6$, $2\text{-}4\times10^6$, $2\text{-}5\times10^6$, $2\text{-}6\times10^6$, $2\text{-}7\times10^6$, $2\text{-}8\times10^6$, $2\text{-}9\times10^6$, $2\text{-}10\times10^6$, $2\text{-}12\times10^6$, $2\text{-}14\times10^6$, $2\text{-}16\times10^6$, $2\text{-}18\times10^6$, $2\text{-}20\times10^6$, $3\text{-}4\times10^6$, $3\text{-}5\times10^6$, $3\text{-}6\times10^6$, $3\text{-}7\times10^6$, $3\text{-}8\times10^6$, $3\text{-}9\times10^6$, $3\text{-}10\times10^6$, $3\text{-}12\times10^6$, $3\text{-}14\times10^6$, $3\text{-}16\times10^6$, $3\text{-}18\times10^6$, $3\text{-}20\times10^6$, $4\text{-}5\times10^6$, $4\text{-}6\times10^6$, $4\text{-}7\times10^6$, $4\text{-}8\times10^6$, $4\text{-}9\times10^6$, $4\text{-}10\times10^6$, $4\text{-}12\times10^6$, $4\text{-}14\times10^6$, $4\text{-}16\times10^6$, $4\text{-}18\times10^6$, $4\text{-}20\times10^6$, $5\text{-}6\times10^6$, $5\text{-}7\times10^6$, $5\text{-}8\times10^6$, $5\text{-}9\times10^6$, $5\text{-}10\times10^6$, $5\text{-}12\times10^6$, $5\text{-}14\times10^6$, $5\text{-}16\times10^6$, $5\text{-}18\times10^6$, $5\text{-}20\times10^6$, $6\text{-}7\times10^6$, $6\text{-}8\times10^6$, $6\text{-}9\times10^6$, $6\text{-}10\times10^6$, $6\text{-}12\times10^6$, $6\text{-}14\times10^6$, $6\text{-}16\times10^6$, $6\text{-}18\times10^6$, $6\text{-}20\times10^6$, $7\text{-}8\times10^6$, $7\text{-}9\times10^6$, $7\text{-}10\times10^6$, $7\text{-}12\times10^6$, $7\text{-}14\times10^6$, $7\text{-}16\times10^6$, $7\text{-}18\times10^6$, $7\text{-}20\times10^6$, $8\text{-}9\times10^6$, $8\text{-}10\times10^6$, $8\text{-}12\times10^6$, $8\text{-}14\times10^6$, $8\text{-}16\times10^6$, $8\text{-}18\times10^6$, $8\text{-}20\times10^6$, $9\text{-}10\times10^6$, $9\text{-}12\times10^6$, $9\text{-}14\times10^6$, $9\text{-}16\times10^6$, $9\text{-}18\times10^6$, $9\text{-}20\times10^6$, $10\text{-}12\times10^6$, $10\text{-}14\times10^6$, $10\text{-}16\times10^6$, $10\text{-}18\times10^6$, $10\text{-}20\times10^6$, $12\text{-}14\times10^6$, $12\text{-}16\times10^6$, $12\text{-}18\times10^6$, $12\text{-}20\times10^6$, $14\text{-}16\times10^6$, $14\text{-}18\times10^6$, $14\text{-}20\times10^6$, $16\text{-}18\times10^6$, $16\text{-}20\times10^6$, $18\text{-}20\times10^6$ engineered immune cells. In some embodiments, the mouse is administered a dose of $1\times10^6$, $2\times10^6$, $3\times10^6$, $4\times10^6$, $5\times10^6$, $6\times10^6$, $7\times10^6$, $8\times10^6$, $9\times10^6$, $10\times10^6$, $11\times10^6$, $12\times10^6$, $13\times10^6$, $14\times10^6$, $15\times10^6$, $16\times10^6$, $17\times10^6$, $18\times10^6$, $19\times10^6$, $20\times10^6$, or more engineered immune cells. In some embodiments, the mouse is administered one dose of engineered immune cell (e.g., T cell, B cell, or NK cell) therapy. In some embodiments, the mouse is administered 1-2, 1-3,1-4, 1-5, 2-3, 2-4, 2-5, 3-4, 3-5, or 4-5 doses (e.g., 2, 3, 4, 5, or more doses) of engineered immune cell (e.g., T cell, B cell, or NK cell) therapy. In some embodiments, the initial dose is divided into two or more smaller doses to mitigate the risk of side effects (e.g., instead of administering one initial dose, half the initial dose is administered twice). The time between administrations can be, for example, 12 hours, 1 day, 2 days, 3 days, 4 days, 5 days, 6 days, 7 days, 8 days, 9 days, 10 days, or more. In some embodiments, the time between administrations is 1-2 days, 1-3 days, 1-4 days, 1-5 days, 1-6, days, 1-7 days, 1-8 days, 1-9 days, 1-10 days, 2-3 days, 2-4 days, 2-5 days, 2-6 days, 2-7 days, 2-8 days, 2-9 days, 2-10 days, 3-4 days, 3-5 days, 3-6 days, 3-7 days, 3-8 days, 3-9 days, 3-10 days, 4-5 days, 4-6 days, 4-7 days, 4-8 days, 4-9 days, 4-10 days, 5-6 days, 5-7 days, 5-8 days, 5-9 days, 5-10 days, 6-7 days, 6-8 days, 6-9 days, 6-10 days, 7-8 days, 7-9 days, 7-10 days, 8-9 days, 8-10 days, or 9-10 days.

In some embodiments, the methods comprise assessing the efficacy and/or toxicity of any one of the engineered immune cells described herein. In some embodiments, 2, 3, 4, 5, or 6 different types of engineered immune cell therapies are assessed simultaneously.

In some embodiments, the human PBMCs are engrafted before the human engineered immune cell (e.g., T cell, B cell, or NK cell) therapy. For example, in some embodiments, the human PBMCs are engrafted immediately before the engineered immune cell (e.g., T cell, B cell, or NK cell) therapy. In some embodiments, the human PBMCs are engrafted 0.5-6 days before the human engineered immune cell (e.g., T cell, B cell, or NK cell) therapy is administered, e.g., 0.5 days, 1 day, 1.5 days, 2 days, 2.5 days, 3 days, 3.5 days, 4 days, 4.5 days, 5 days, 5.5 days, or 6 days. In some embodiments, the human PBMCs are administered 1-2 days, 1-3 days, 1-4 days, 1-5 days, 1-6 days, 2-3 days, 2-4 days, 2-5 days, 2-6 days, 3-4 days, 3-5 days, 3-6 days, 4-5 days, 4-6 days, or 5-6 days before the human engineered immune cell (e.g., T cell, B cell, or NK cell) therapy is administered.

As will be appreciated by those of skill in the art, the engineered immune cell (e.g., T cell, B cell, or NK cell) therapy can be administered to PBMC humanized mice using any applicable route of administration. Exemplary routes of administration include, but not limited to, intravenous (e.g., via tail vein), subcutaneous, intrafemoral, intraventricular, intracardial, intraperitoneal routes of administration. In some embodiments, the route of administration is intravenous injection via tail vein.

In some embodiments, the PBMCs and the immune cells for engineered immune cell (e.g., T cell, B cell, or NK cell) therapy are from the same subject (the two cell types are autologous). In other embodiments, the PBMCs and the immune cells are from different subjects (the two cell types are allogeneic). For example, the models described herein may be used to test a universal allogeneic engineered immune cell (e.g., T cell, B cell, or NK cell) therapy. In some embodiments, the PBMCs, the immune cells (e.g., T cells, B cells, NK cells), and the tumor cells are from the same subject. In some embodiments, the PBMCs, immune cells (e.g., T cells, B cells, NK cells), and tumor cells are from two or more subjects (e.g., the PBMCs and immune cells are from one subject and the tumor cells are from a different subject; the PBMCs and the tumor cells are from one subject and the immune cells are from a different subject; or the immune cells and the tumor cells are from one subject and the PBMCs are from a different subject). In some embodiments, a subject from which the PBMCs and/or immune cells (e.g., T cells, B cells, NK cells) are obtained is a human subject. Other mammals are contemplated herein.

Following administration of the engineered immune cell (e.g., T cell, B cell, or NK cell) therapy, a candidate agent effective for the treatment of CRS treatment (e.g., anticytokine treatment) may be administered (e.g., to prevent or reduce the effects of CRS). In some embodiments, the mouse models are used to determine whether a candidate CRS treatment will eliminate or reduce CRS in response to a specific engineered immune cell (e.g., T cell, B cell, or NK cell) therapy, as described herein. In some embodiments, the CRS treatment is administered simultaneously with the engineered immune cell (e.g., T cell, B cell, or NK cell) therapy. In some embodiments, the CRS treatment is administered 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 3.5 hours, 4 hours, 5 hours, 6 hours, 7 hours, 8 hours, 9 hours, 10 hours, 11 hours, 12 hours, 1 day, 2 days, 3 days, 4 days, 5 days, 6 days, 7 days, 8 days, 9 days, 10 days, 11 days, 12 days, or more after the engineered immune cell (e.g., T cell, B cell, or NK cell) therapy has been administered. In some embodiments, the CRS treatment is administered 1-5 minutes, 1-10 minutes, 1-15 minutes, 1-20 minutes, 1-30 minutes, 1-45 minutes, 1-60 minutes, 2-5 minutes, 2-10 minutes, 2-15 minutes, 2-20 minutes, 2-30 minutes, 2-45 minutes, 2-60 minutes, 3-5 minutes, 3-10 minutes, 3-15 minutes, 3-20 minutes, 3-30 minutes, 3-45 minutes, 3-60 minutes, 4-5 minutes, 4-10 minutes, 4-15 minutes, 4-20 minutes, 4-30 minutes, 4-45 minutes, 4-60 minutes, 5-10 minutes, 5-20 minutes, 5-30 minutes, 5-45 minutes, 5-60 minutes, 10-20 minutes, 10-30 minutes, 10-40 minutes, 10-50 minutes, 10-60 minutes, 15-30 minutes, 15-45 minutes, 15-60 minutes, 30-45 minutes, 30-60 minutes, 1-2 hours, 1-3 hours, 1-4 hours, 1-5 hours, 1-6 hours, 1-7 hours, 1-8 hours, 1-9 hours, 1-10 hours, 1-11 hours, 1-12 hours, 2-3 hours, 2-4 hours, 2-5 hours, 2-6 hours, 2-7 hours, 2-8 hours, 2-9 hours, 2-10 hours, 2-11 hours, 2-12 hours, 3-4 hours, 3-5 hours, 3-6 hours, 3-7 hours, 3-8 hours, 3-9 hours, 3-10 hours, 3-11 hours, 3-12 hours, 4-5 hours, 4-6 hours, 4-7 hours, 4-8 hours, 4-9 hours, 4-10 hours, 4-11 hours, 4-12 hours, 5-6 hours, 5-7 hours, 5-8 hours, 5-9 hours, 5-10 hours, 5-11 hours, 5-12 hours, 6-7 hours, 6-8 hours, 6-9 hours, 6-10 hours, 6-11 hours, 6-12 hours, 7-8 hours, 7-9 hours, 7-10 hours, 7-11 hours, 7-12 hours, 8-9 hours, 8-10 hours, 8-11 hours, 8-12 hours, 9-10 hours, 9-11 hours, 9-12 hours, 10-11 hours, 10-12 hours, 11-12 hours, 12-16 hours, 12-18 hours, 12-20 hours, 12-24 hours, 1-2 days, 1-3 days, 1-4 days, 1-5 days, 1-6 days, 1-7 days, 1-8 days, 1-9 days, 1-10 days, 1-11 days, 1-12 days, 2-3 days, 2-4 days, 2-5 days, 2-6 days, 2-7 days, 2-8 days, 2-9 days, 2-10 days, 2-11 days, 2-12 days, 3-4 days, 3-5 days, 3-6 days, 3-7 days, 3-8 days, 3-9 days, 3-10 days, 3-11 days, 3-12 days, 4-5 days, 4-6 days, 4-7 days, 4-8 days, 4-9 days, 4-10 days, 4-11 days, 4-12 days, 5-6 days, 5-7 days, 5-8 days, 5-9 days, 5-10 days, 5-11 days, 5-12 days, 6-7 days, 6-8 days, 6-9 days, 6-10 days, 6-11 days, 6-12 days, 7-8 days, 7-9 days, 7-10 days, 7-11 days, 7-12 days, 8-9 days, 8-10 days, 8-11 days, 8-12 days, 9-10 days, 9-11 days, 9-12 days, 10-11 days, 10-12 days, or 11-12 days after the engineered immune cell (e.g., T cell, B cell, or NK cell) therapy has been administered. In some embodiments, the CRS treatment is administered prophylactically, such as 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 3.5 hours, 4 hours, 5 hours, 6 hours, 7 hours, 8 hours, 9 hours, 10 hours, 11 hours, 12 hours, 1 day, 2 days, 3 days, or 4 days before the engineered immune cell (e.g., T cell, B cell, or NK cell) therapy is administered. In some embodiments, the CRS treatment is administered 1-5 minutes, 1-10 minutes, 1-15 minutes, 1-20 minutes, 1-30 minutes, 1-45 minutes, 1-60 minutes, 2-5 minutes, 2-10 minutes, 2-15 minutes, 2-20 minutes, 2-30 minutes, 2-45 minutes, 2-60 minutes, 3-5 minutes, 3-10 minutes, 3-15 minutes, 3-20 minutes, 3-30 minutes, 3-45 minutes, 3-60 minutes, 4-5 minutes, 4-10 minutes, 4-15 minutes, 4-20 minutes, 4-30 minutes, 4-45 minutes, 4-60 minutes, 5-10 minutes, 5-20 minutes, 5-30 minutes, 5-45 minutes, 5-60 minutes, 10-20 minutes, 10-30 minutes, 10-40 minutes, 10-50 minutes, 10-60 minutes, 15-30 minutes, 15-45 minutes, 15-60 minutes, 30-45 minutes, 30-60 minutes, 1-2 hours, 1-3 hours, 1-4 hours, 1-5 hours, 1-6 hours, 1-7 hours, 1-8 hours, 1-9 hours, 1-10 hours, 1-11 hours, 1-12 hours, 2-3 hours, 2-4 hours, 2-5 hours, 2-6 hours, 2-7 hours, 2-8 hours, 2-9 hours, 2-10 hours, 2-11 hours, 2-12 hours, 3-4 hours, 3-5 hours, 3-6 hours, 3-7 hours, 3-8 hours, 3-9 hours, 3-10 hours, 3-11 hours, 3-12 hours, 4-5 hours, 4-6 hours, 4-7 hours, 4-8 hours, 4-9 hours, 4-10 hours, 4-11 hours, 4-12 hours, 5-6 hours, 5-7 hours, 5-8 hours, 5-9 hours, 5-10 hours, 5-11 hours, 5-12 hours, 6-7 hours, 6-8 hours, 6-9 hours, 6-10 hours, 6-11 hours, 6-12 hours, 7-8 hours, 7-9 hours, 7-10 hours, 7-11 hours, 7-12 hours, 8-9 hours, 8-10 hours, 8-11 hours, 8-12 hours, 9-10 hours, 9-11 hours, 9-12 hours, 10-11 hours, 10-12 hours, 11-12 hours, 12-16 hours, 12-18 hours, 12-20 hours, 12-24 hours, 1-2 days, 1-3 days, 1-4 days, 2-3 days, 2-4 days, or 3-4 days, before the engineered immune cell (e.g., T cell, B cell, or NK cell) therapy has been administered.

After the PBMC humanized mouse is administered the engineered immune cell (e.g., T cell, B cell, or NK cell) therapy (and optionally, a CRS treatment), the mouse is observed to assess the efficacy of the engineered immune cell (e.g., T cell, B cell, or NK cell) therapy. As used herein, "efficacy" refers to the ability of the therapy administered to a subject to produce a therapeutic effect in the subject. In some embodiments, the therapy comprises engineered immune cell (e.g., T cell, B cell, or NK cell) therapy. In some embodiments, the therapy comprises engineered immune cell (e.g., T cell, B cell, or NK cell) therapy and anti-cytokine therapy. In some embodiments, the mouse models are used to determine whether a candidate CRS treatment will eliminate or reduce CRS in response to a specific engineered immune cell (e.g., T cell, B cell, or NK cell) therapy, as described herein. By "eliminate," it is meant that the CRS treatment reduces the level of circulating cytokines following engineered immune cell (e.g., T cell, B cell, or NK cell) therapy in the mouse to the level of circulating cytokines present in the mouse prior to administration of the engineered immune cell (e.g., T cell, B cell, or NK cell) therapy or to the level of circulating cytokines in a control mouse that did not receive the engineered immune cell (e.g., T cell, B cell, or NK cell) therapy. By "reduce," it is meant that the CRS treatment reduces the level of circulating cytokines following engineered immune cell (e.g., T cell, B cell, or NK cell) therapy in the mouse to a level that is lower than would be found in a mouse administered the engineered immune cell (e.g., T cell, B cell, or NK cell) therapy without the CRS treatment. In some embodiments, the CRS treatment reduces the circulating cytokine level (e.g., the cytokine level of one or more cytokines) 5%, 10%, 15%, 20%, 25%, 30%, 35%, 40%, 45%, 50%, 55%, 60%, 65%, 70%, 75%, 80%, 85%, 90%, 95%, or more. In some embodiments, the circulating cytokine level (e.g., one or more cytokines) in the mouse is reduced 10-20%, 10-30%, 10-40%, 10-50%, 10-60%, 10-70%, 10-80%, 10-90%, 10-100%, 20-30%, 20-40%, 20-50%, 20-60%, 20-70%, 20-80%, 20-90%, 20-100%, 30-40%, 30-50%, 30-60%, 30-70%, 30-80%, 30-90%, 30-100%, 40-50%, 40-60%, 40-70%, 40-80%, 40-90%, 40-100%, 50-60%, 50-70%, 50-80%, 50-90%, 50-100%, 60-70%, 60-80%, 60-90%, 60-100%, 70-80%, 70-90%, 70-100%, 80-90%, 80-100%, or 90-100%.

To determine the efficacy of the engineered immune cell (e.g., T cell, B cell, or NK cell) therapy, tumor growth can be monitored, for example, with in vivo bioluminescence imaging (BLI) as described herein, genomic studies, histology studies, or with any other method of measuring or approximating the volume of a tumor. Efficacy may be determined by using the Response Evaluation Criteria in Solid Tumors (RECIST) criteria, the 3-category method, the 4-response mRECIST criterion, and the 5-category method (Eisenhauer et al., *Eur J Cancer*, 2009, 45(2): 228-247; Bertotti et al., *Nature*. 2015; 526(7572):263-7; Gao et al., *Nat Med.* 2015; 21(11):1318-25; Houghton et al., *Pediatr Blood Cancer.* 2007; 49(7):928-40). Other measurements of efficacy relate to tumor volume and include, but are not limited to, progression-free survival, tumor volume doubling time, relative tumor volume (RTV), tumor growth inhibition (changes in tumor volume relative to initial tumor volume), and tumor growth rate. Progression-free survival is the length of time during and following treatment when the subject has the disease, but it does not get worse (e.g., the amount of time, during and after engineered immune cell (e.g., T cell, B cell, or NK cell) therapy, that the tumor does not grow). Tumor volume doubling time (DT) is the amount of time it takes the tumor volume to double (faster doubling times indicate a more malignant tumor) and typically determined from two volume estimations with measurement time intervals comparable with or shorter than DT. Relative tumor volume is the relative in tumor volume over time and is calculated as: (absolute tumor volume on day X)×(100/absolute tumor volume on day 0). Day 0 is the day the engineered immune cell (e.g., T cell, B cell, or NK cell) therapy begins. Similarly, tumor growth inhibition (TGI), which is expressed as a percentage, examines the changes in tumor volume relative to the initial tumor volume using the formula: (1−(mean volume of treated tumors)/(mean volume of control tumors))×100%. Tumor growth rate is estimated using a variety of different models. For an exponentially growing tumor, the growth rate is proportional to its volume: $(1/N) \times (dV/dt)$, where V is the volume of the tumor, and dV and dt are the change in volume and time, respectively.

The tumor volume can be measured any number of times throughout the time course experiment (e.g., 1, 2, 3, 4, 5, 6, 7, 8, 9, 10 or more times). In some embodiments, the tumor volume is measured 1-2 times, 1-3 times, 1-4 time, 1-5 times, 1-6 times, 1-7 times, 1-8 times, 1-9 times, 1-10 times, 2-4 times, 2-6 times, 2-8 times, 2-10 times, 3-6 times, 3-8 times, 3-10 times, 4-6 times, 4-8 times, 4-10 times, 5-8 times, 5-10 times, 6-8 times, 6-10 times, 7-10 times, 8-10 times, or 9-10 times. The tumor volume may be measured over time, for example 1, 2, 3, 4, 5, 6, 7, 8, 9, 10, 11, 12, 13, 14, 15, 16, 17, 18, 19, 20, 21 or more days after engraftment with the tumor cells. In some embodiments, the tumor volume is measured 1-2 days, 1-3 days, 1-4 days, 1-5 days, 1-6 days, 1-7 days, 1-8 days, 1-9 days, 1-10 days, 1-11 days, 1-12 days, 2-3 days, 2-4 days, 2-5 days, 2-6 days, 2-7 days, 2-8 days, 2-9 days, 2-10 days, 2-11 days, 2-12 days, 3-4 days, 3-5 days, 3-6 days, 3-7 days, 3-8 days, 3-9 days, 3-10 days, 3-11 days, 3-12 days, 4-5 days, 4-6 days, 4-7 days, 4-8 days, 4-9 days, 4-10 days, 4-11 days, 4-12 days, 5-6 days, 5-7 days, 5-8 days, 5-9 days, 5-10 days, 5-11 days, 5-12 days, 6-7 days, 6-8 days, 6-9 days, 6-10 days, 6-11 days, 6-12 days, 7-8 days, 7-9 days, 7-10 days, 7-11 days, 7-12 days, 8-9 days, 8-10 days, 8-11 days, 8-12 days, 9-10 days, 9-11 days, 9-12 days, 10-11 days, 10-12 days, 10-14 days, 10-16 days, 10-18 days, 10-20 days, 10-21 days, 12-14 days, 12-16 days, 12-18 days, 12-20 days, 12-21 days, 14-16 days, 14-18 days, 14-20 days, 14-21 days, 15-16 days, 15-18 days, 15-20 days, 15-21 days, 16-18 days, 16-20 days, 16-21 days, 17-19 days, 17-21 days, 18-19 days, 18-20 days, 18-21 days, 19-20 days, 19-21 days, or 20-21 days.

In some embodiments, the change in tumor volume is indicative of the efficacy of the human engineered immune cell (e.g., T cell, B cell, or NK cell) therapy (and, optionally, the CRS treatment). In some embodiments, the tumor volume in a mouse treated with human engineered immune cell (e.g., T cell, B cell, or NK cell) therapy may be compared to the tumor volume in a mouse that was not treated with the human engineered immune cell (e.g., T cell, B cell, or NK cell) therapy. In some embodiments, the tumor volume is reduced 5%, 10%, 15%, 20%, 25%, 30%, 35%, 40%, 45%, 50%, 55%, 60%, 65%, 70%, 75%, 80%, 85%, 90%, 95%, or more relative to a mouse that did not receive the human engineered immune cell (e.g., T cell, B cell, or NK cell) therapy or relative to an earlier time point. In some embodiments, the tumor volume is reduced 10-20%, 10-30%, 10-40%, 10-50%, 10-60%, 10-70%, 10-80%, 10-90%, 10-100%, 20-30%, 20-40%, 20-50%, 20-60%, 20-70%, 20-80%, 20-90%, 20-100%, 30-40%, 30-50%, 30-60%, 30-70%, 30-80%, 30-90%, 30-100%, 40-50%, 40-60%, 40-70%, 40-80%, 40-90%, 40-100%, 50-60%, 50-70%, 50-80%, 50-90%, 50-100%, 60-70%, 60-80%, 60-90%, 60-100%, 70-80%, 70-90%, 70-100%, 80-90%, 80-100%, or 90-100% relative to a mouse that did not receive the human engineered immune cell (e.g., T cell, B cell, or NK cell) therapy or relative to an earlier time point.

CRS induction may also be monitored through body weight measurement, as acute toxicity relates to significant mouse body weight loss. Further, clinical observations may be indicative of CRS. Examples of clinical observations relevant to CRS include: a hunched posture with tiptoe/abnormal gait, reduced activity (e.g., not moving unless being stimulated), and/or non-responsiveness to touch. Survival rate (and duration) may also be used to evaluate the efficacy of a human engineered immune cell (e.g., T cell, B cell, or NK cell) therapy (and/or anti-CRS treatment).

Efficacy may also be evaluated by examining cytokine-induced liver and kidney damage. This may be determined, for example, by a serum biochemical analysis of liver-kidney function, such as measuring levels of aspartate transaminase (AST), albumin, total bilirubin, creatinine and blood urea nitrogen.

In some embodiments, the change in liver weight of preclinical mouse model is indicative of the efficacy of the human engineered immune cell (e.g., T cell, B cell, or NK cell) therapy (and, optionally, the CRS treatment). A healthy mouse's liver weight is approximately 5% of its body weight. Injection of tumor cells (e.g., Raji_Luc cells) leads to dissemination of the tumor cells to the liver, increasing the liver weight. By measuring the weight of the liver after engineered immune cell (e.g., T cell, B cell, or NK cell) therapy (and/or anti-CRS treatment), one may determine whether the treatment effectively eliminated or reduced tumor cell accumulation in the liver.

Methods for Assessing Side Effects of CAR Immune Cell (e.g., T Cell, B Cell, NK Cell) Therapy In some embodiments, the methods described herein may be used to assess the possible side effects of engineered immune cell (e.g., T cell, B cell, or NK cell) therapy. Possible side effects include but are not limited to cytokine release syndrome (CRS), macrophage activation syndrome (MAS), neurotoxicity (encephalopathy syndrome), tumor lysis syndrome (TLS), anaphylaxis, on-target, off-tumor toxicity, and B cell aplasia.

With respect to CRS, certain cytokines can be measured in a blood sample from the PBMC humanized mouse model following administration of the engineered immune cell (e.g., T cell, B cell, or NK cell) therapy and/or CRS treatment. For example, the cytokine may be selected from the group consisting of IFN-γ, IL-10, IL-6, IL-2, IL-4, and TNFα. The level of cytokine measured is indicative of the severity of immunotoxicity of the engineered immune cell (e.g., T cell, B cell, or NK cell) therapy. In some embodiments, the method further comprises determining that the severity of immunotoxicity of the engineered immune cell (e.g., T cell, B cell, or NK cell) therapy is high (e.g., the likelihood of CRS induction is high) when: an IFN-T level in the mouse is ≥1,800 pg/ml t10%; an IL-10 level in the mouse is ≥120 pg/ml±10%; an IL-6 level in the mouse is ≥25 pg/ml±10%; an IL-2 level in the mouse is ≥80 pg/ml±10%; an IL-4 level in the mouse is ≥120 pg/ml±10%; TNFα level in the mouse is ≥120 pg/ml±10%; MCP-1 level in the mouse is ≥120 pg/ml±10%; GM-CSF level in the mouse is ≥600 pg/ml t10%; and IL8 level in the mouse is ≥15 pg/ml±10%.

Macrophage activation syndrome (MAS) or hemophagocytic lymphohistiocytosis (HLH), which clinically manifests as liver dysfunction, increased ferritin levels and, in some cases, decreased fibrinogen levels, may also be examined using the mouse models described herein. Macrophages mediate the major production of cytokines including IL-6, IL-1, and IFN-γ, and their activation (MAS) is thought to play a role in CRS (Hao et al., Experimental Hematology & Oncology, 2020, 9:15). Therefore, elevated levels of the three cytokines in the mouse model may indicate that that the engineered immune cell (e.g., T cell, B cell, or NK cell) therapy may result in MAS. Likewise, the mouse may be administered a MAS treatment to determine whether the treatment would prevent or reduce MAS in the human subject. Examples of MAS treatments include but are not limited to, glucocorticoids (e.g., methylprednisone, dexamethasone), cyclosporin A, etoposide, immunoglobulins, and cyclophosphamide.

Neurotoxicity (encephalopathy syndrome), or immune effector cell-associated neurotoxicity syndrome (ICANS) can develop approximately 5-17 days after engineered immune cell (e.g., T cell, B cell, or NK cell) therapy in humans (Herlopian et al., Neurology, 2018, 91(5): 227-229). It is characterized by global encephalopathy, aphasia, seizure/seizure-like activity, obtundation, tremor/myoclonus, and hallucinations. Subjects with neurotoxicity also have high levels of IFN-γ, IL-6, and TNF-α. Elevated levels of the three cytokines in the mouse model may indicate that the engineered immune cell (e.g., T cell, B cell, or NK cell) therapy may result in neurotoxicity. Therefore, in some embodiments, the mouse may be administered a neurotoxicity treatment to determine whether the treatment would prevent or reduce neurotoxicity in the human subject. Examples of neurotoxicity treatments include but are not limited to corticosteroids (e.g., dexamethasone, prednisone), anti-IL-6 antibodies (e.g., siltuximab), and platelet hypertransfusion.

Additional Embodiments

Additional embodiments relating to the use of the present disclosure are provided in the numbered paragraphs below:
1. A method comprising:
  engrafting an immunodeficient mouse with tumor cells;
  engrafting the mouse with human peripheral blood mononuclear cells (PBMCs);
  administering to the mouse human immune cells engineered to express a chimeric antigen receptor (CAR) that specifically targets a cell surface antigen on tumor cells (human CAR immune cells); and
assaying the mouse for induction of cytokine release syndrome (CRS) and/or efficacy of the human CAR immune cells for treating the tumor cells.

2. The method of paragraph 1 comprising engrafting the mouse with a patient derived xenograft (PDX) comprising the tumor cells.

3. The method of paragraph 1 or paragraph 2, wherein the mouse is engrafted with 0.1-5.0×106 tumor cells.

4. The method of paragraph 3, wherein the mouse is engrafted with 0.25-0.5×106 tumor cells.

5. The method of any one of the preceding paragraphs, wherein the tumor cells are from a tumor cell line or a patient-derived xenograft (PDX).

6. The method of any one of the preceding paragraphs, further comprising irradiating the mouse.

7. The method of paragraph 6, wherein the mouse is engrafted with the tumor cells immediately after irradiating the mouse.

8. The method of paragraph 6, wherein the mouse is engrafted with the tumor cells 4-24 hours after irradiating the mouse.

9. The method of any one of the preceding paragraphs, wherein the mouse is engrafted with 0.5-3.0×107 PBMCs.

10. The method of paragraph 9, wherein the mouse is engrafted with 1.5×107 PBMCs.

11. The method of any one of paragraphs 6-10, wherein the mouse is engrafted with the PBMCs immediately after irradiating the mouse.

12. The method of any one of paragraphs 6-10, wherein the mouse is engrafted with the PBMCs 4-24 hours after irradiating the mouse.

13. The method of any one of paragraphs 1-10, wherein the mouse is engrafted with the PBMCs and administered the human CAR immune cells simultaneously.

14. The method of any one of the preceding paragraphs, wherein the mouse is administered the CAR immune cell (e.g., T cell, B cell, NK cell) therapy 6-12 days after tumor cell engraftment.

15. The method of any one of the preceding paragraphs, wherein the mouse is administered 1.0-5.0×106 human CAR immune cells.

16. The method of any one of the preceding paragraphs, wherein the PBMCs and the human CAR immune cells are from different donor subjects.

17. The method of any one of paragraphs 1-15, wherein the PBMCs and the human CAR immune cells are from the same donor subject.

18. The method of paragraph 17, wherein the tumor cells, the PBMCs, and the human CAR immune cells are from the same donor subject.

19. The method of any one of the preceding paragraphs further comprising administering to the mouse a candidate agent effective for treatment of cytokine release syndrome (CRS) and then assaying the mouse for induction of CRS and efficacy of the human CAR immune cell for treating the tumor cells.

20. The method of paragraph 19, wherein the candidate agent effective for treatment of CRS is administered immediately to 12 days after the human CAR immune cells are administered.

21. The method of paragraph 20, wherein the candidate agent effective for treatment of CRS is administered 5-9 days after the human CAR immune cells are administered.

22. The method of paragraph 20, wherein the candidate agent effective for treatment of CRS is administered 1-3 days before the human CAR immune cells are administered.

23. The method of any one of paragraphs 20-22, wherein the candidate agent is selected from the group consisting of: IL-6 antagonists, anti-IL-6 antibodies, corticosteroids, anti-TNF-α drugs, IL-1R inhibitors, GM-CSF inhibitors, and small molecule inhibitors.

24. The method of paragraph 23, wherein the IL-6 antagonist is tocilizumab.

25. The method of any one of the preceding paragraphs, wherein the tumor cells, PBMCs and human CAR immune cells are administered to the mouse via tail vein injection.

26. The method of any one of paragraphs 6-25, wherein the mouse is irradiated with 100-1300 cGy.

27. The method of any one of the preceding paragraphs, wherein the mouse is a non-obese diabetic (NOD) mouse.

28. The method of any one of the preceding paragraphs, wherein the mouse comprises a null mutation in a Prkdc gene and a null mutation in an Il2rg gene.

29. The method of paragraph 28, wherein the mouse has a NOD-Cg.-PrkdcscidIL2rgtm1wJl/SzJ genotype.

30. The method of paragraph 28 or 29, wherein the mouse lacks functional major histocompatibility complex I (MHC I) and major histocompatibility complex II (MHC II).

31. The method of paragraph 30, wherein the mouse comprises a null H2-Ab1 gene.

32. The method of paragraph 30 or 31, wherein the mouse comprises a null MHC Class I H2-K1 gene.

33. The method of any one of paragraphs 30-32, wherein the mouse comprises a null MHC Class I H2-D1 gene.

34. The method of paragraph 33, wherein the mouse is a NOD.Cg-Prkdcscid H2-K1tm1Bpe H2-Ab1em1Mvw H2-D1tm1Bpe Il2rgtm1Wjl/SzJ mouse (NSG-(Kb db)null (IAnull) mouse).

35. The method of any one of the preceding paragraphs, wherein assaying the mouse for induction of CRS comprises measuring a circulating level of a cytokine selected from the group consisting of: interleukin (IL)-6, IL10, interferon (IFN)-γ, monocyte chemoattractant protein 1 (MCP-1), granulocyte-macrophage colony-stimulating factor (GM-CSF), tumor necrosis factor (TNF), IL-1, IL-2, IL-2-receptor alpha (IL-2Rα), IL-8, IL-4, IL-18, and macrophage inflammatory protein (MIP) 4.

36. The method of paragraph 31, further comprising determining that the likelihood of CRS induction is high when:
a human IFN-γ level in the mouse is ≥1,800 pg/ml±10%;
a human IL-10 level in the mouse is ≥120 pg/ml±10%;
a human IL-6 level in the mouse is ≥25 pg/ml±10%;
a human IL-2 level in the mouse is ≥80 pg/ml±10%;
a human IL-4 level in the mouse is ≥120 pg/ml±10%;
a human TNFα level in the mouse is ≥120 pg/ml±10%;
a human IL-8 level in the mouse is ≥15 pg/ml±10%;
a human MCP-1 level in the mouse is ≥120 pg/ml±10%; and/or
a human GM-CSF level in the mouse is ≥600 pg/ml±10%.

37. The method of any one of the preceding paragraphs, further comprising assaying the mouse for macrophage activation syndrome (MAS).

38. The method of paragraph 37, wherein the likelihood of MAS is determined by measuring the circulating levels of IL-6, IL-1, and/or IFN-γ.

39. The method of any one of the preceding paragraphs, further comprising assaying the mouse for neurotoxicity.

3640 The method of paragraph 39, wherein the likelihood of neurotoxicity is determined by measuring the circulating levels of IFN-γ, IL-6, and/or TNF-α.

41. The method of any one of the preceding paragraphs, further comprising performing a serum biochemical analysis of liver-kidney function.

42. The method of paragraph 41, wherein the serum biochemical analysis comprises measuring the levels of at least one of the following markers: aspartate transaminase (AST), albumin, total bilirubin, creatinine, or blood urea nitrogen.

43. The method of any one of paragraphs 19-42, further comprising determining whether the candidate agent effective for treatment of CRS reduces the level of one or more circulating cytokines.

44. The method of paragraph 43, comprising determining that the candidate agent effective for treatment of CRS does reduce the level of one or more circulating cytokines when the circulating level of the one or more cytokines is reduced 30-100% in a mouse administered the human CAR immune cell (e.g., T cell, B cell, NK cell) therapy and the candidate agent, relative to a mouse administered the human CAR immune cell (e.g., T cell, B cell, NK cell) therapy without the candidate agent.

45. The method of any one of the preceding paragraphs, wherein assaying the mouse for efficacy of the human CAR immune cells for treating the tumor cells comprises measuring the growth of the tumor cells.

46. The method of paragraph 45, wherein the growth of the tumor cells is measured over time.

47. The method of paragraph 45 or 46, wherein a reduction in tumor volume of 20% or more relative to a control mouse that was not administered the human CAR immune cell (e.g., T cell, B cell, NK cell) therapy is indicative of efficacy.

48. The method of paragraph 45 or paragraph 46, wherein a reduction in tumor burden of 20% or more relative to a control mouse that was not administered the human CAR immune cell (e.g., T cell, B cell, NK cell) therapy is indicative of efficacy.

49. The method of any one of paragraphs 45-48, wherein the growth of the tumor cells is used to determine progression-free survival, tumor volume doubling time, relative tumor volume, tumor growth inhibition, or tumor growth rate.

50. The method of any one of the preceding paragraphs, wherein the human CAR immune cells are universal allogeneic human CAR immune cells.

51. A method comprising:
    irradiating an immunodeficient mouse;
    engrafting the mouse with tumor cells;
    engrafting the mouse with human peripheral blood mononuclear cells (PBMCs);
        administering to the mouse universal allogeneic human immune cells engineered to express a chimeric antigen receptor (CAR) that specifically targets a cell surface antigen on tumor cells (universal allogeneic human CAR immune cells); and
    assaying the mouse for induction of cytokine release syndrome (CRS) and/or efficacy of the universal allogeneic human CAR immune cells for treating the tumor cells.

52. The method of any one of the preceding paragraphs, wherein the human immune cells are selected from the group consisting of: T cells, natural killer cells, B cells, monocytes, dendritic cells, and neutrophils.

53. The method of paragraph 52, wherein the human immune cells comprise at least two of the following: T cells, natural killer cells, B cells, monocytes, dendritic cells, and neutrophils.

EXAMPLES

Example 1

Figure 1A:
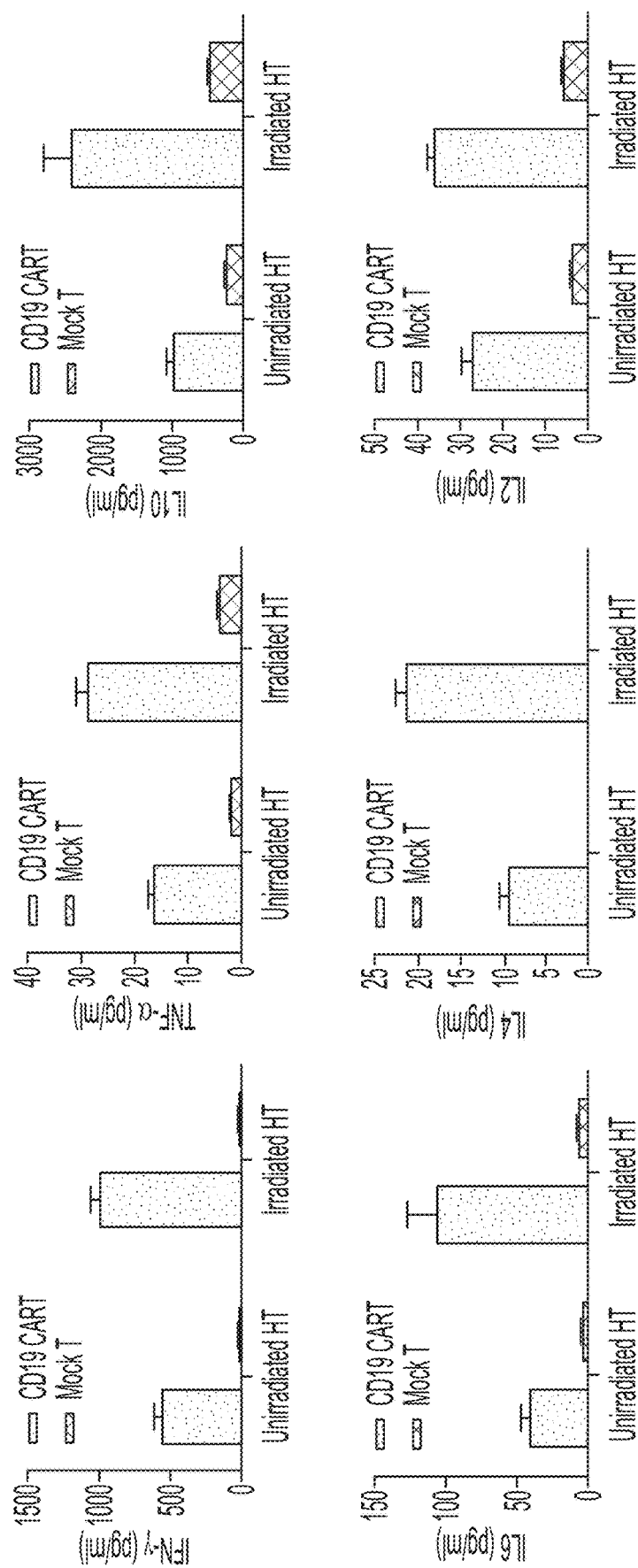
FIG. 1A provides data demonstrating that irradiated MHC class I/II knockout (KO) NSG™ mice had increased cytokine release compared to control unirradiated mice after CD19 CAR T cell treatment.
Figure 1B:
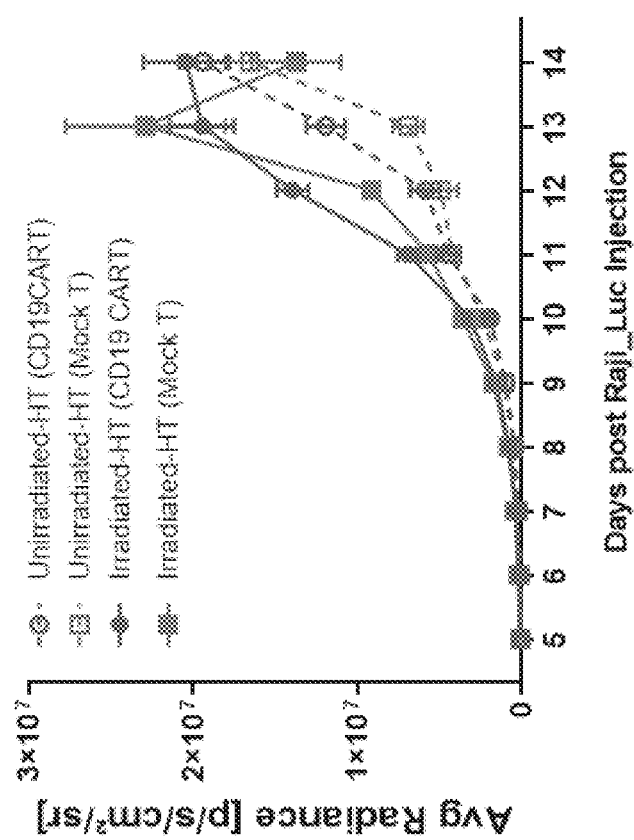
FIG. 1B provides data demonstrating that unirradiated mice (D10) and irradiated mice (D9) had similar tumor burden upon CAR T cell treatment.

The effects of irradiation on cytokine release following CAR T19 treatment were examined. Six- to seven-week-old female MHC class I/II KO NSG™ mice received 100cGy irradiation. Then, unirradiated and irradiated MHC class I/II KO NSG™ were engrafted with an IV injection of Raji_Luc $0.25 \times 10^6$/mouse at least four hours after irradiation. Raji_Luc tumor growth was monitored by in vivo Bioluminescence Imaging (BLI). Next, the irradiated mice and unirradiated mice received $10 \times 10^6$ CD19 CAR T or $10 \times 10^6$ Mock T CAR T. The mice were found to have a similar tumor burden. Mice were bled 2 days after CAR T treatment and circulating cytokine concentrations were measured by the BD cytometric bead array (CBA) Th1/Th2 II kit. Daily body weight and clinical observations were taken after the CAR T treatment. While there was no significant difference in CAR T efficacy, irradiated mice were more sensitive to CAR T induced cytokine release. This data demonstrated irradiated MHC class I/II KO NSG™ mice had increased cytokine release compared to control unirradiated mice after CAR T19 treatment (FIGS. 1A-1B).

Example 2

Figure 2A:
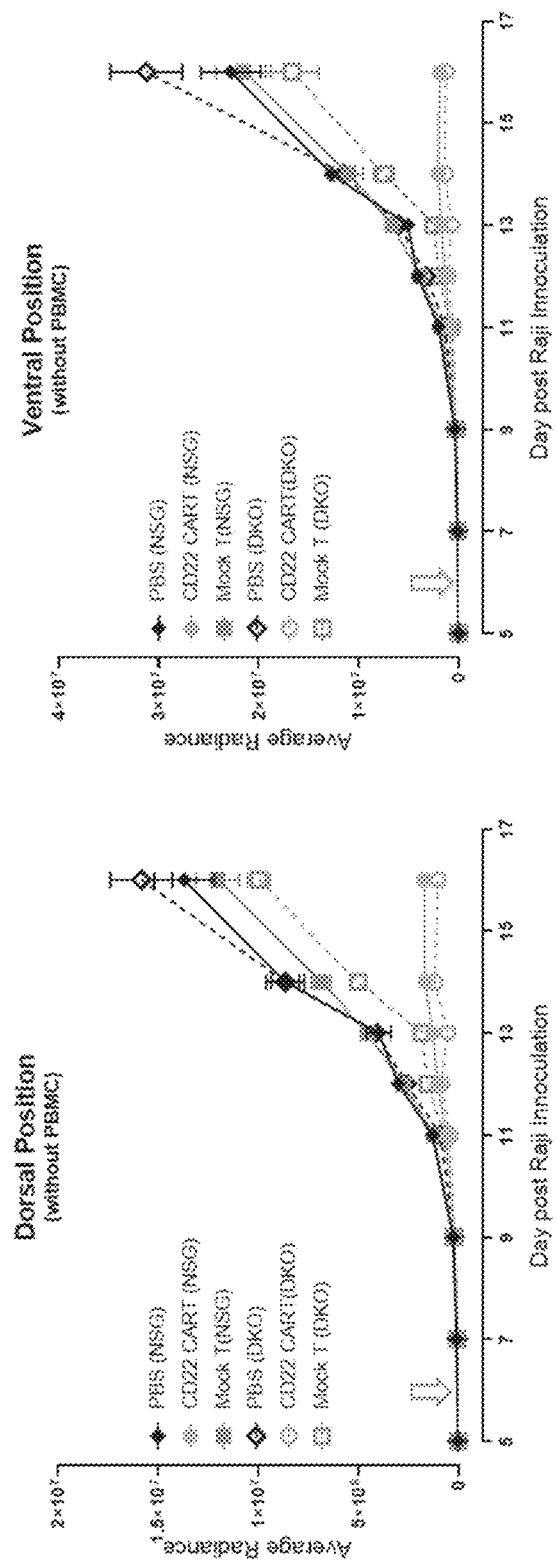
FIG. 2A provides data demonstrating that CD22 CAR T cell treatment in mice with low tumor burden efficiently blocked Raji-Luc tumor growth in both NSG™ and Raji-Luc NSG Class I/II KO (DKO).
Figure 2B:
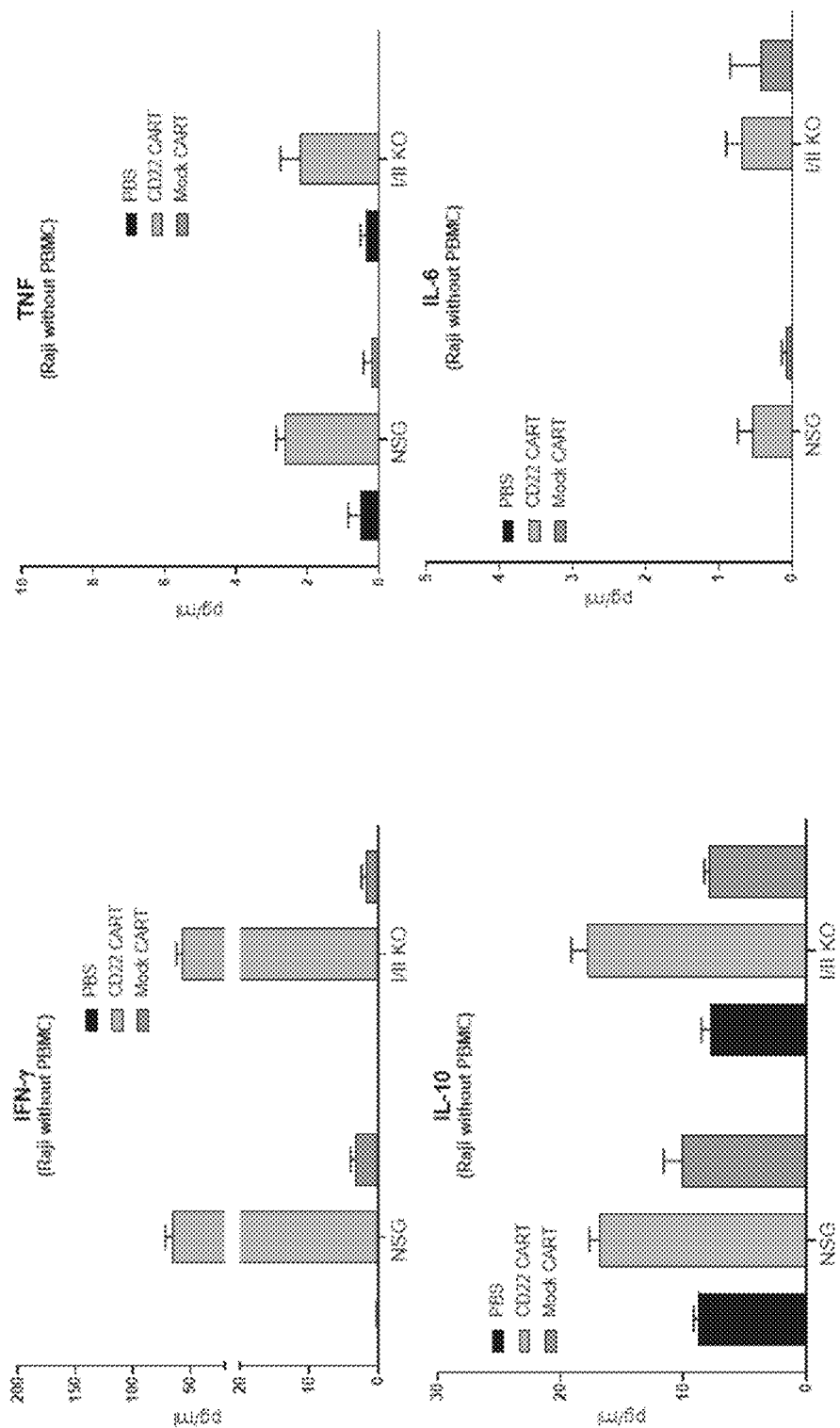
FIG. 2B provides data showing very low levels of human cytokine induction after CD22 CAR T cell infusion in both the Raji-Luc NSG™ and Raji-Luc NSG™ I/II KO models.

The effects of CD22 CAR T cell therapy on mice with low tumor burden were examined. Irradiated DKO NSG™ and NSG™ mice were engrafted with $0.25 \times 10^6$ Raji_Luc cells (day 0, D0), followed by $3 \times 10^6$ CD22 CAR T treatment at D6. As shown in FIG. 2A, CD22 CAR T has similar efficacy in both DKO mice and NSG™ mice, as demonstrated by an in vivo Bioluminescence Imaging (BLI) plot generated using average radiance to quantitatively measure tumor burden. Both DKO and NSG™ mice were found to have very low amounts of cytokine release upon CAR T treatment. Mice were bled 2 days after CAR T treatment and circulating cytokine concentrations were measured by the BD CBA Th1/Th2 II kit (FIG. 2B). This data demonstrated that CD22 CAR T treatment on mice with low tumor burden has good efficacy and induce very low levels of human cytokine (FIGS. 2A-2B).

Example 3

Figure 3A:
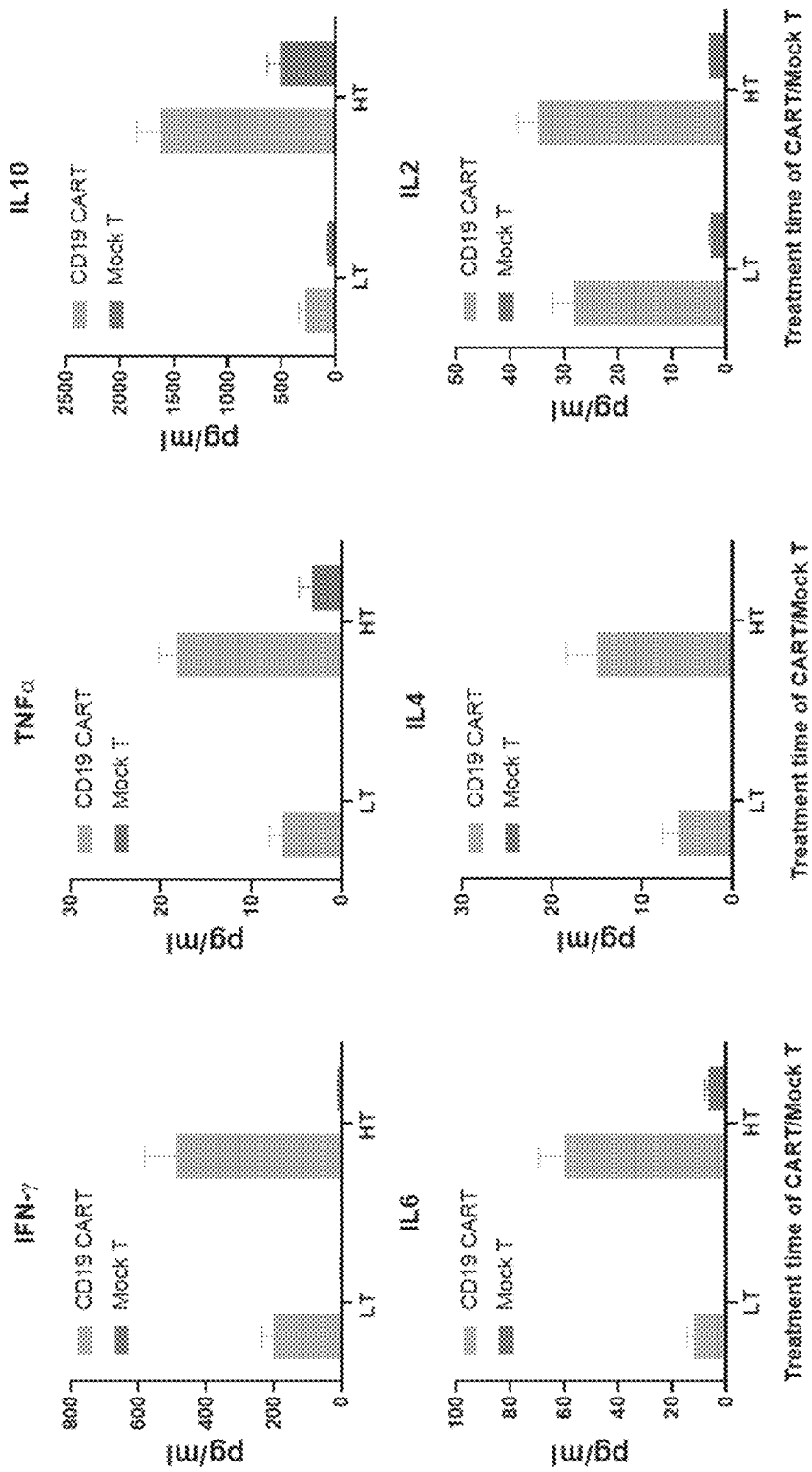
FIG. 3A provides data demonstrating that increased cytokine levels were correlated with high tumor burden following CD19 CAR T cell treatment in the Raji-Luc model.
Figure 3B:
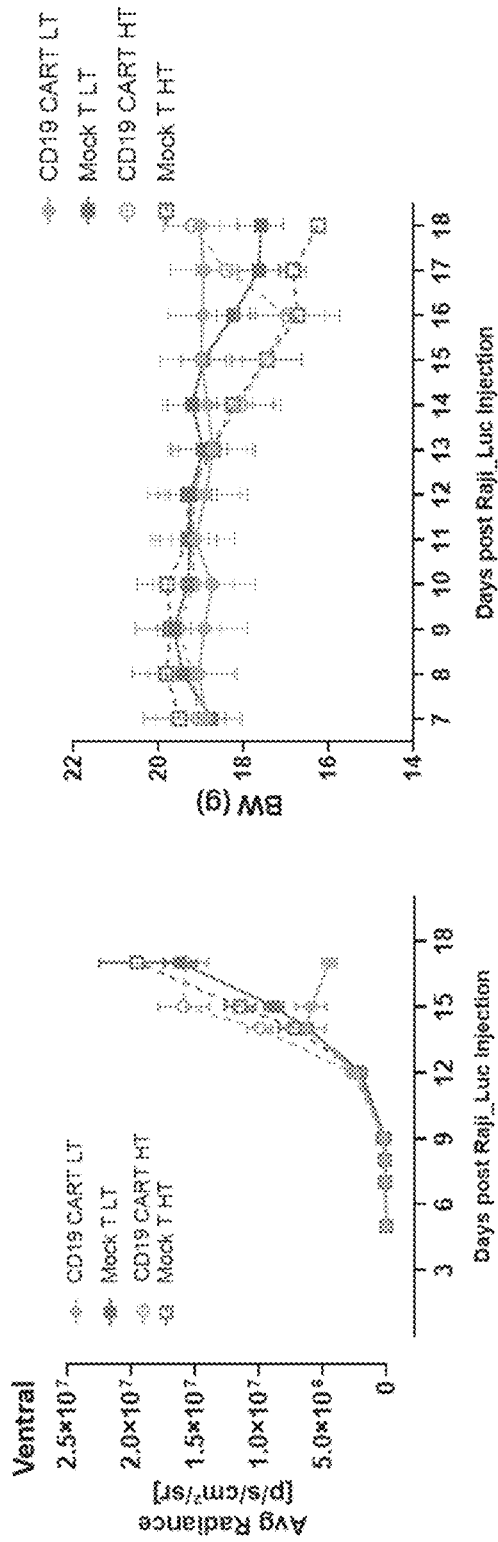
FIG. 3B provides data demonstrating that CD19 CAR T cell treatment in mice with a high tumor burden was poorly effective, while CD19 CAR T cell treatment in mice with a lower tumor burden can prevent tumor progression.

The effect of CD19 CAR T cell therapy on mice with high tumor burdens was examined. Irradiated DKO NSG™ were engrafted with $0.25 \times 10^6$ Raji_Luc cells (D0), followed by $5 \times 10^6$ CD19 CAR T or $5 \times 10^6$ Mock T treatment at D9 or at D11. Mice sera were collected 2 days following CAR T/Mock T treatment. Raji_Luc tumor growth was monitored by In Vivo Bioluminescence Imaging (BLI). Mice with higher tumor burden (D11) had increased human cytokines (INF-γ, TNFα, IL10, IL6, and IL4) compared to mice with relatively low tumor burden after CD19 CAR T treatment (FIG. 3A). CD19 CAR T treatment on DKO mice with low Raji-Luc tumor burden significantly inhibited tumor growth and prevented mice body weight loss; CD19 CAR T treatment on DKO mice with high tumor burden result in poor efficacy (FIG. 3B). Both CAR T treated groups prevented mice body weight loss compared to PBS treated group. There were 5 mice per group and the data are presented as mean±SEM. This data demonstrated that CD19 CAR T treatment on mice with higher tumor burden has poor efficacy and high CRS induction (FIGS. 3A-3B).

Example 4

Figure 4:
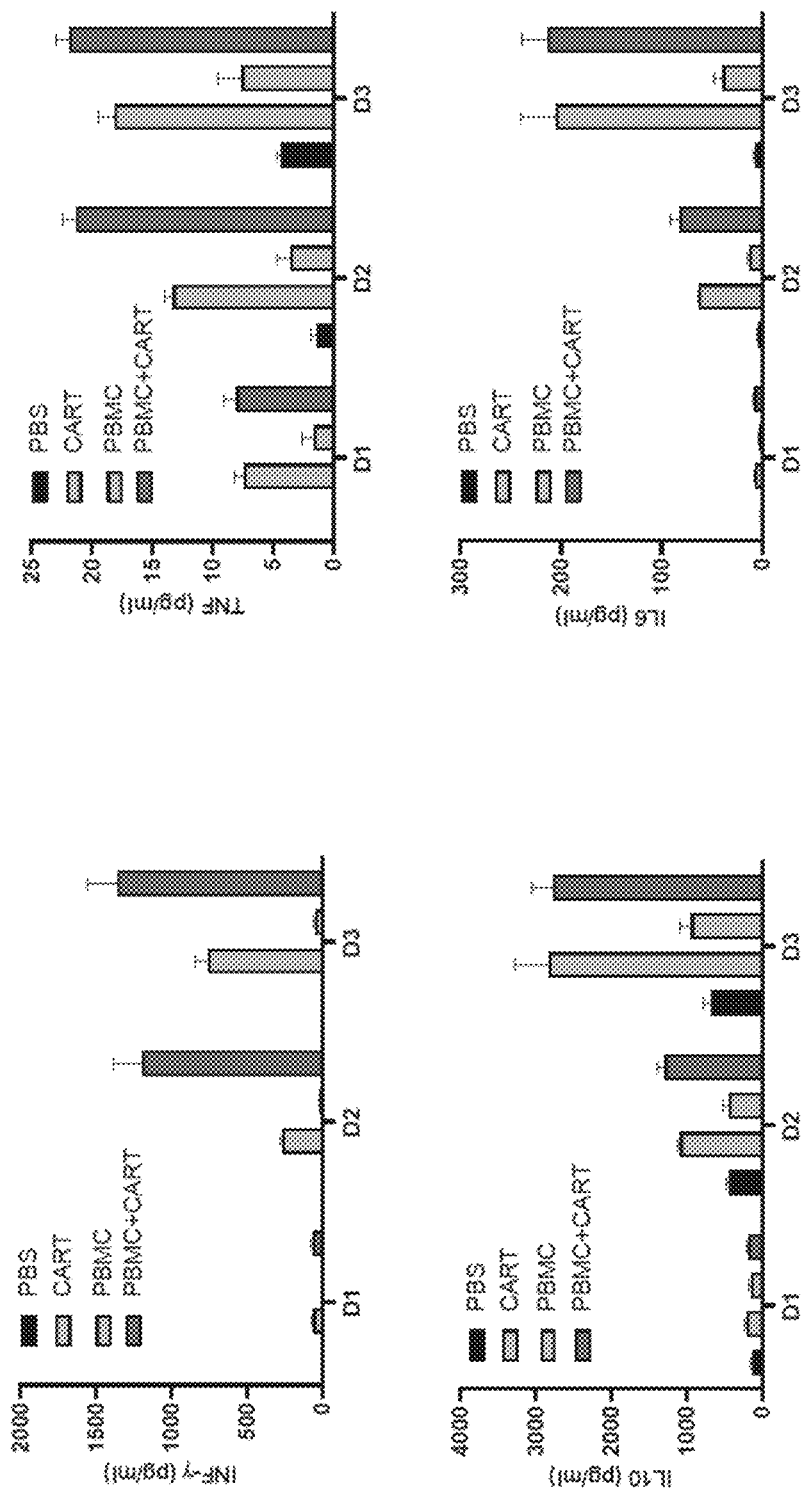
FIG. 4 shows a time-course of cytokine release from moderate tumor burden mice following autologous peripheral blood mononuclear cell (PBMC) engraftment/CD19

A time course of cytokine release from moderate tumor burden following autologous PBMC/CD19 CAR T treatment was undertaken. NSG™ mice were engrafted with an IV injection of $0.5 \times 10^6$/mouse after irradiation (D0). Raji_Luc tumor growth was monitored by In Vivo Bioluminescence Imaging (BLI). Mice were treated intravenously beginning on day 9 with PBS or 5×10⁶ CD19 CAR T, 15×10⁶ PBMC or 5×10⁶ CD19 CAR T plus 15×10⁶ PBMC. CD19 CAR T and the PBMCs were derived from the same donor. Mice sera were collected were at different days (D1, D2, D3) following CAR T/PBMC treatment. Circulating cytokine concentrations were measured by the BD CBA Th1/Th2 II kit. CD19 CAR T batch 1 and PBMC were from the same donor. There were 4 mice per group and the data are presented as mean±SEM. PBMC/CAR T co-treated mice had increased human IFN-γ, TNF and IL6 compared to mice receiving CD19 CAR T alone (FIG. 4). This data demonstrated that CAR T cell therapy induced higher levels of human cytokines in the PBMC humanized mice compared to the control mice that did not receive PBMCs.

Example 5

The effects of autologous CD22 CAR T treatment on PBMC humanized DKO mice on tumor progression and cytokine levels was examined. CD22 CAR T and PBMC were derived from the same donor. MHC class I/II KO NSG mice were engrafted with an IV injection of 0.5×10⁶/mouse after irradiation (D0). Raji_Luc tumor growth was monitored by In Vivo Bioluminescence Imaging (BLI). Two days after Raji_Luc engraftment mice were either received 15M PBMC. Six days after Raji_Luc engraftment, mice received: 1) PBS; 2) 5×10⁶ CD19 CAR T; or 3) 5×10⁶ Mock T. Mice were bled 2 days after CAR T/Mock treatment and circulating cytokine concentrations were measured by the BD CBA Th1/Th2 II kit. Daily body weight and clinical observation were performed after CAR T treatment. As show in the top portion of FIG. 5A, in vivo Bioluminescence Imaging (BLI) was plotted using average radiance to quantitatively measure tumor burden. The bottom portion of FIG. 5A provides dorsal (D) and ventral (V) images for each mouse. There were 4-5 mice per group and data are presented as mean±SEM. CAR T efficacy was determined over that seen with the PBS or mock CAR T treatment. Autologous CD22 CAR T treatment with PBMC humanization induced higher human cytokines ((INF-γ, TNFα, IL10, IL6, IL4 and IL2) compared to Mock T treatment on PBMC humanized mice (FIG. 5B). This data demonstrates that autologous CD22 CAR T treatment on PBMC humanized DKO mice blocked Raji_Luc tumor progression and induced higher human cytokines compared to Mock T treatment (FIGS. 5A-5B). Therefore, a CAR T cell drug dose range may be used, in some instances, to determine an efficacious dose with less cytokine induction and toxicity. Further, the data demonstrates that one may predict toxicity on an individual, in some instances, prior to the treatment so that the subject can be pretreated with a drug to reduce cytokine induction.

Example 6

The PBMC humanized DKO mice model was used to examine efficacy and cytokine release. PBMC humanized mice or control (no PBMC) mice were treated IV with PBS or 5×10⁶ CD19 CAR T cells or 5×10⁶ Mock T cells 6 days after Raji_Luc (0.25×10⁶ per mouse). The CD19 CAR T cells and PBMCs were derived from the same donor. Sera were collected 2 days after CAR T/PBMC treatment and cytokine level (D8) were analyzed by the BD CBA Th1/Th2 II kit. There were 5 mice per group and the data are presented as mean±SEM. Increased cytokine release from moderate tumor burden mice following CD19 CAR T/PBMC treatment compared to mice receiving CD19 CAR T without PBMC humanization, as shown in FIG. 6A. FIG. 6B shows in vivo Bioluminescence Imaging (BLI) plotted using average radiance to quantitatively measure tumor burden. CAR T efficacy was seen with and without PBMC humanization but a complete response was evident with PBMC humanization at day 12. The bioluminescence images of these mice at different experiment days are shown in FIG. 6C. All mice were imaged with identical camera settings. Dorsal (D) and ventral (V) images are shown for each. There were 5 mice per group and data are presented as mean±SEM. This data demonstrates that PBMC humanized DKO mice model provide a unique platform to evaluate both efficacy (imaging) and cytokine release (FIGS. 6A-6C).

Example 7

Efficacy and cytokine release from moderate tumor burden following autologous PBMC/CD19 CAR T treatment were examined. DKO NSG™ mice were engrafted with an intravenous injection of 0.25×10⁶/mouse after irradiation (D0). Raji_Luc tumor growth was monitored by in vivo Bioluminescence Imaging (BLI). Mice were treated intravenously beginning on day 8 with PBS or 15×10⁶ PBMC or 1×10⁶ CD19 CAR T plus 15×10⁶ PBMC, 3×10⁶ CD19 CART plus 15×10⁶ PBMC or 5×10⁶ CD19 CAR T plus 15×10⁶ PBMC. CD19 CAR T and the PBMCs were derived from the same donor. Mice sera were collected 2 days following CAR T/PBMC treatment. Circulating cytokine concentrations were measured by the BD CBA Th1/Th2 II kit. There were 5 mice per group and the data are presented as mean t SEM in FIGS. 7A-7B. PBMC/CAR T co-treated mice were found to have dose-dependent increased levels of human IFN-γ (FIG. 7B). The high CART dose had improved efficacy (tumor burden) compared to lower CART dose treatments (FIG. 7A, left graph), while both CART doses were observed to rescue mice body weight loss due to Raji_Luc tumor growth. (FIG. 7A, right graph). This data demonstrated that CAR T cell therapy induced higher levels of human cytokines in the PBMC humanized mice in a dose-dependent manner.

Example 8

The effects of CAR T cell therapy on human cytokines levels in PBMC humanized mice compared to the control mice that did not receive PBMCs following autologous PBMC/CD19 CAR T treatment were examined. CD19 CART cells were generated using a new CD19 CAR construct and a new PBMC donor (donor 9534). DKO NSG™ mice were engrafted with an intravenous injection of 0.25×10⁶/mouse after irradiation (D0). Raji_Luc tumor growth was monitored by in vivo Bioluminescence Imaging (BLI). Mice were treated intravenously beginning on day 8 with PBS or 15×10⁶ PBMC or 5×10⁶ CD19 CAR T alone, or 5×10⁶ CD19 CART plus 15×10⁶ PBMC. CD19 CAR T and the PBMCs were derived from the same donor. Mice sera were collected 2 days following CAR T/PBMC treatment. Circulating cytokine concentrations were measured by the BD CBA Th1/Th2 II kit. There were 5 mice per group and the data are presented as mean±SEM. PBMC/CAR T co-treated mice and CART alone treated mice had decreased tumor burden (FIG. 8A) and did not lose significant body weight (FIG. 8B). Moreover, PBMC/CART co-treated mice had high levels of human IFN and TNF release compared to mice treated with CART alone (FIG. 8C).

Example 9

The efficacy of allogeneic CD19 CART treatment from different PBMC humanized mice with Raji_Luc tumor was examined. Allogeneic CD19 CART cells were generated using a modified CD19 CAR construct and a new PBMC donor. DKO NSG™ mice were engrafted with an intravenous injection of 0.25×10$^6$/mouse after irradiation (D0). Raji_Luc tumor growth was monitored by in vivo Bioluminescence Imaging (BLI). Mice were treated intravenously beginning on day 8 with PBS or 15×10$^6$ PBMC or 5×10$^6$ CD19 CAR T alone, or 5×10$^6$ CD19 CAR T plus 15×10$^6$ PBMC. Two different donors' PBMCs (PBMC 8058 or PBMC 9601) were used for the humanization. Allogeneic CART showed some level of efficacy through tumor burden imaging (FIG. 9A) and flow analysis CD3-CD19+ cell population (FIG. 9B). Allogeneic CD19 CART treatment blocked body weight loss induced by Raji-Luc tumor development (FIG. 9C).

Example 10

The variation of cytokine release from different PBMC humanized mice with Raji_Luc tumor following allogeneic CD19 CART treatment was examined. New allogeneic CD19 CART cells were generated using a new CD19 CAR construct and a new PBMC donor. DKO NSG™ mice were engrafted with an intravenous injection of 0.25×10$^6$/mouse after irradiation (D0). Raji_Luc tumor growth was monitored by In Vivo Bioluminescence Imaging (BLI). Mice were treated intravenously beginning on day 8 with PBS or 15×10$^6$ PBMC or 5×10$^6$ CD19 CAR T alone, or 5×10$^6$ CD19 CART plus 15×10$^6$ PBMC. Two different PBMC donors (PBMC 8058 or PBMC 960)1 were used for the humanization. Mice sera were collected at different days (D2, D3) following CAR T/PBMC treatment. Circulating cytokine concentrations were measured by the BD CBA Th1/Th2 II kit. Mice with CD19 CART/PBMC 9601 treatment had higher levels of IL10 and IL6 release compared to mice treated with CD19 CART/PBMC 8508 (FIGS. 10A-10C), demonstrating a donor-specific dose response.

Example 11

The variation of cytokine release and toxicity from different PBMC humanized mice following autologous CD19 CART treatment was examined. Autologous CD19 CART cells were generated using a new CD19 CAR construct (used in Example 8) from either PBMC donor 9534 or PBMC donor 9531. DKO NSG™ mice were engrafted with an intravenous injection of PBMC 15×10$^6$/mouse after irradiation (D0). Mice were treated intravenously beginning on day 6 with PBS or 5×10$^6$ Mock T, or 5×10$^6$ autologous CD19 CAR T. Mice sera were collected at different days following CAR T/PBMC treatment (FIG. 11A). Circulating cytokine concentrations were measured by the BD CBA Th1/Th2 II kit. Six days after CART treatment, whole blood and spleen were collected from all mice for flow analysis of the CD3-CD19+ population. Both autologous CD19 CART samples showed good efficacy and decreased the CD3-CD19+ population compared to the corresponding PBS control and Mock T treated mice (FIG. 11B). In contrast, the PBMC 9534-humanized mice had significant body weight loss (FIG. 11C) and significantly higher levels of IL-10 and IL-4 compared to the PBMC 9531-humanized mice after autologous CART treatment (FIG. 11D), demonstrating a donor-specific response.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method comprising:
   (a) administering to an irradiated immunodeficient mouse
      (i) human tumor cells that express a cell surface antigen and (ii) human peripheral blood mononuclear cells (PBMCs) to produce a humanized immunodeficient mouse engrafted with a human tumor and human PBMCs,
   wherein the human PBMCs develop into human cells selected from T cells, B cells, Natural Killer cells, and monocytes, wherein the human cells secrete human cytokines, and wherein the immunodeficient mouse is a non-obese diabetic (NOD) mouse comprising a null Prkdc gene, a null Il2rg gene, a null MHC Class I H2-K1 gene, a null MHC Class I H2-D1 gene, and a null MHC Class II H2-Ab1 gene;
   (b) administering engineered human immune cells to the humanized immunodeficient mouse, wherein the engineered human immune cells comprise a receptor that specifically binds to the cell surface antigen on the human tumor cells; and
   (c) measuring levels of the human cytokines circulating in the humanized immunodeficient mouse.

2. The method of claim 1, wherein the receptor is a chimeric antigen receptor (CAR) or a T cell receptor (TCR).

3. The method of claim 1, wherein the engineered human immune cells are regulatory T cells (Tregs) or tumor-infiltrating lymphocytes (TILs).

4. The method of claim 1, wherein the human tumor cells are primary tumor cells.

5. The method of claim 1, wherein the human tumor cells are cancerous cells.

6. The method of claim 1, wherein the human PBMCs and the engineered human immune cells are autologous, or wherein the human tumor cells, the human PBMCs and the engineered human immune cells are autologous.

7. The method of claim 1, wherein the human PBMCs and the engineered human immune cells are allogeneic, or wherein the human tumor cells and the engineered human immune cells are allogeneic.

8. The method of claim 1, further comprising administering to the humanized immunodeficient mouse a candidate agent for treating cytokine release syndrome (CRS) prior to the measuring.

9. The method of claim 1, wherein the immunodeficient mouse is a NOD.Cg-Prkdc$^{scid}$ H2-K1$^{tm1Bpe}$ H2-Ab1$^{em1Mvw}$ H2-D1$^{tm1Bpe}$ Il2rg$^{tm1Wjl}$/SzJ mouse.

10. The method of claim 1, wherein the human cytokines are selected from the group consisting of: interleukin (IL)-6, IL-10, interferon (IFN)-γ, monocyte chemoattractant protein 1 (MCP-1), granulocyte-macrophage colony-stimulating factor (GM-CSF), tumor necrosis factor (TNF), IL-1, IL-2, IL-2-receptor alpha (IL-2Rα), IL-8, IL-4, IL-18, and macrophage inflammatory protein (MIP) 4.

11. The method of claim 1, further comprising assaying the immunodeficient mouse for macrophage activation syndrome (MAS).

\* \* \* \* \*